US009914950B2

(12) United States Patent
Lazinski et al.

(10) Patent No.: US 9,914,950 B2
(45) Date of Patent: Mar. 13, 2018

(54) HOMOPOLYMER MEDIATED NUCLEIC ACID AMPLIFICATION

(71) Applicant: Tufts University, Medford, MA (US)

(72) Inventors: David W. Lazinski, Franklin, MA (US); Andrew Camilli, Sharon, MA (US)

(73) Assignee: Tufts University, Medford, MA (US)

( * ) Notice: Subject to any disclaimer, the term of this patent is extended or adjusted under 35 U.S.C. 154(b) by 81 days.

(21) Appl. No.: 14/423,311

(22) PCT Filed: Aug. 23, 2013

(86) PCT No.: PCT/US2013/056383
§ 371 (c)(1),
(2) Date: Feb. 23, 2015

(87) PCT Pub. No.: WO2014/031954
PCT Pub. Date: Feb. 27, 2014

(65) Prior Publication Data
US 2015/0203887 A1    Jul. 23, 2015

Related U.S. Application Data

(60) Provisional application No. 61/692,502, filed on Aug. 23, 2012.

(51) Int. Cl.
C12P 19/34    (2006.01)
C12Q 1/68    (2018.01)

(52) U.S. Cl.
CPC ............ *C12P 19/34* (2013.01); *C12Q 1/6855* (2013.01)

(58) Field of Classification Search
CPC .. C12Q 1/6855; C12Q 2525/173; C12P 19/34
USPC ...................................................... 435/91.2
See application file for complete search history.

(56) References Cited

U.S. PATENT DOCUMENTS

| 5,994,058 | A | 11/1999 | Senapathy |
| 6,114,149 | A * | 9/2000 | Fry ................... C12N 15/1096 435/6.16 |
| 2010/0145037 | A1 | 6/2010 | Makarov et al. |

FOREIGN PATENT DOCUMENTS

| WO | WO 92/13088 A1 | 8/1992 |
| WO | WO 01/90415 A2 | 11/2001 |
| WO | WO 02/44399 A2 | 6/2002 |
| WO | WO 09/54922 A1 | 4/2009 |

OTHER PUBLICATIONS

Deng et al., (Nucleic Acids Research, vol. 9, No. 16, pp. 4173-4188, 1981).*
[No Author Listed], Paired-End Sample Preparation Guide. Illumina. Catalog No. PE-930-1001. Part No. 1005063 Rev. E. Feb. 2011 40 pages.
Barker et al., Two Methods of Whole-Genome Amplification Enable Accurate Genotyping Across a 2320-SNP Linkage Panel. Genome Res. 2004;14:901-7. doi: 10.1101/gr.1949704.
Dalia et al., Characterization of Undermethylated Sites in Vibrio cholera. J Bacteriol. 2013;195(10):2389-99. doi: 10.1128/JB.02112-12.
Klein et al., Identification of essential genes of the periodontal pathogen *Porphyromonas gingivalis*. BMC Genomics. 2012;13:578. doi:10.1186/1471-2164-13-578. 17 pages.
Land et al., 5'-Terminal sequences of eukaryotic mRNA can be cloned with high efficiency. Nucleic Acids Res. 1981;9(10):2251-66.
Lazinski et al., Homopolymer tail-mediated ligation PCR: a streamlined and highly efficient method for DNA cloning and library construction. Biotechniques. Jan. 2013;54(1):25-34. doi:10.2144/000113981. Epub Jul. 1, 2013. 10 pages.
Liu et al., Whole Genome Amplification by T7-Based Linear Amplification of DNA (TLAD): I. CIP Treatment of Samples and Tailing Reaction with Terminal Transferase. Cold Spring Harb Protoc. May 2008;3(5):1-5. doi: 10.1101/pdb.prot5002.
Seed et al., A bacteriophage encodes its own CRISPR/Cas adaptive response to evade host innate immunity. Nature. Feb. 28, 2013;494:489-91. doi:10.1038/nature11927.
Troy et al., Understanding Barriers to Borrelia burgdorferi Dissemination during Infection Using Massively Parallel Sequencing. Infect Immun. 2013;81(7):2347-57. doi: 10.1128/IAI.00266-13.

* cited by examiner

*Primary Examiner* — Cynthia B Wilder
(74) *Attorney, Agent, or Firm* — Wolf, Greenfield & Sacks, P.C.

(57) ABSTRACT

According to some aspects of the invention, provided herein are methods of amplifying nucleic acids using homopolymer-mediated ligation. The methods, in some embodiments, comprise adding a first homopolymer of at least 12 nucleotides to each 3' end of blunt-ended double-stranded nucleic acid containing a target nucleic acid, thereby producing a partially double-stranded nucleic acid.

13 Claims, 18 Drawing Sheets

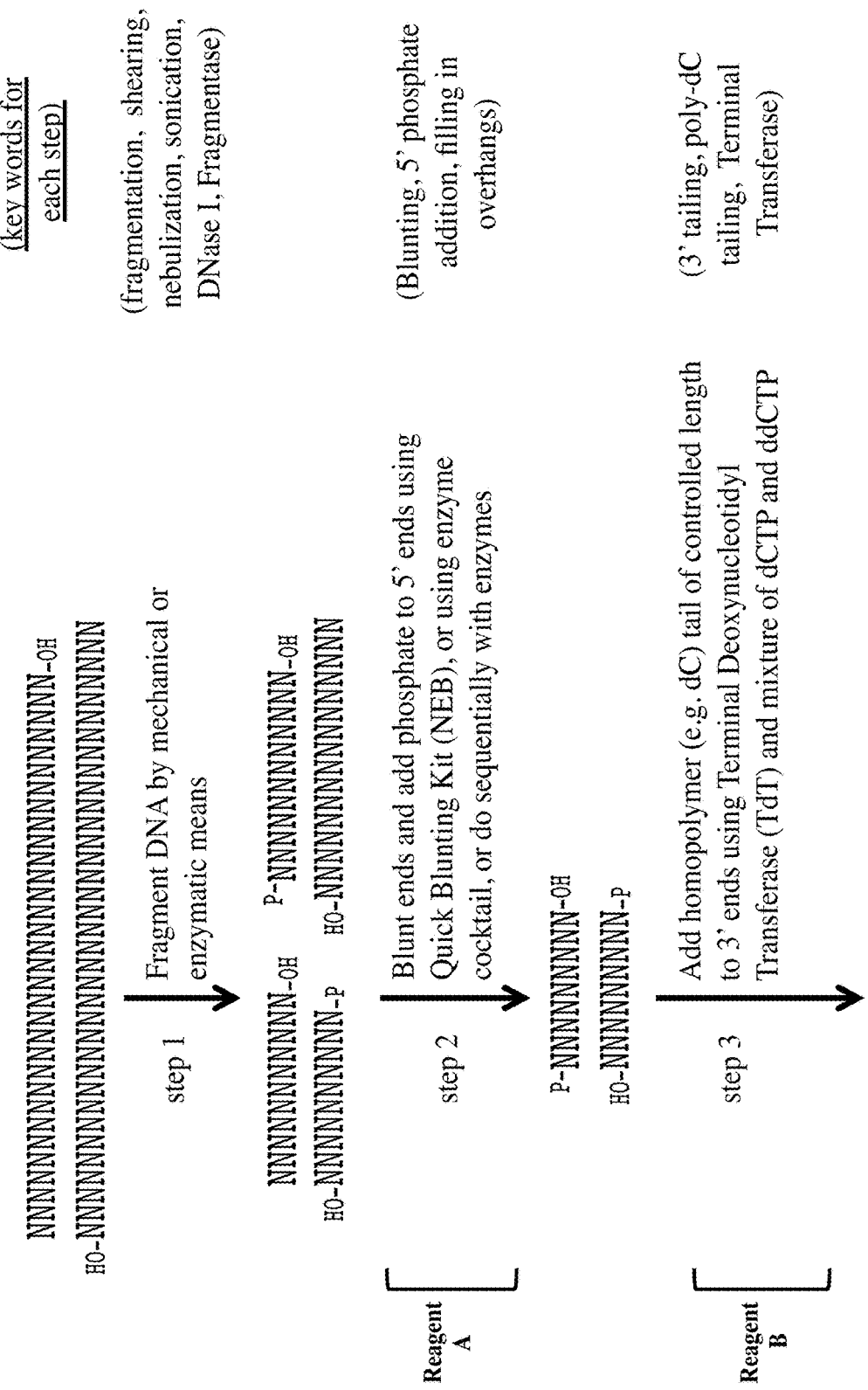

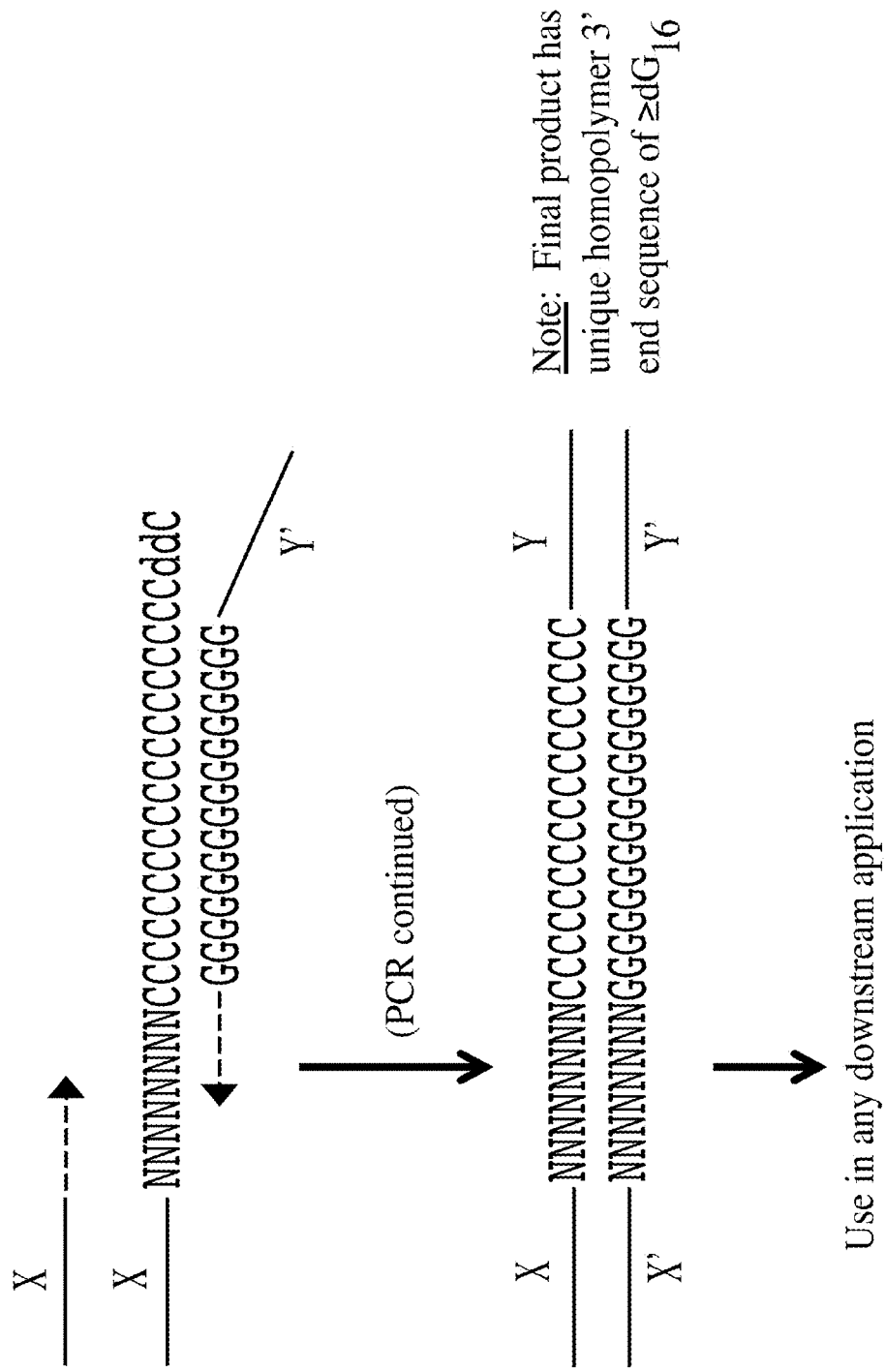

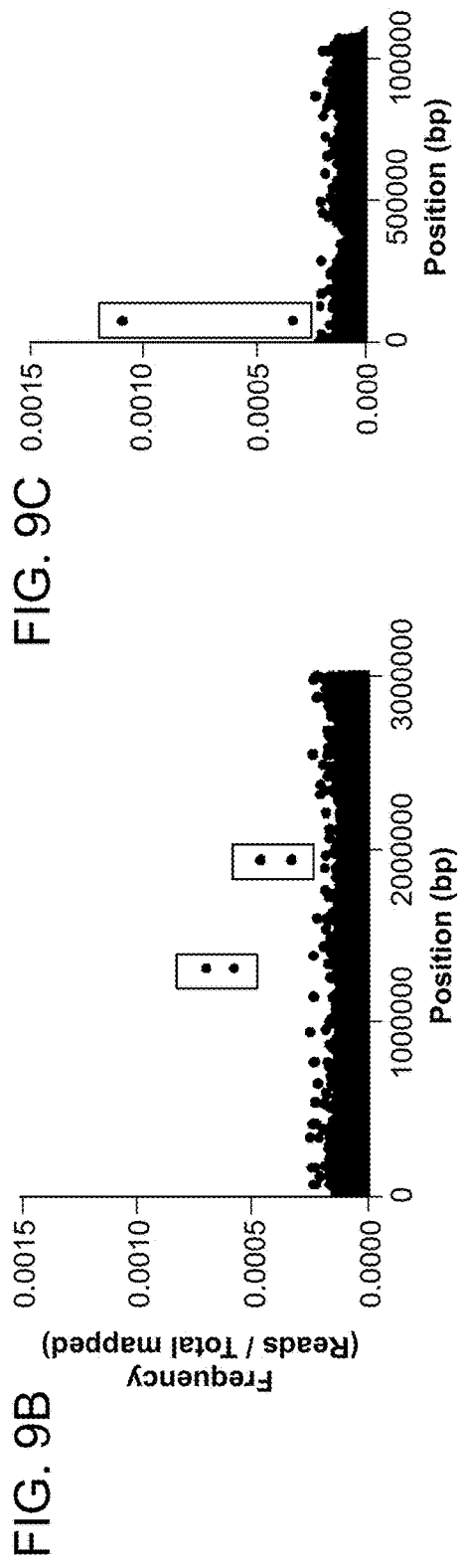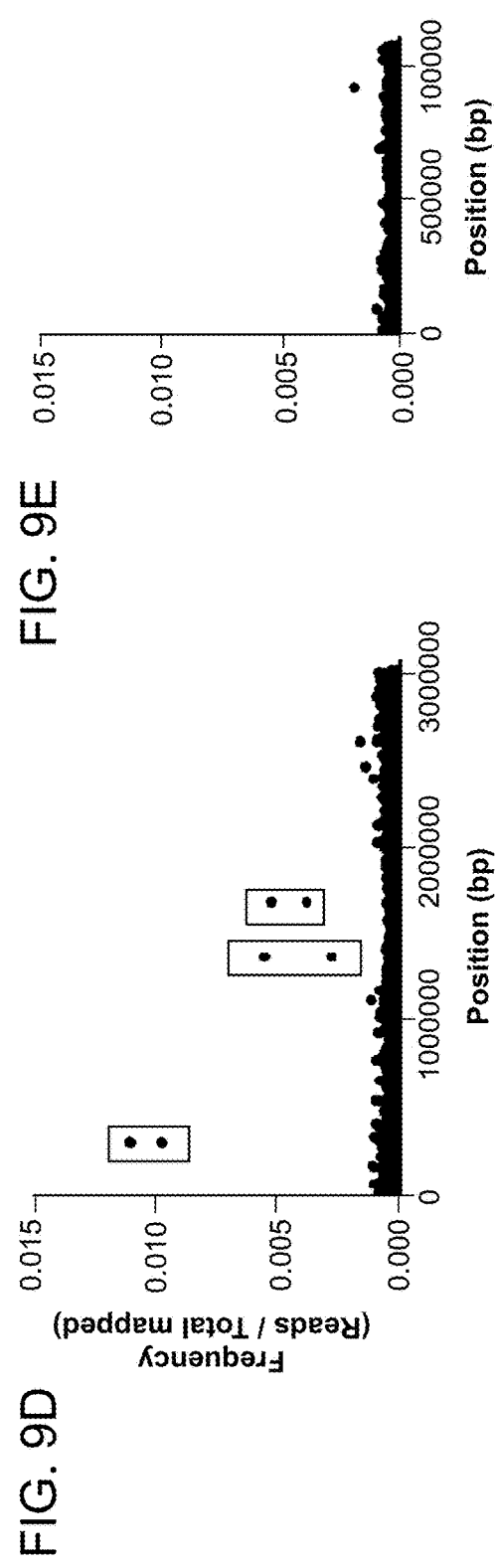

HOMOPOLYMER MEDIATED NUCLEIC ACID AMPLIFICATION

RELATED APPLICATIONS

This application is a national stage filing under 35 U.S.C. § 371 of international application number PCT/US2013/056383, filed Aug. 23, 2013, which was published under PCT Article 21(2) in English and claims the benefit under 35 U.S.C. § 119(e) of U.S. Provisional Application No. 61/692,502, filed Aug. 23, 2012, each of which is incorporated by reference herein in its entirety.

GOVERNMENT SUPPORT

This invention was made with government support under grant AI045746 awarded by National Institutes of Health. The government has certain rights in the invention.

FIELD OF THE INVENTION

Various aspects and embodiments of the invention relate to nucleic acid amplification technologies.

BACKGROUND OF INVENTION

The cloning of nucleic acid fragments as molecular libraries has become a core method used in many research, forensic and clinical settings. Current methods for molecular library construction require the ligation of double-stranded adapters of defined nucleotide sequence to the template nucleic acid ends followed by polymerase chain reaction (PCR) amplification (Bently, D. R et al. *Nature*, 2008, 456:53-59; Ranade, S. S. et al. *Analyt. Biochem.*, 2009, 390:126-135). Due, in part, to the poor efficiency of the adapter ligation reaction, these methods require large quantities of starting template nucleic acid which, in some instances, may be difficult to obtain. Moreover, existing methods are prone to producing adapter-dimers, which are inhibitory side products that necessitate the purification of the intended nucleic acid products by gel electrophoresis and extraction. Such purification requirements render existing amplification methods incompatible with high-throughput multiplexed robotic methods, thereby limiting the number of different libraries that can be created at one time.

SUMMARY OF THE INVENTION

Various aspects of the invention provide, inter alia, methods of amplifying nucleic acids and compositions comprising nucleic acids. Generally, the embodiments described herein relate to the use of homopolymer-mediated ligation to efficiently amplify nucleic acids of unknown, known or partially known sequence. The methods and compositions provided herein may be used together with existing nucleic acid technologies such as, for example, whole genome amplification, massive parallel sequencing library construction, and various other sequencing, cloning, in vitro transcription and microarray technologies.

Thus, in some aspects of the invention, provided herein are methods, comprising adding a first homopolymer of at least 12 nucleotides to each 3' end of blunt-ended double-stranded nucleic acid containing a target nucleic acid, thereby producing a partially double-stranded nucleic acid. In some embodiments, the following linear partially double-stranded nucleic acid product is produced:

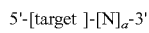

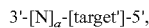

wherein
"target" is a nucleic acid,
"target'" is a nucleic acid complementary to "target",
"N" is a nucleotide, and
"a" is an integer greater than 11.

In some embodiments, the methods further comprise combining in a single reaction vessel the blunt-ended double-stranded nucleic acid, terminal deoxynucleotidyl transferase (TdT), deoxynucleotide triphosphate (dNTP), chain terminator, and buffer under conditions that permit polymerization, wherein the ratio of dNTP to chain terminator is at least 11 to 1.

In some embodiments, the methods further comprise adding a second homopolymer of at least 4 nucleotides to each 5' end of the partially double-stranded nucleic acid, wherein the second homopolymer is attached to a first oligonucleotide and is shorter than and complementary to the first homopolymer.

In some embodiments, the methods further comprise combining in a single reaction vessel the partially double-stranded nucleic acid, ligase, and the second homopolymer attached to the first oligonucleotide under conditions that permit ligation.

In some embodiments, the following linear partially double-stranded nucleic acid product is produced:

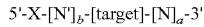

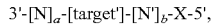

wherein
"N'" is a nucleotide complementary to "N",
"b" is an integer greater than 3, and
"X" is an oligonucleotide, and
"target", "target'", and "N" are as defined above.

In some embodiments, the following linear partially double-stranded nucleic acid product is produced:

wherein
"cT" is a chain terminator, and
"X", "N", "N'", "a", "b", "target" and "target'" are as defined above.

In some embodiments, the methods further comprise amplifying the target nucleic acid. In some embodiments, the target nucleic acid is amplified by polymerase chain reaction using a first primer and a second primer. In some embodiments, the first primer contains a second oligonucleotide that is the same as the first oligonucleotide; and the second primer contains, from 5' to 3', a third oligonucleotide different from the first and second oligonucleotides, and a fourth homopolymer complementary to the first homopolymer, wherein the fourth homopolymer is longer than the second homopolymer. In some embodiments, the first primer contains, from 5' to 3', the second oligonucleotide that is the same as the first oligonucleotide and a third homopolymer that is the same as the second homopolymer. In some embodiments, the fourth homopolymer contains at least 12 nucleotides.

In some embodiments, the following double-stranded nucleic acid product is produced:

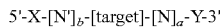

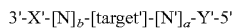

wherein
"X'" is an oligonucleotide complementary to "X",
"Y" is an oligonucleotide different from "X", and
"Y'" is an oligonucleotide complementary to "Y", and
"X", "N", "N'", "a", "b", "target" and "target'" are as defined above.

In some embodiments, the first homopolymer contains naturally occurring nucleotides or synthetic nucleotides. In some embodiments, the second homopolymer contains naturally occurring nucleotides or synthetic nucleotides. In some embodiments, the third homopolymer and the fourth homopolymer each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer is about 15 to about 30 nucleotides in length. In some embodiments, the third homopolymer is about 15 to about 30 nucleotides in length. In some embodiments, the second homopolymer is about 4 to about 8 nucleotides in length. In some embodiments, the fourth homopolymer is about 4 to about 8 nucleotides in length.

In some embodiments, the target nucleic acid is about 15 to about 15,000 nucleotides in length. In some embodiments, the target nucleic acid is about 100 to about 1000 nucleotides in length.

In some embodiments, the first oligonucleotide contains a restriction endonuclease recognition site (also referred to herein as a restriction enzyme recognition site), a recombination site, or a promoter for in vitro transcription. In some embodiments, the second oligonucleotide and the third oligonucleotide each contains a restriction endonuclease recognition site, a recombination site, or a promoter for in vitro transcription. In some embodiments, the recombination site is an attB, attP, lox or frt sequence. In some embodiments, the promoter is a T7, a T3, or an SP6 RNA polymerase recognition site.

In some embodiments, the chain terminator is a dideoxynucleotide (ddNTP). In some embodiments, the dideoxynucleotide is dideoxycytidine triphosphate (ddCTP), dideoxyguanosine triphosphate (ddGTP), dideoxyadenosine triphosphate (ddATP), or dideoxythymidine triphosphate (ddTTP). In some embodiments, the dideoxynucleotide is ddCTP or ddGTP.

In some embodiments, the ratio of dNTP to ddNTP in a single reaction is about 11 to 1 to about 29 to 1.

In some embodiments, the target nucleic acid is DNA.

In some embodiments, the sequence of the target nucleic acid is unknown, partially unknown, or known.

In other aspects of the invention, provided herein are methods, comprising (a) adding a first homopolymer of at least 12 nucleotides to each 3' end of blunt-ended double-stranded nucleic acid containing, from 5' to 3', a known target region contiguous with an unknown target region, thereby producing a first partially double-stranded nucleic acid; and (b) amplifying the known and unknown target regions by polymerase chain reaction using a first primer and a second primer, wherein the first primer contains, from 5' to 3', a first oligonucleotide and a second oligonucleotide that is the same as at least a portion of the known target region; and the second primer contains, from 5' to 3', a second oligonucleotide different from the first oligonucleotide, and a second homopolymer complementary to the first homopolymer.

In some embodiments, the following double-stranded nucleic acid product is produced:

5'-X-[known]-[unknown]-[N]$_a$-Y-3'

3'-X'-[known']-[unknown']-[N']$_a$-Y'-5', wherein
"X" is an oligonucleotide,
"X'" is an oligonucleotide complementary to "X",
"known" is a nucleic acid of known sequence,
"known'" is a nucleic acid complementary to "known",
"unknown" is a nucleic acid of unknown sequence,
"unknown'" is a nucleic acid complementary to "unknown",
"N" is a nucleotide, and
"N'" is a nucleotide complementary to "N",
"a" is an integer greater than 11.
"Y" is an oligonucleotide different from "X", and
"Y'" is an oligonucleotide complementary to "Y".

In some embodiments, (a) comprises combining in a single reaction vessel the blunt-ended double-stranded nucleic acid, terminal deoxynucleotidyl transferase (TdT), deoxynucleotide triphosphate (dNTP), chain terminator, and buffer under conditions that permit polymerization, wherein the ratio of dNTP to chain terminator is at least 11 to 1.

In some embodiments, the first homopolymer and the second homopolymer each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer and second homopolymer each is about 15 to about 30 nucleotides in length.

In some embodiments, the unknown target nucleic acid is about 15 to about 15,000 nucleotides in length. In some embodiments, the unknown target nucleic acid is about 100 to about 1000 nucleotides in length. In some embodiments, the known target nucleic acid contains about 15 to about 15,000 nucleotides.

In some embodiments, the first oligonucleotide and the second oligonucleotide each contains a restriction endonuclease recognition site, a recombination site, or a promoter for in vitro transcription. In some embodiments, the recombination site is an attB, attP, lox or frt sequence. In some embodiments, the promoter is a T7, a T3, or an SP6 RNA polymerase recognition site.

In some embodiments, the chain terminator is a dideoxynucleotide (ddNTP). In some embodiments, the dideoxynucleotide is dideoxycytidine triphosphate (ddCTP), dideoxyguanosine triphosphate (ddGTP), dideoxyadenosine triphosphate (ddATP), or dideoxythymidine triphosphate (ddTTP). In some embodiments, the dideoxynucleotide is ddCTP or ddGTP. In some embodiments, the ratio of dNTP to ddNTP is about 11 to 1 to about 29 to 1.

In some embodiments, the known target region contiguous with the unknown target region is prokaryotic DNA. In some embodiments, the known target nucleic acid contains an insertion sequence or transposon. In some embodiments, the known target region contiguous with the unknown target region is eukaryotic DNA. In some embodiments, the known target region is a transposon, retrotransposon or retrovirus, or repetitive element. In some embodiments, the known target region contiguous with the unknown target region is human DNA. In some embodiments, the known target region is a long interspersed nuclear element (LINE) or a short interspersed nuclear element (SINE). In some embodiments, the known target region contiguous with the unknown target region is viral DNA. In some embodiments, the known target region contiguous with the unknown target region is archael DNA.

In yet other aspects of the invention, provided herein are methods, comprising adding a first homopolymer of at least 12 nucleotides to the 3' end of a linear single-stranded nucleic acid containing a target nucleic acid, adding a first oligonucleotide to the 5' end of the linear single-stranded nucleic acid; and amplifying the target nucleic acid by polymerase chain reaction using a first primer and a second primer, wherein the first primer contains a second oligonucleotide that is the same as the first oligonucleotide; and the second primer contains, from 5' to 3', a third oligonucleotide different from the first oligonucleotide, and second homopolymer complementary to the first homopolymer.

In some embodiments, the following double-stranded nucleic acid product is produced:

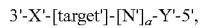

wherein
"X" is an oligonucleotide,
"X'" is an oligonucleotide complementary to "X",
"target" is a nucleic acid,
"target'" is a nucleic acid complementary to "target",
"N" is a nucleotide, and
"N'" is a nucleotide complementary to "N",
"a" is an integer greater than 11.
"Y" is an oligonucleotide different from "X", and
"Y'" is an oligonucleotide complementary to "Y".

In some embodiments, adding the first homopolymer of at least 12 nucleotides comprises combining in a single reaction vessel the linear single-stranded nucleic acid, terminal deoxynucleotidyl transferase (TdT), deoxynucleotide triphosphate (dNTP), chain terminator, and buffer under conditions that permit polymerization, wherein the ratio of dNTP to chain terminator is at least 11 to 1.

In some embodiments, adding the first oligonucleotide comprises combining in a single reaction vessel the linear single-stranded nucleic acid of (a), ligase, and the first oligonucleotide under conditions that permit ligation.

In some embodiments, the first homopolymer and the second homopolymer each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer and second homopolymer each is about 15 to about 30 nucleotides in length.

In some embodiments, the target nucleic acid is about 15 to about 15,000 nucleotides in length. In some embodiments, the target nucleic acid is about 100 to about 1000 nucleotides in length.

In some embodiments, the first oligonucleotide and second oligonucleotide each contains a restriction endonuclease recognition site, a recombination site, or a promoter for in vitro transcription. In some embodiments, the recombination site is an attB, attP, lox or frt sequence. In some embodiments, the promoter is a T7, a T3, or an SP6 RNA polymerase recognition site.

In some embodiments, the chain terminator is a dideoxynucleotide (ddNTP). In some embodiments, the dideoxynucleotide is dideoxycytidine triphosphate (ddCTP), dideoxyguanosine triphosphate (ddGTP), dideoxyadenosine triphosphate (ddATP), or dideoxythymidine triphosphate (ddTTP). In some embodiments, the dideoxynucleotide is ddCTP or ddGTP. In some embodiments, the ratio of dNTP to ddNTP is about 11 to 1 to about 29 to 1.

In some embodiments, the target nucleic acid is DNA or cDNA. In some embodiments, the DNA is partially degraded.

In various other aspects of the invention, provided herein are compositions comprising a linear double-stranded nucleic acid that comprises: a first single-stranded nucleic acid containing, from 5' to 3', a first oligonucleotide, a first homopolymer of at least 4 nucleotides, a target nucleic acid, a second homopolymer of at least 12 nucleotides that is longer than and complementary to the first homopolymer, and a second oligonucleotide different from the first oligonucleotide; and a second single-stranded nucleic acid complementary to the first single-stranded nucleic acid.

In some embodiments, the compositions comprise the following double-stranded nucleic acid product:

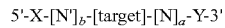

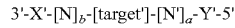

wherein
"X" is an oligonucleotide,
"X'" is an oligonucleotide complementary to "X",
"N" is a nucleotide, and
"N'" is a nucleotide complementary to "N",
"b" is an integer greater than 3.
"a" is an integer greater than 11.
"target" is a nucleic acid,
"target'" is a nucleic acid complementary to "target",
"Y" is an oligonucleotide different from "X", and
"Y'" is an oligonucleotide complementary to "Y".

In some embodiments, the first homopolymer and/or the second homopolymer contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer is about 4 to about 8 nucleotides in length. In some embodiments, the second homopolymer is about 15 to about 30 nucleotides in length.

In some embodiments, the target nucleic acid is about 15 to about 15,000 nucleotides in length. In some embodiments, the target nucleic acid is about 100 to about 1000 nucleotides in length.

In some embodiments, the first oligonucleotide and the second oligonucleotide each contains a restriction endonuclease recognition site, a recombination site, a promoter for in vitro transcription, or a polymerase chain reaction (PCR)

primer. In some embodiments, the recombination site is an attB, attP, lox or frt sequence. In some embodiments, the promoter is a T7, a T3, or an SP6 RNA polymerase recognition site.

In some embodiments, the target nucleic acid is DNA.

In some aspects of the invention, provided herein are compositions comprising a linear double-stranded nucleic acid that comprises: a first single-stranded nucleic acid containing, from 5' to 3', a first oligonucleotide, a target nucleic acid, a homopolymer of at least 12 nucleotides, and a second oligonucleotide different from the first oligonucleotide; and a second single-stranded nucleic acid complementary to and base-paired with the first single-stranded nucleic acid, wherein the first oligonucleotide and the second oligonucleotide each contains a restriction endonuclease recognition site, a recombination site, a promoter for in vitro transcription, or a polymerase chain reaction (PCR) primer.

In some embodiments, the compositions comprise the following double-stranded nucleic acid product:

wherein
"X" is an oligonucleotide,
"X'" is an oligonucleotide complementary to "X",
"target" is a nucleic acid,
"target'" is a nucleic acid complementary to "target",
"N" is a nucleotide, and
"N'" is a nucleotide complementary to "N",
"a" is an integer greater than 11.
"Y" is an oligonucleotide different from "X", and
"Y'" is an oligonucleotide complementary to "Y".

In some embodiments, the first homopolymer and/or the second homopolymer contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the homopolymer is about 15 to about 30 nucleotides in length. In some embodiments, the target nucleic acid is about 15 to about 15,000 nucleotides in length. In some embodiments, the target nucleic acid is about 100 to about 1000 nucleotides in length.

In some embodiments, the recombination site is an attB, attP, lox or frt sequence. In some embodiments, the promoter is a T7, a T3 or an SP6 RNA polymerase recognition site.

In some embodiments, the target nucleic acid is DNA.

In other aspects of the invention, provided herein are compositions comprising a linear partially double-stranded nucleic acid that comprises: (a) a first single-stranded nucleic acid containing from, 5' to 3', a target nucleic acid, a homopolymer of at least 12 nucleotides, and a chain terminator; and (b) a second single-stranded nucleic acid containing from, 5' to 3', a target nucleic acid complementary to and bound to the target nucleic acid of (a), a homopolymer of at least 12 nucleotides that is the same as the homopolymer of (a), and a chain terminator that is the same as the chain terminator of (a).

In some embodiments, the compositions comprise the following linear partially double-stranded nucleic acid product:

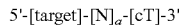

wherein
"target" is a nucleic acid,
"target'" is a nucleic acid complementary to "target",
"N" is a nucleotide, and
"N'" is a nucleotide complementary to "N",
"a" is an integer greater than 11, and
"cT" is a chain terminator.

In some embodiments, the homopolymer of (a) and the homopolymer of (b) each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the homopolymer of (a) and the homopolymer of (b) each is about 15 to about 30 nucleotides in length.

In some embodiments, the target nucleic acid of (a) and the target nucleic acid of (b) each is about 15 to about 15,000 nucleotides in length. In some embodiments, the target nucleic acid of (a) and the target nucleic acid of (b) each is about 100 to about 1000 nucleotides in length.

In some embodiments, the chain terminator of (a) and the chain terminator of (b) each is a dideoxynucleotide. In some embodiments, the dideoxynucleotide is dideoxycytidine monophosphate (ddCMP), dideoxyguanosine monophosphate (ddGMP), dideoxyadenosine monophosphate (ddAMP), or dideoxythymidine monophosphate (ddTMP). In some embodiments, the dideoxynucleotide is ddCMP or ddGMP.

In some embodiments, the target nucleic acid is DNA.

In other aspects of the invention, provided herein are compositions comprising a linear partially double-stranded nucleic acid that comprises: (a) a first single-stranded nucleic acid containing, from 5' to 3', an oligonucleotide, a first homopolymer of at least 4 nucleotides, a target nucleic acid, a second homopolymer of at least 12 nucleotides that is longer than and complementary to the first homopolymer, and a chain terminator; and (b) a second single-stranded nucleic acid containing, from 5' to 3', an oligonucleotide that is the same as the oligonucleotide of (a), a first homopolymer of at least 4 nucleotides that is the same as the first homopolymer of (a), a target nucleic acid that is complementary to and bound to the target nucleic acid of (a), a second homopolymer of at least 12 nucleotides that is the same as the second homopolymer of (a), and a chain terminator that is the same as the chain terminator of (a).

In some embodiments, the compositions comprise the following linear partially double-stranded nucleic acid product:

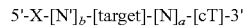

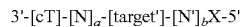

wherein
"X" is an oligonucleotide,
"target" is a nucleic acid,
"target'" is a nucleic acid complementary to "target",
"N" is a nucleotide, and
"N'" is a nucleotide complementary to "N",
"a" is an integer greater than 11,
"b" is an integer greater than 3, and
"cT" is a chain terminator.

In some embodiments, the first homopolymer of (a), the first homopolymer of (b), the second homopolymer of (a), and the second homopolymer of (b) each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer of (a) and the first homopolymer of (b) each is about 4 to about 8 nucleotides in length. In some embodiments, the second homopolymer of (a) and the second homopolymer of (b) each is about 15 to about 30 nucleotides in length.

In some embodiments, the target nucleic acid of (a) and the target nucleic acid of (b) each is about 15 to about 15,000 nucleotides in length. In some embodiments, the target nucleic acid of (a) and the target nucleic acid of (b) each is about 100 to about 1000 nucleotides in length.

In some embodiments, the oligonucleotide of (a) and the oligonucleotide of (b) each contains a restriction endonuclease recognition site, a recombination site, a promoter for in vitro transcription, or a PCR primer. In some embodiments, the recombination site is an attB, attP, lox or frt sequence. In some embodiments, the promoter is a T7, a T3 or an SP6 RNA polymerase recognition site.

In some embodiments, the chain terminator of (a) and the chain terminator of (b) each is a dideoxynucleotide. In some embodiments, the dideoxynucleotide is dideoxycytidine monophosphate (ddCMP), dideoxyguanosine monophosphate (ddGMP), dideoxyadenosine monophosphate (ddAMP), or dideoxythymidine monophosphate (ddTMP). In some embodiments, the dideoxynucleotide is ddCMP or ddGMP.

In some embodiments, the target nucleic acid of (a) and the target nucleic acid of (b) each is DNA.

In yet other aspects of the invention, provided herein are compositions comprising a linear partially double-stranded nucleic acid that comprises: (a) a first single-stranded nucleic acid containing, from 5' to 3', an oligonucleotide, a first homopolymer of at least 4 nucleotides, a target nucleic acid, and a second homopolymer of at least 12 nucleotides that is longer than and complementary to the first homopolymer; and (b) a second single-stranded nucleic acid containing from, 5' to 3', an oligonucleotide that is the same as the oligonucleotide of (a), a first homopolymer of at least 4 nucleotides that is the same as the first homopolymer of (a), a target nucleic acid that is complementary to and bound to the target nucleic acid of (a), and a second homopolymer of at least 12 nucleotides that is the same as the second homopolymer of (a).

In some embodiments, the compositions comprise the following linear partially double-stranded nucleic acid product:

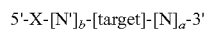

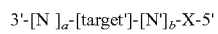

wherein
"X" is an oligonucleotide,
"target" is a nucleic acid,
"target'" is a nucleic acid complementary to "target",
"N" is a nucleotide, and
"N'" is a nucleotide complementary to "N",
"a" is an integer greater than 11, and
"b" is an integer greater than 3.

In some embodiments, the first homopolymer of (a), the first homopolymer of (b), the second homopolymer of (a), and the second homopolymer of (b) each contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the first homopolymer of (a) and the first homopolymer of (b) each is about 4 to about 8 nucleotides in length. In some embodiments, the second homopolymer of (a) and the second homopolymer of (b) each is about 15 to about 30 nucleotides in length.

In some embodiments, the target nucleic acid of (a) and the target nucleic acid of (b) each is about 15 to about 15,000 nucleotides in length. In some embodiments, the target nucleic acid of (a) and the target nucleic acid of (b) each is about 100 to about 1000 nucleotides in length.

In some embodiments, the oligonucleotide of (a) and the oligonucleotide of (b) each contains a restriction endonuclease recognition site, a recombination site, a promoter for in vitro transcription, or a PCR primer. In some embodiments, the recombination site is an attB, attP, lox or frt sequence. In some embodiments, the promoter is a T7, a T3, or an SP6 RNA polymerase recognition site.

In some embodiments, the target nucleic acid of (a) and the target nucleic acid of (b) each is DNA or cDNA.

In still other aspects of the invention, provided herein are compositions comprising a linear single-stranded nucleic acid that comprises, from 5' to 3', a target nucleic acid, a homopolymer of at least 12 nucleotides, and a chain terminator.

In some embodiments, the compositions comprise the following linear single-stranded nucleic acid product:

wherein
"target" is a nucleic acid,
"N" is a nucleotide, and
"a" is an integer greater than 11, and
"cT" is a chain terminator.

In some embodiments, the homopolymer contains naturally occurring nucleotides or synthetic nucleotides. In some embodiments, the naturally occurring nucleotides are selected from the group consisting of: cytosine nucleotides, guanine nucleotides, thymine nucleotides, adenine nucleotides and uracil nucleotides. In some embodiments, the naturally occurring nucleotides are cytosine nucleotides or guanine nucleotides. In some embodiments, the synthetic nucleotides are 2-amino-adenosine nucleotides.

In some embodiments, the homopolymer is about 15 to about 30 nucleotides in length.

In some embodiments, the target nucleic acid is about 15 to about 15,000 nucleotides in length. In some embodiments, the target nucleic acid is about 100 to about 1000 nucleotides in length.

In some embodiments, the chain terminator is a dideoxynucleotide. In some embodiments, the dideoxynucleotide is dideoxycytidine monophosphate (ddCMP), dideoxyguanosine monophosphate (ddGMP), dideoxyadenosine monophosphate (ddAMP), or dideoxythymidine monophosphate (ddTMP). In some embodiments, the dideoxynucleotide is ddCMP or ddGMP.

In some embodiments, the target nucleic acid of (a) and the target nucleic acid of (b) each is DNA.

BRIEF DESCRIPTION OF THE DRAWINGS

FIG. 7A: "Mwt"=molecular weight marker, "+"=positive control (gDNA from *E. coli*/pSAM_Bt); "−"=a negative control (*P. gingivalis* ATCC 33277). All other lanes contain amplicons from PCR of individual colonies of transformed *P. gingivalis*;

FIGS. 9A-9D provide images showing the identification of undermethylated Dam and VchM sites in *V. cholerae*; genomic DNA is shown as black lines, while the adaptor (tIL1) is shown in gray (FIG. 9A);

DETAILED DESCRIPTION OF THE INVENTION

In one aspect of the invention, provided herein are methods that include adding a first homopolymer of at least 12 nucleotides to each 3' end of blunt-ended double-stranded nucleic acid containing a target nucleic acid; adding a second homopolymer of at least 4 nucleotides to each 5' end of the partially double-stranded nucleic acid, wherein the second homopolymer is attached to a first oligonucleotide and is shorter than and complementary to the first homopolymer; and amplifying the target nucleic acid.

Figures 1, 2:
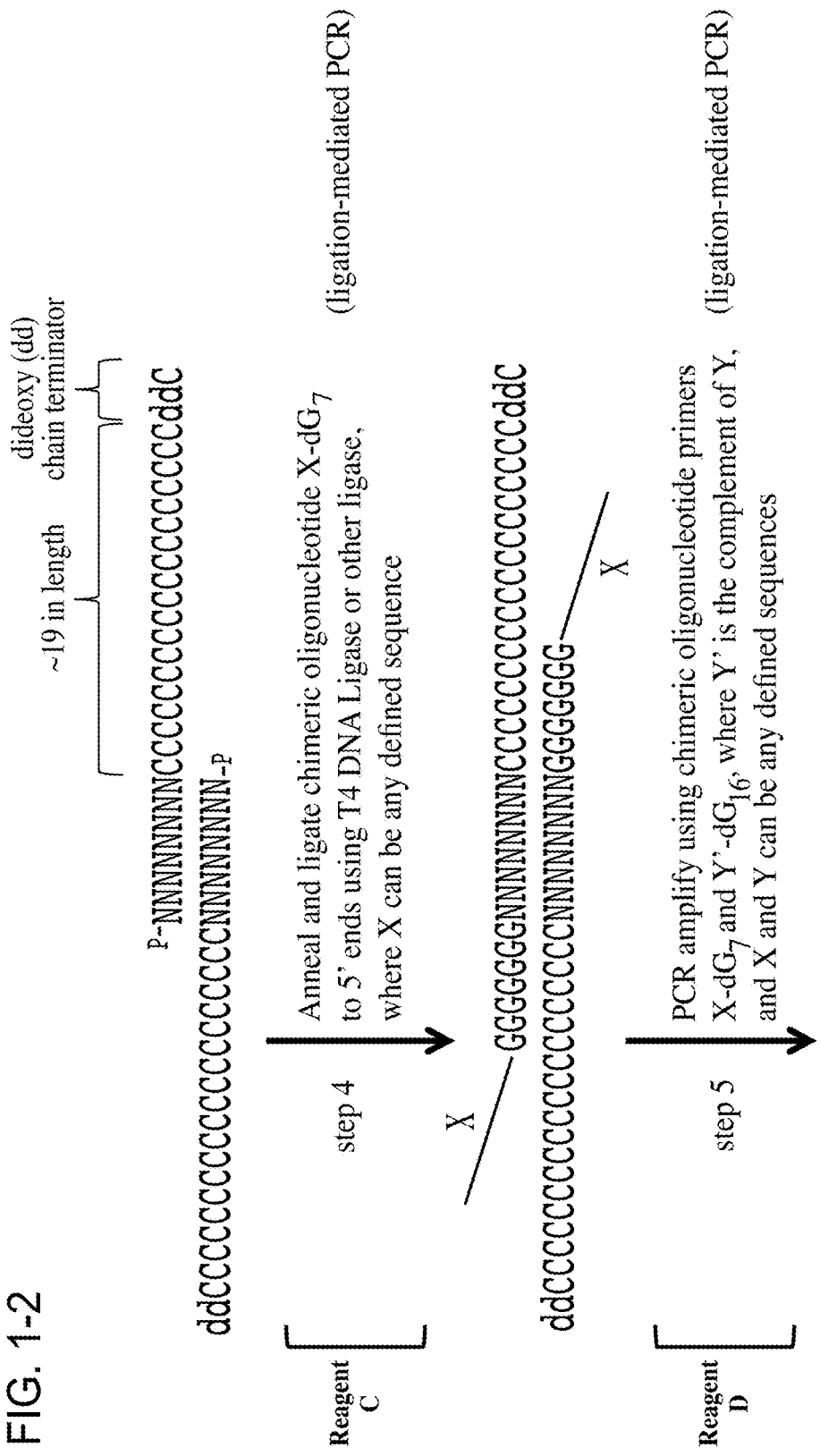
FIG. 1 provides a diagram of one embodiment of the methods provided herein.
FIG. 2 provides a diagram of one embodiment of the methods provided herein.

One example of a method according to this aspect of the invention is shown in FIG. 1. In Step 1, double-stranded nucleic acid is fragmented. In Step 2, the ends of the nucleic acid are blunted and phosphates are added to the 5' termini. In Step 3, a homopolymer is added to the 3' termini of the nucleic acid. In Step 4, a homopolymer linked to an oligonucleotide is added to the 5' termini of the nucleic acid through annealing and ligation. In Step 5, the nucleic acid is amplified by polymerase chain reaction (PCR). In this example, the method is applied to DNA molecules of unknown sequence and arbitrary length. For simplicity, only a single DNA fragment is shown after Step 2, and only the top strand (oriented 5' to 3') is shown after Step 4. Other DNA end structural types (e.g., 5' end or 3' end overhang types) may be present before and/or after Step 1. Annealed strands of DNA are shown aligned close to each other, whereas non-annealed DNA strands (e.g., those shown in Steps 4 and 5) are separated by a larger distance or indicated by an angled line. Abbreviations in FIG. 1 are, as follows: dC, deoxycytosine monophosphate; dCTP, 2'-deoxycytidine-5'-triphosphate; and ddCTP, 2',3'-dideoxycytidine-5'-triphosphate.

In another aspect of the invention, provided herein are methods that include adding a first homopolymer of at least 12 nucleotides to each 3' end of blunt-ended double-stranded nucleic acid containing, from 5' to 3', a known target region contiguous with an unknown target region, thereby producing a first partially double-stranded nucleic acid; and amplifying the known and unknown target regions by polymerase chain reaction using a first primer and a second primer, wherein the first primer contains, from 5' to 3', a first oligonucleotide and a second oligonucleotide that is the same as at least a portion of the known target region, and the second primer contains, from 5' to 3', a second oligonucleotide different from the first oligonucleotide, and a second homopolymer complementary to the first homopolymer.

One example of a method according to this aspect of the invention is shown in FIG. 2. In Step 1, double-stranded nucleic acid is fragmented, the ends of the nucleic acid are blunted, and phosphates are added to the 5' termini. In Step 2, a homopolymer is added to the 3' termini of the nucleic acid. In Step 3, the nucleic acid is amplified by PCR. In this example, the method is applied to DNA molecules of fused known and unknown sequences. "N" represents an unknown nucleotide, "D" represents the 5' region of the known sequence, and "E" represents the 3' region of the known sequence. "D," "E," and "N" are of arbitrary length. Note that "DDD" and "EEEEEEE" are not meant to represent repeat sequences per se, but essentially any known sequence. "D'" and "E'" represent the sequence complementary to "D" and "E". For simplicity, only a single DNA molecule is shown after Step 1, and only the top strand is shown after Step 3. Other abbreviations are as in FIG. 1.

In yet another aspect of the invention, provided herein are methods that include adding a first homopolymer of at least 12 nucleotides to the 3' end of a linear single-stranded nucleic acid containing a target nucleic acid, adding a first oligonucleotide to the 5' end of the linear single-stranded nucleic acid; and amplifying the target nucleic acid by polymerase chain reaction using a first primer and a second primer, wherein the first primer contains a second oligonucleotide that is the same as the first oligonucleotide, and the second primer contains, from 5' to 3', a third oligonucleotide different from the first oligonucleotide, and second homopolymer complementary to the first homopolymer.

Figures 1, 2, 3:
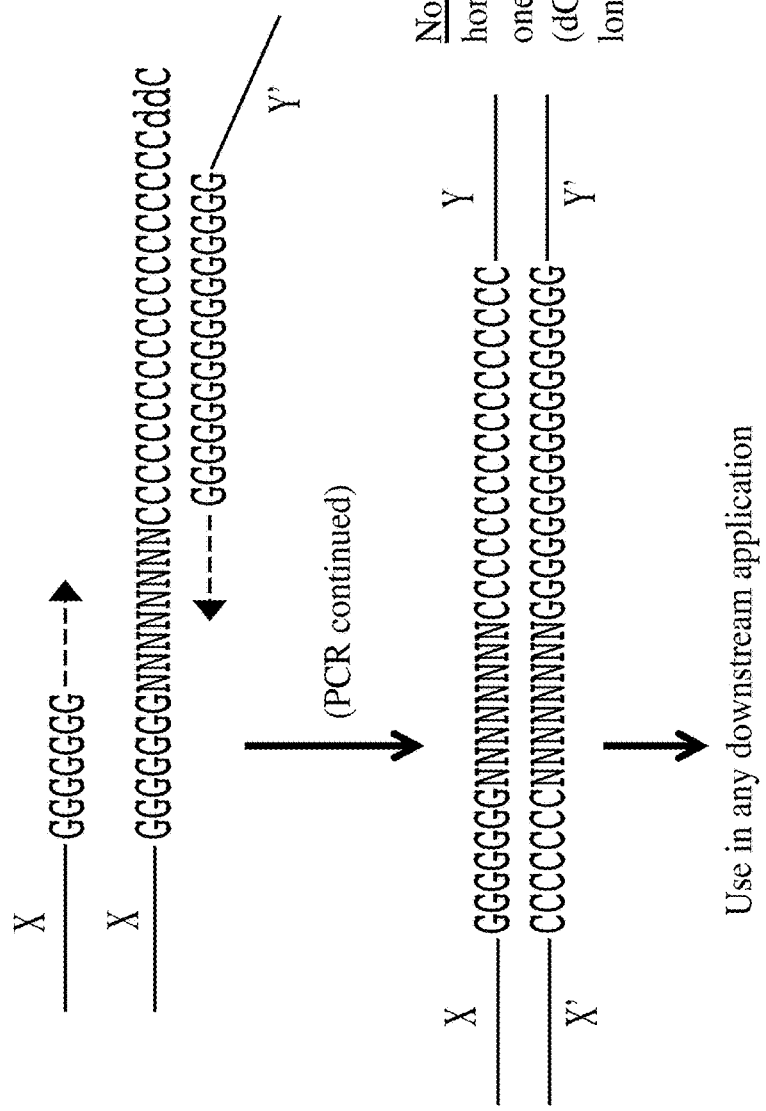
FIG. 3 provides a diagram of one embodiment of the methods provided herein.
Figures 1, 2:
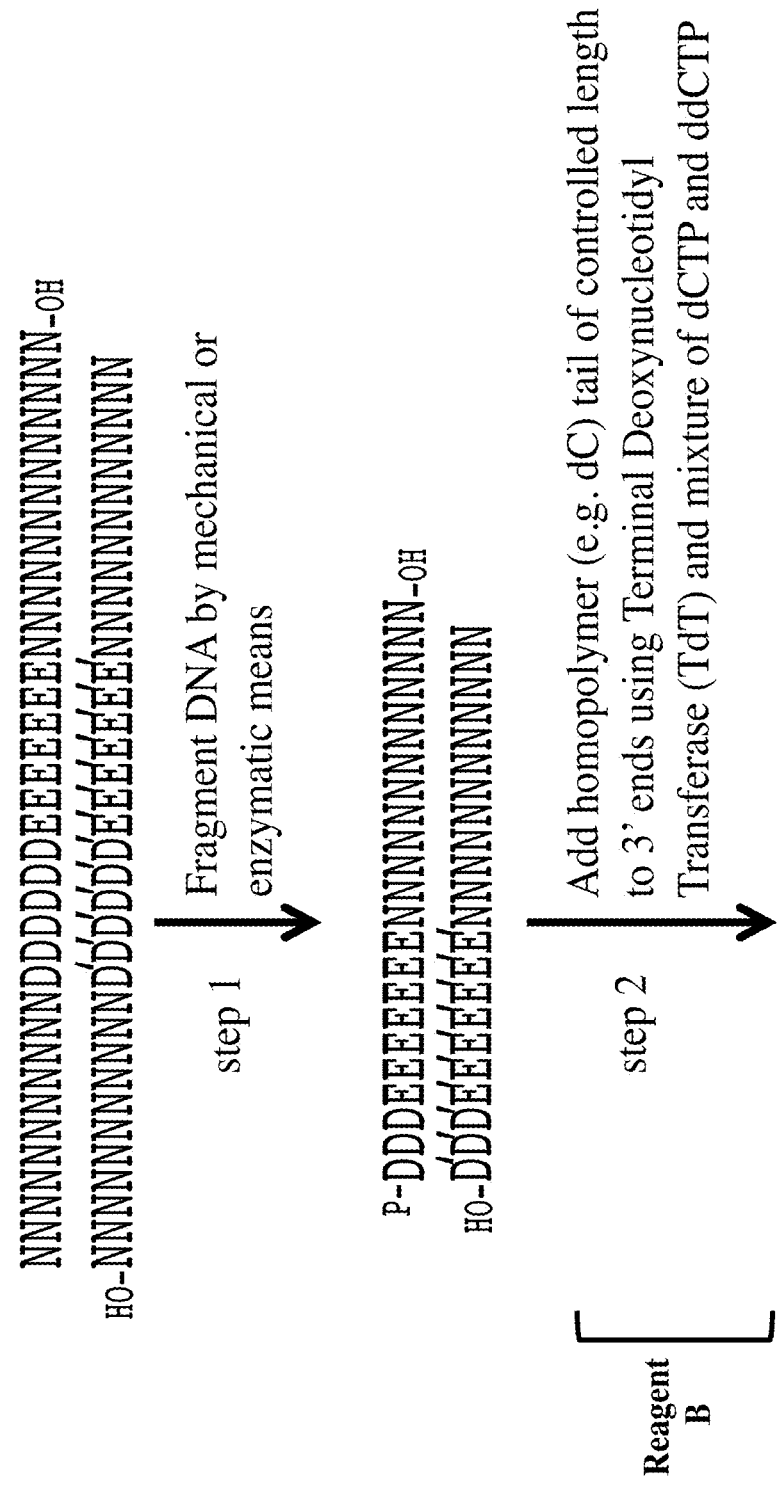
Figure 2:
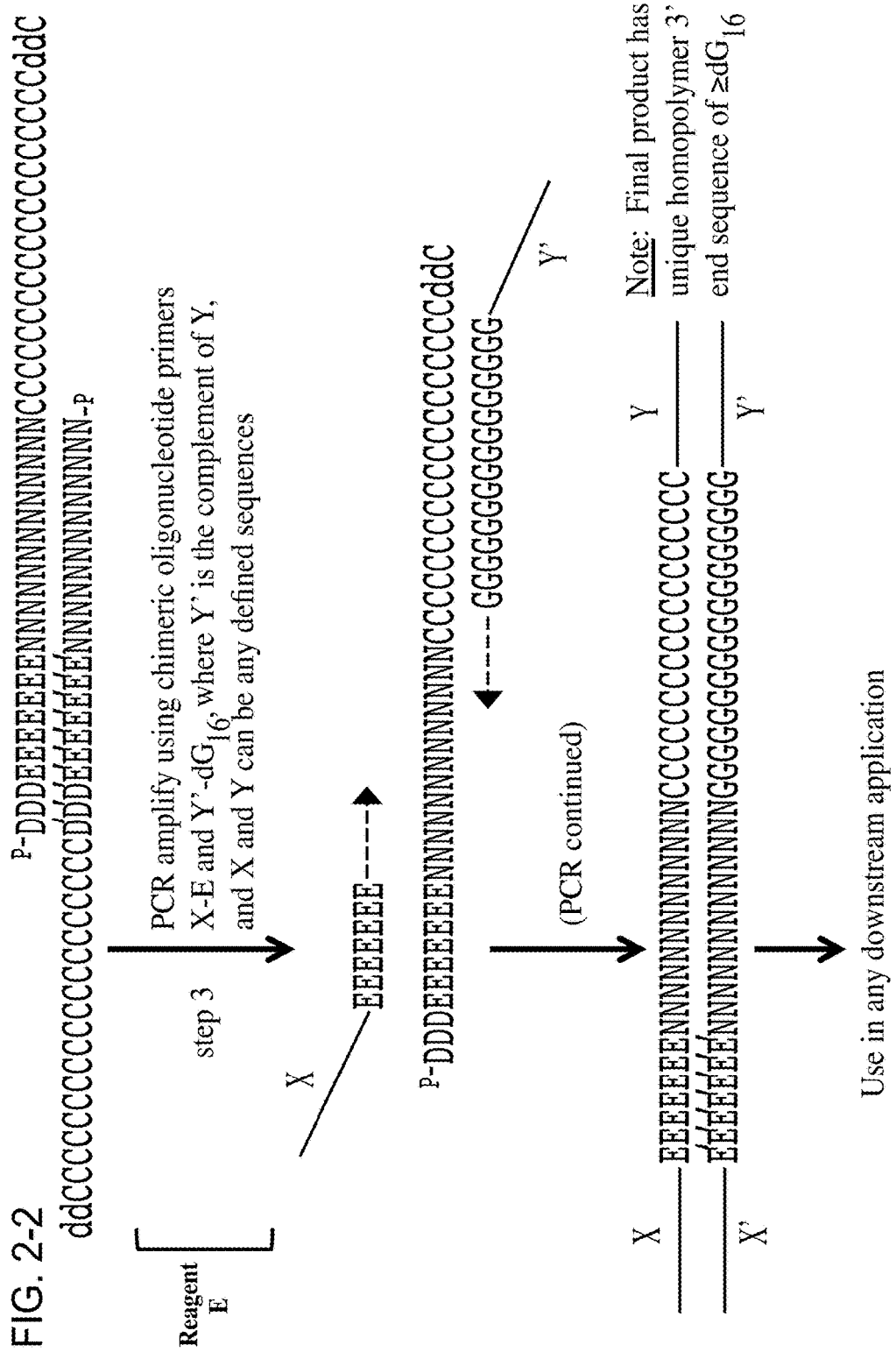
Figures 1, 3:
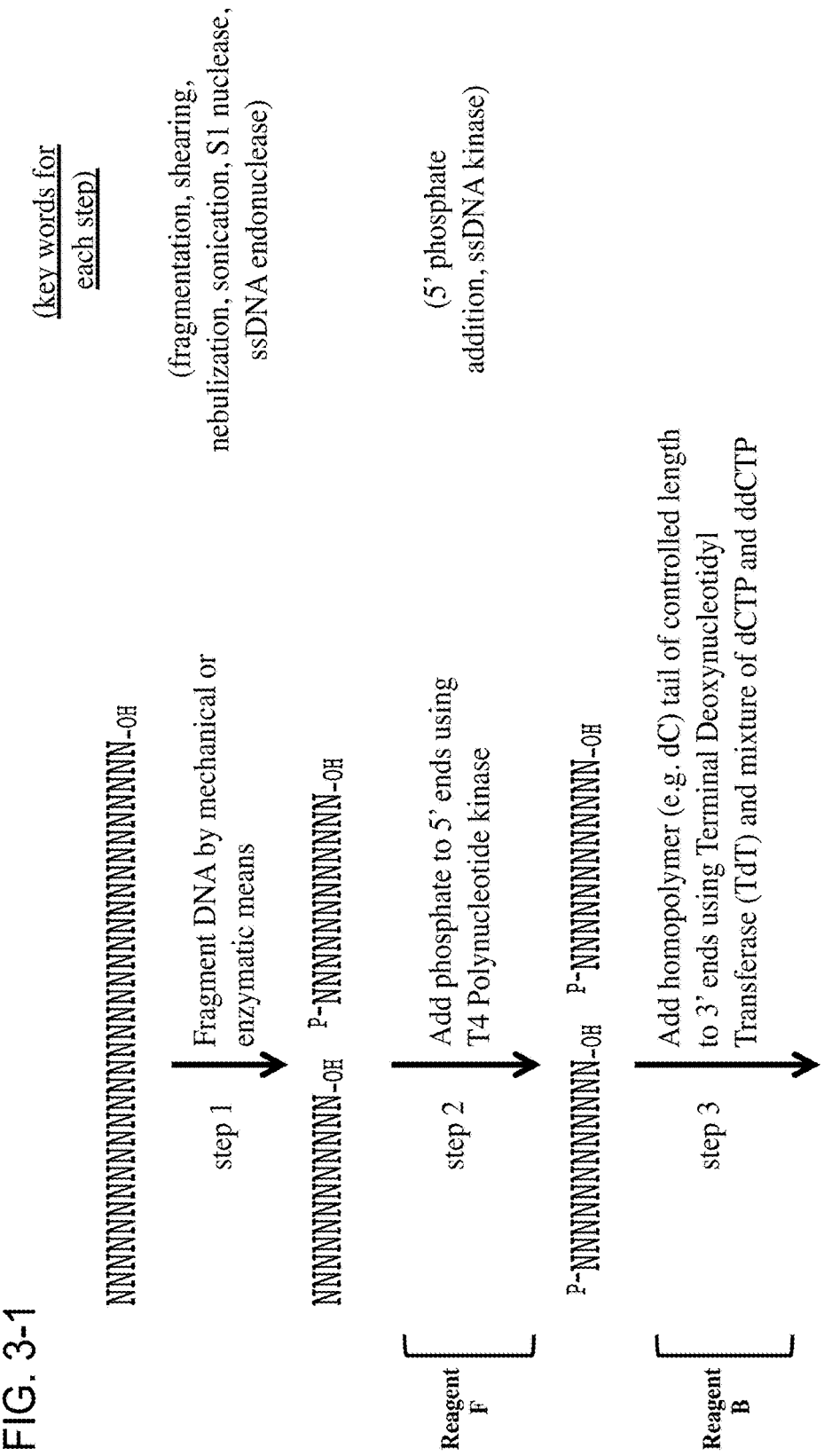
Figures 2, 3:
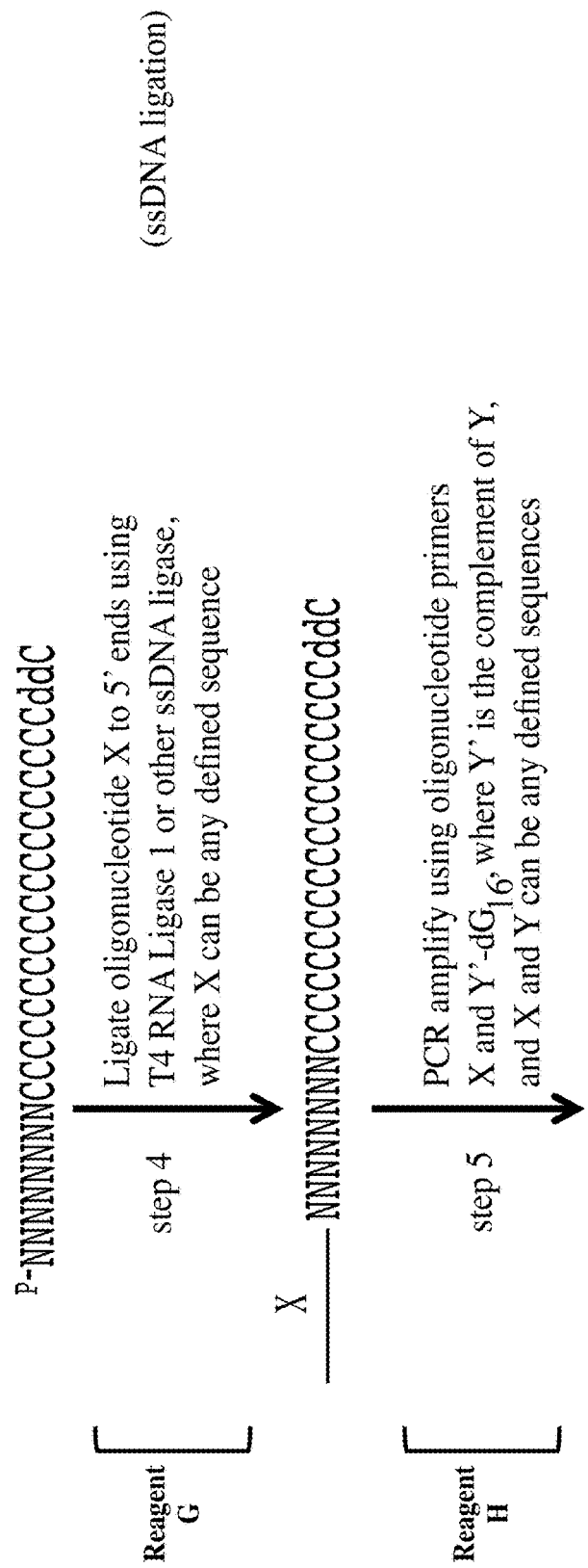

One example of a method according to this aspect of the invention is shown in FIG. 3. In Step 1, single-stranded nucleic acid is fragmented. In Step 2, phosphates are added to the 5' termini of the nucleic acid. In Step 3, a homopolymer is added to the 3' termini of the nucleic acid. In Step 4, a homopolymer linked to an oligonucleotide is added to the 5' termini of the DNA through ligation. In Step 5, the DNA is amplified by PCR. In this example, the method is applied to single-stranded DNA (ssDNA) of unknown sequence, "N," of arbitrary length. Abbreviations are the same as in FIG. 1.

In some embodiments, a nucleic acid may be single-stranded, double-stranded, or partially double-stranded. As used herein, a "nucleic acid" may refer to a single-stranded deoxyribonucleic acid (DNA), double-stranded or partially double-stranded DNA, single-stranded ribonucleic acid (RNA), and double-stranded or partially double-stranded RNA, as well as to forms of alternative nucleic acid containing modified bases, sugars, and backbones. Thus, the term "nucleic acid" may refer to cDNA, aptamers, peptide nucleic acids ("PNA"), 2'-5' DNA (e.g., a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). A nucleic acid may comprise, in some embodiments, a nucleic acid analogue, including known analogues of natural nucleotides that have similar or improved binding, hybridization or base-pairing properties. "Analogues" and analogous forms of purines and pyrimidines are well known in the art and include, without limitation, aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided herein include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, *Biochemistry*, 1997, 36:8692-8698), and benzylphosphonate linkages (see also Oligonucleotides and Analogues, A Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan, 1993, *J. Med. Chem.* 36:1923-1937; Antisense Research and Applications (1993, CRC Press).

The nucleic acids utilized herein may be any nucleic acid, for example, human nucleic acid, bacterial nucleic acid, or viral nucleic acid. The nucleic acids herein may be extracted from cells or synthetically prepared according to any means known to those skilled in the art. For example, the nucleic acids may be chemically synthesized or transcribed or reverse transcribed from cDNA or mRNA, among other sources. The nucleic acids may be, for example, nucleic acids from one or more cells, tissues, or bodily fluids. Nucleic acids may be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. Nucleic acids may also contain mixtures of material from one source or different sources. The nucleic acid may be intact nucleic acid such as, for example, genomic DNA that is purified, semi-purified or within cells; fragmented nucleic acid including, without limitation, ancient or otherwise partially degraded nucleic acid; a mixture of nucleic acid and other biological molecules and/or chemicals; or obtained from forensic DNA samples. The nucleic acid may be in solution, solid, desiccated or dehydrated, frozen, bound to a membrane or other surface, bound to particles or beads, bound to protein or other molecules, and/or stabilized with chemicals or compounds. Any of the nucleic acids described herein may be utilized according to the various aspects and embodiments of the invention.

Any amount or concentration of nucleic acid may be used in accordance with the various aspects and embodiments of the invention. In some embodiments, the amount of nucleic acid is about 10 picograms (pg) to about 1 microgram (μg), or more. In some embodiments, the amount of nucleic acid is less than 10 pg. In some embodiments, the amount of nucleic acid is about 10 pg to about 100 nanograms (ng). In some embodiments, the amount of nucleic acid is about 10 pg to about 100 pg, about 100 pg to about 1 ng, or about 1 ng to about μg. In some embodiments, the amount of nucleic acid is about 10 pg, about 20 pg, about 30 pg, about 40 pg, about 50 pg, about 60 pg, about 70 pg, about 80 pg, about 90 pg, about 100 pg, about 200 pg, about 300 pg, about 400 pg, about 500 pg, about 600 pg, about 700 pg, about 800 pg, or about 900 pg. In some embodiments, the amount of nucleic acid is about 1 ng, about 10 ng, about 20 ng, about 30 ng, about 40 ng, about 50 ng, about 60 ng, about 70 ng, about 80 ng, about 90 ng, about 100 ng, about 200 ng, about 300 ng, about 400 ng, about 500 ng, about 600 ng, about 700 ng, about 800 ng, or about 900 ng.

As used herein, a "target" nucleic acid may refer to a single-stranded nucleic acid or a double-stranded nucleic acid. A target nucleic acid is any nucleic acid of interest that, for example, is amplified by any of the methods described herein. In some embodiments, the target nucleic acid is about 15 to about 15,000 nucleotides in length, or longer. In some embodiments, the target nucleic acid is about 100 to about 10,000 nucleotides, about 100 to about 5,000 nucleotide, or about 100 to about 1000 nucleotides. In some embodiments, the target nucleic acid is about 15 to about 500 nucleotides, about 15 to about 400 nucleotides, about 15 to about 300 nucleotides, about 15 to about 200 nucleotide, about 15 to about 100 nucleotides, or about 15 to about 50 nucleotides.

A nucleic acid, as described herein, may comprise, in addition to a target nucleic acid, one or more elements such as, for example, one or more homopolymers, chain terminators, and/or one or more oligonucleotides.

As used herein, a "homopolymer" may refer to a polymer of nucleotides, each nucleotide the same. The nucleotides may be naturally occurring or synthetic. Naturally occurring nucleotides include cytosine nucleotides, guanine nucleotides, thymine nucleotides, adenine nucleotides or uracil nucleotides. Synthetic nucleotides include, without limitation, 2-amino-adenosine nucleotides. In some embodiments, a homopolymer may be comprised entirely of cytosine nucleotides, guanine nucleotides, thymine nucleotides, adenine nucleotides or uracil nucleotides. In some embodiments, a homopolymer may be comprised entirely of 2-amino-adenosine nucleotides. In some embodiments, use of thymine nucleotides, adenine nucleotides or uracil nucleotides may be avoided because of potentially unfavorable thermodynamics. In some embodiments, a homopolymer may not contain thymine nucleotides, adenine nucleotides, or uracil nucleotides.

In some embodiments, a homopolymer may be added to the 3' end of a single-stranded, double-stranded, or partially double-stranded nucleic acid. A homopolymer added to the 3' ends (3' termini) of DNA may be referred to herein as a 3' homopolymer. In some embodiments, the homopolymer addition may be achieved by ligation of a homopolymer to the nucleic acid, described elsewhere herein. In some embodiments, homopolymer addition may be achieved by polymerization. As used herein, "polymerization" refers to the assembly of monomers to form a linear molecule, in particular, the assembly of nucleotides (e.g., natural or synthetic) to form a nucleic acid. In some embodiments, polymerization of the homopolymers is achieved in a controlled manner. For example, homopolymer length may be controlled by limiting the concentration of the nucleotide in a polymerization reaction, or by limiting the time of the reaction. In other embodiments, a homopolymer may be added to the 3' end of a nucleic acid by combining in a single reaction vessel the nucleic acid, terminal deoxynucleotidyl transferase (TdT), deoxynucleotide triphosphate (dNTP), chain terminator, and buffer under conditions that permit polymerization. As used herein, a "chain terminator" may refer to any molecule, naturally occurring or synthetic, that terminates polymerization. The length of a homopolymer may be controlled by altering ratio of dNTP to chain terminator. For example, a homopolymer of about 12 nucleotides in length is achieved by combining a ratio of dNTP to chain terminator of about 11 to 1.

Examples of chain terminators include, without limitation, dideoxynucleotides such as, for example, dideoxycytidine monophosphate (ddCMP), dideoxyguanosine monophosphate (ddGMP), dideoxyadenosine monophosphate (ddAMP), and dideoxythymidine monophosphate (ddTMP). Other chain terminators may be used in the various aspects and embodiments provided herein. p In some embodiments, the 3' homopolymers may be greater than 9, greater than 10, or greater than 11 nucleotides in length. In some embodiments, the 3' homopolymers may be about 12 to about 100 nucleotides in length. In some embodiments, the 3' homopolymers may be about 12 to about 90, about 12 to about 80, about 12 to about 70, about 12 to about 60, about 12 to about 50, about 12 to about 40, about 12 to about 30, or about 12 to about 20 nucleotides in length. In some embodiments, the homopolymers may be about 12, about 13, about 14, about 15, about 16, about 17, about 18, about 19, or about 20 nucleotides in length. In some embodiments, the 3' homopolymers may be about 15 to about 50 nucleotides in length. In some embodiments, the 3' homopolymers may be about 15 to about 40, about 15 to about 30, or about 15 to about 20 nucleotides in length.

In some embodiments, a homopolymer may be added to the 5' ends of single-stranded, double-stranded or partially double-stranded nucleic acid. A homopolymer added to the 5' ends (5' termini) of DNA may be referred to herein as a 5' homopolymer. In some embodiments, a homopolymer may be added to the 5' ends of partially double-stranded nucleic acid. In some embodiments, the partially double-stranded nucleic acid has an existing 3' homopolymer (e.g., previously added by polymerization or ligation, as described herein) that is complementary to the 5' homopolymer. In some embodiments, the 5' homopolymer is added by ligation. The ligation reaction may be facilitated by annealing of the additional 5' homopolymer to the existing 3' homopolymer. In some embodiments, the 5' homopolymers may be greater than 2 or greater than 3 nucleotides in length. In some embodiments, the 5' homopolymers may be about 4 to about 100 nucleotides in length. In some embodiments, the 5' homopolymers may be about 4 to about 90, about 4 to about 80, about 4 to about 70, about 4 to about 60, about 4 to about 50, about 4 to about 40, about 4 to about 30, or about 4 to about 20 nucleotides in length. In some embodiments, the 5' homopolymers may be about 4, about 5, about 6, about 7, about 8, about 9, about 10, about 11, or about 12 nucleotides in length. In some embodiments, the 5' homopolymers added to the 5' ends of the nucleic acids may be shorter than the 3' homopolymers.

A homopolymer is "the same as" another homopolymer if the two homopolymers are comprised of the same nucleotides (all C, all G, all A, all T, or all U, see below) and are of the same length.

As used herein, a homopolymer "complementary" to another homopolymer refers to a homopolymer that contains nucleotides that base pair (e.g., bind to) nucleotides of another homopolymer. The length of the two homopolymers need not be equal to be "complementary." One homopolymer may be longer than its complementary homopolymer.

As used herein, an "oligonucleotide" (e.g., referred to herein, in some instances, as "X", "X'", "Y" or "Y'") may refer to any polymer of ten or more covalently bonded nucleotide monomers. In some embodiments, the oligonucleotides (e.g., any one or more) are shorter than the target nucleic acid. In some embodiments, the oligonucleotides are about 10 to about 100 nucleotides in length. In some embodiments, the oligonucleotides are about 10 to about 20, about 10 to about 30, about 10 to about 40, about 10 to about 50, about 10 to about 60, about 10 to about 70, about 10 to about 80, or about 10 to about 90 nucleotides in length. In some embodiments, the oligonucleotides are about 15 to about 30, about 15 to about 40, about 15 to about 50, about 15 to about 60, or about 15 to about 70 nucleotides in length. In some embodiments, the oligonucleotides are about 18 to about 30, or about 15 to about 20 nucleotides in length. A "chimeric oligonucleotide" may refer to an oligonucleotide (e.g., "X", "X'", "Y", or "Y'") attached (e.g., fused, linked, for example, covalently linked) to a homopolymer at its 3' end. The chimeric oligonucleotide may anneal anywhere along a homopolymer tail and prime the synthesis of a complementary strand from that position. Thus, nucleic acid products produced by the methods provided herein (e.g., products amplified by PCR) may have a homopolymer of variable length, but a length that may be equal to or greater than the homopolymer attached to the oligonucleotide (of the chimeric oligonucleotides). In FIG. 1, because chimeric oligonucleotide Y'-dC$_{16}$ annealed one base downstream in the 3' homopolymer, a homopolymer of 17 cytosine nucleotides is present at the 3' end of the PCR product. The presence of a variable length homopolymer at the 3' ends of the PCR products may serve as a sequence signature. This sequence signature is observed in the massive parallel sequencing (MPS) data obtained from the DNA of FIG. 4 and FIG. 5.

Figure 4:
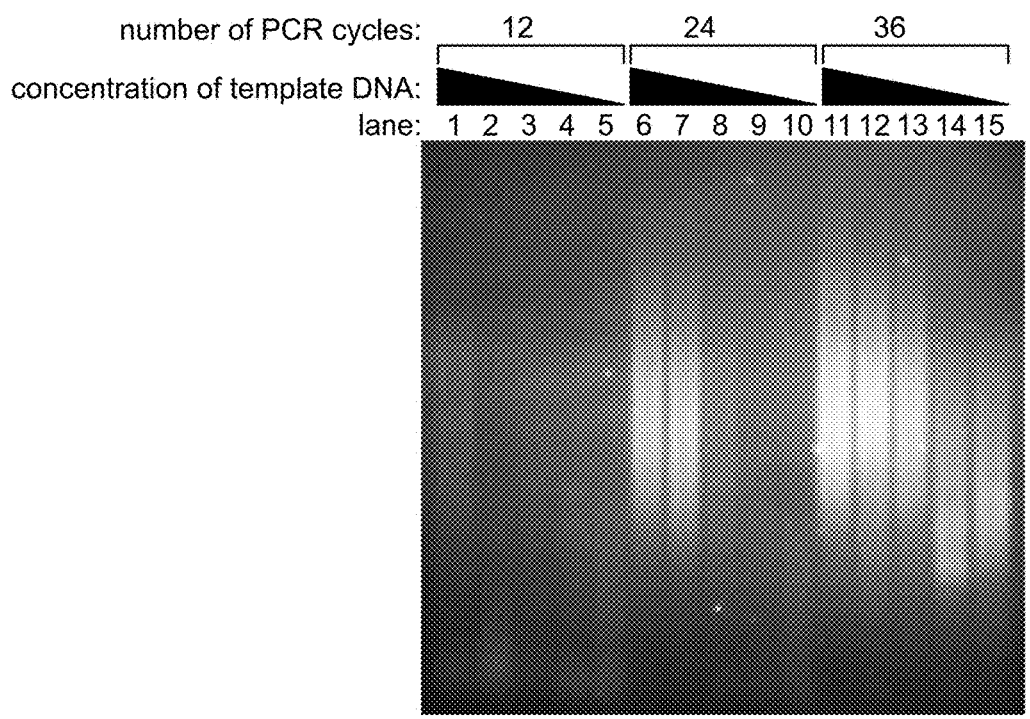
FIG. 4 provides an image of an electrophoretic gel showing PCR amplified *Vibrio cholera* genomic DNA.

FIG. 4 provides an image of an electrophoretic gel showing PCR amplified *Vibrio cholera* genomic DNA. Samples in lanes 1-5 were generated using 12 cycles, lanes 6-10 with 24 cycles, and lanes 11-15 with 36 cycles of PCR amplification. Decreasing amounts of input genomic DNA (gDNA) into the PCR reactions for lanes 1-5, 6-10 and 11-15 is indicated by the gradient triangles below the lane numbers: in lanes 1, 6 and 11, 100 nanograms (ng) of input gDNA was used; in lanes 2, 7 and 12, 10 ng of input gDNA was used; in lanes 3, 8 and 13, 1 ng of input gDNA was used; in lanes 4, 9, and 14, 100 picograms (pg) of input gDNA was used; and in lanes 5, 10 and 15, 10 pg of input gDNA was used. Lanes 1, 6, 7, 8, 11, 12, and 13 show products of lengths ranging from approximately 140-600 base pairs. Lanes 14 and 15 contain such products but also contain products of lower molecular weight not present in the other samples. These lower molecular weight species may result when the amount of input gDNA is very low and represent primer-dimers and other side-products that compete with the *Vibrio cholerae* library during amplification and subsequent sequencing reactions.

Figure 5:
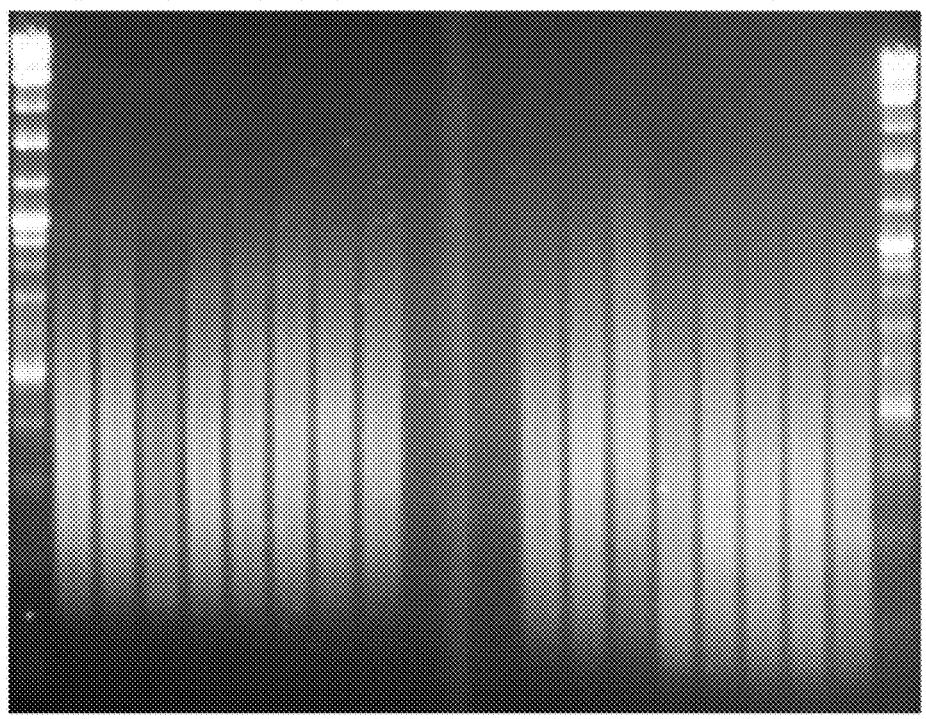
FIG. 5 provides an image of an electrophoretic gel showing PCR amplified transposon junctions in the *Staphylococcus aureus* genome harboring numerous transposon insertions.

FIG. 5 provides an image of an electrophoretic gel showing PCR amplified transposon junctions in the *Staphylococcus aureus* genome harboring numerous transposon insertions. Fourteen different bacterial transposon library cultures were individually grown in the presence of different sub-lethal concentrations of single antibiotics including daptomycin, linezolid, vancomycin, oxacillin, ciprofloxacin, clindamycin, chloramphenicol, gentamycin, tetracycline, rifampicin, and an experimental drug. Two control cultures grown in the absence of drug were also generated. DNA from the 16 cultures was subjected to the methods described herein. The resulting barcoded libraries (lanes 2-17) and the 2-Log DNA ladder (NEB; lanes 1 and 18) were resolved by 2% agarose gel electrophoresis and confirmed to be of the same size-ranges and concentrations.

Therefore, the presence of a homopolymer sequence at the 3' ends of the PCR products is consistent with of the methods provided herein.

An oligonucleotide that is "the same as" another oligonucleotide refers to an oligonucleotide that has the same nucleotide sequence and same nucleotide length as that of the other oligonucleotide. An oligonucleotide is different from another oligonucleotide if it does not have the same nucleotide sequence.

In some embodiments, the oligonucleotides include a restriction endonuclease recognition site (also referred to as a restriction site), a recombination site, a promoter for in vitro transcription, or a polymerase chain reaction (PCR) primer.

Examples of restriction endonuclease recognition sites include, without limitation, AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeI, BamHI, BanI, BanII, BbsI, BbvCI, BbvI, BccI, BceAI, BcgI, BciVI, BclI, BfaI, BfuAI, BfuCI, BglI, BglII, BlpI, Bme1580I, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, EcoNI, EcoO109I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I1, MspI, MwoI, NaeI, NarI, NciI, NcoI, NdeI, NgoMIV, NheI, NlaIII, NlaIV, NmeAIII, NotI, NruI, NsiI, NspI, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqI, TfiI, TliI, TseI, Tsp45I, Tsp509I, TspMI, TspRI, Tth111I, XbaI, XcmI, XhoI, XmaI, XmnI, and ZraI. Other restriction endonuclease recognition sites may be used in the various aspects and embodiments provided herein.

Examples of recombination sites include, without limitation, attB, attP, res, lox and frt sequences. Other recombination sites may be used in the various aspects and embodiments provided herein.

Examples of promoters for in vitro transcription include, without limitation, T7, T3 and SP6 RNA polymerase recognition sites. Other promoters for in vitro transcription may be used in the various aspects and embodiments provided herein.

Examples of commercial PCR primers include, without limitation, 3AOX1, 5AOX1, LIB M13F, LIB-M13R, MalE, M13F -24 mer, M13R-22 mer, OpIE2F, OpIE2R, pETBlueT7_up, pETBlue_down, pETBlue_up, pGEX forward, pGEX reverse, pIB FP, pIB RP, polyT20N, SP6, T3-17 mer, T3-20 mer, T7-17 mer, T7-20 mer, T7Term, and M13F 17-mer. Other PCR primers such as, for example, commercially-available primers may be used in the various aspects and embodiments provided herein. Examples of commercially-available primers include, without limitation, those used in Illumina®, SOLiD™, and 454 Life Sciences sequencing protocols, and those shown in Table I.

TABLE I

Genomic DNAn oligonucleotide sequences

Adapters
5' P-GATCGGAAGAGCTCGTATGCCGTCTTCTGCTTG (SEQ ID NO: 1)

5' ACACTCTTTCCCTACACGACGCTCTTCCGATCT (SEQ ID NO: 4)

PCR Primers
5' AATGATACGGCGACCACCGAGATCTACACTCTTTCCCTACACGACGCTCTTCCGATCT (SEQ ID NO: 2)

5' CAAGCAGAAGACGGCATACGAGCTCTTCCGATCT (SEQ ID NO: 3)

Genomic DNA Sequencing Primer
5' ACACTCTTTCCCTACACGACGCTCTTCCGATCT (SEQ ID NO: 4)

Multiplexing DNAn oligonucleotide sequences

Multiplexing Adapters
5' P-GATCGGAAGAGCACACGTCT (SEQ ID NO: 5)

5' ACACTCTTTCCCTACACGACGCTCTTCCGATCT (SEQ ID NO: 6)

TABLE I-continued

Multiplexing PCR Primer 1.0
5' AATGATACGGCGACCACCGAGATCTACACTCTTTCCCTACACGACGCTCTTCCGATCT
(SEQ ID NO: 7)

Multiplexing PCR Primer 2.0
5' GTGACTGGAGTTCAGACGTGTGCTCTTCCGATCT (SEQ ID NO: 8)

Multiplexing Read 1 Sequencing Primer
5' ACACTCTTTCCCTACACGACGCTCTTCCGATCT (SEQ ID NO: 9)

Multiplexing Index Read Sequencing Primer
5' GATCGGAAGAGCACACGTCTGAACTCCAGTCAC (SEQ ID NO: 10)

Multiplexing Read 2 Sequencing Primer
5' GTGACTGGAGTTCAGACGTGTGCTCTTCCGATCT (SEQ ID NO: 11)

PCR Primer Index 1
CAAGCAGAAGACGGCATACGAGATCGTGATGTGACTGGAGTTC (SEQ ID NO: 12)

PCR Primer Index 2
CAAGCAGAAGACGGCATACGAGATACATCGGTGACTGGAGTTC (SEQ ID NO: 13)

PCR Primer Index 3
CAAGCAGAAGACGGCATACGAGATGCCTAAGTGACTGGAGTTC (SEQ ID NO: 14)

PCR Primer Index 4
CAAGCAGAAGACGGCATACGAGATTGGTCAGTGACTGGAGTTC (SEQ ID NO: 15)

PCR Primer Index 5
CAAGCAGAAGACGGCATACGAGATCACTGTGTGACTGGAGTTC (SEQ ID NO: 16)

PCR Primer Index 6
CAAGCAGAAGACGGCATACGAGATATTGGCGTGACTGGAGTTC (SEQ ID NO: 17)

PCR Primer Index 7
CAAGCAGAAGACGGCATACGAGATGATCTGGTGACTGGAGTTC (SEQ ID NO: 18)

PCR Primer Index 8
CAAGCAGAAGACGGCATACGAGATTCAAGTGTGACTGGAGTTC (SEQ ID NO: 19)

PCR Primer Index 9
CAAGCAGAAGACGGCATACGAGATCTGATCGTGACTGGAGTTC (SEQ ID NO: 20)

PCR Primer Index 10
CAAGCAGAAGACGGCATACGAGATAAGCTAGTGACTGGAGTTC (SEQ ID NO: 21)

PCR Primer Index 11
CAAGCAGAAGACGGCATACGAGATGTAGCCGTGACTGGAGTTC (SEQ ID NO: 22)

PCR Primer Index 12
CAAGCAGAAGACGGCATACGAGATTACAAGGTGACTGGAGTTC (SEQ ID NO: 23)

Paired End DNAn oligonucleotide sequences

PE Adapters
5' P-GATCGGAAGAGCGGTTCAGCAGGAATGCCGAG (SEQ ID NO: 24)
5' ACACTCTTTCCCTACACGACGCTCTTCCGATCT (SEQ ID NO: 25)

PE PCR Primer 1.0
5' AATGATACGGCGACCACCGAGATCTACACTCTTTCCCTACACGACGCTCTTCCGATCT
(SEQ ID NO: 26)

DpnII gene expression oligonucleotide sequences

Gex Adapter 1
5' P-GATCGTCGGACTGTAGAACTCTGAAC (SEQ ID NO: 27)

5' ACAGGTTCAGAGTTCTACAGTCCGAC (SEQ ID NO: 28)

Gex Adapter 2
5' CAAGCAGAAGACGGCATACGANN (SEQ ID NO: 29)

5' P-TCGTATGCCGTCTTCTGCTTG (SEQ ID NO: 30)

Gex PCR Primer 1
5' CAAGCAGAAGACGGCATACGA (SEQ ID NO: 31)

Gex PCR Primer 2
5' AATGATACGGCGACCACCGACAGGTTCAGAGTTCTACAGTCCGA (SEQ ID NO: 32)

TABLE I-continued

```
Gex Sequencing Primer
5' CGACAGGTTCAGAGTTCTACAGTCCGACGATC (SEQ ID NO: 33)

NlaIII gene expression oligonucleotide sequences

Gex Adapter 1
5' P-TCGGACTGTAGAACTCTGAAC (SEQ ID NO: 34)

5' ACAGGTTCAGAGTTCTACAGTCCGACATG (SEQ ID NO: 35)

Gex Adapter 2
5' CAAGCAGAAGACGGCATACGANN (SEQ ID NO: 36)

5' P-TCGTATGCCGTCTTCTGCTTG (SEQ ID NO: 37)

Gex PCR Primer 1
5' CAAGCAGAAGACGGCATACGA (SEQ ID NO: 38)

Gex PCR Primer 2
5' AATGATACGGCGACCACCGACAGGTTCAGAGTTCTACAGTCCGA (SEQ ID NO: 39)

Gex Sequencing Primer
5' CCGACAGGTTCAGAGTTCTACAGTCCGACATG (SEQ ID NO: 40)

Small RNAn oligonucleotide sequences
RT Primer
5' CAAGCAGAAGACGGCATACGA (SEQ ID NO: 41)

5' RNA Adapter
5' GUUCAGAGUUCUACAGUCCGACGAUC (SEQ ID NO: 42)

3' RNA Adapter
5' P-UCGUAUGCCGUCUUCUGCUUGUidT (SEQ ID NO: 43)

Small RNA PCR Primer 1
5' CAAGCAGAAGACGGCATACGA (SEQ ID NO: 44)

Small RNA PCR Primer 2
5' AATGATACGGCGACCACCGACAGGTTCAGAGTTCTACAGTCCGA (SEQ ID NO: 45)

Small RNA Sequencing Primer
5' CGACAGGTTCAGAGTTCTACAGTCCGACGATC (SEQ ID NO: 46)
```

Oligonucleotide sequences ® 2006-2008 Illumina, Inc. All rights reserved.

In some embodiments, the single-stranded or double-stranded nucleic acid is fragmented. As used herein, "fragmentation" may refer to the separation of single-stranded or double-stranded nucleic acids into pieces/fragments. In some embodiments, the methods provided herein include the step of fragmentation, while in other embodiments, fragmented nucleic acids are provided or obtained as starting material. Fragmentation of nucleic acids may be achieved by various methods known in the art such as, for example, enzymatic methods and mechanical methods. The different methods of fragmentation may result in different end structures including blunt ends, 3' overhangs, 5' overhangs, 5' phosphates, lack of 5' phosphates, 3' hydroxyls (—OH), and lack of 3' hydroxyls.

Examples of enzymatic methods include, without limitation, cleavage by restriction endonucleases or other endonucleases such as deoxyribonuclease I (DNase I), and commercially-available endonucleases such as NEBNext® dsDNA Fragmentase® (New England Biolabs, U.S.A.). DNase I cleaves DNA preferentially at phosphodiester linkages adjacent to a pyrimidine nucleotide, yielding 5'-phosphate-terminated oligonucleotides with a free hydroxyl group on position 3', on average producing tetranucleotides. DNase I acts on single-stranded DNA (ssDNA), double-stranded DNA (dsDNA), and chromatin. NEBNext® dsDNA Fragmentase® generates dsDNA breaks in a time-dependent manner to yield 100-800 bp DNA fragments depending on reaction time. NEBNext® dsDNA Fragmentase® contains two enzymes, one randomly generates nicks on dsDNA, and the other recognizes the nicked site and cuts the opposite DNA strand across from the nick, producing dsDNA breaks. The resulting DNA fragments contain short overhangs, 5'-phosphates, and 3'-hydroxyl groups.

If the DNA sample is single-stranded (ssDNA), then enzymes that cleave double-stranded (dsDNA) are replaced with ones that cleave internal sites on ssDNA. Example enzymes that cleave ssDNA include, without limitation, restriction endonucleases that have ssDNA endonuclease activity, and Si nuclease. Other enzymatic and mechanical methods may also be used to fragment ssDNA.

Examples of mechanical methods include, without limitation, sonication and nebulization (e.g., Sambrook, J. and Russell, D. W. *Cold Spring Harbor Protoc.*, 2006, vol. 4), and passage through a small pore at high pressure.

The length of the DNA fragments may depend on the downstream application. For example, if the DNA will be amplified by PCR, then the DNA may be fragmented into a size range compatible with a PCR amplification protocol, which may be in the range of, for example, about 50 nucleotide to about 5,000 nucleotides. For preparation of a DNA library for subsequent massive parallel sequencing (MPS) on, for example, an Illumina® HiSeq2000 instrument, the DNA may be fragmented into a size range of about 100 nucleotides to about 600 nucleotides (see, e.g., manufacturer's instructions for Illumina® HiSeq2000). In some embodiments, the nucleic acids provided herein (e.g., single-stranded or double-stranded nucleic acids) are fragmented into pieces of about 15 to about 15,000 nucleotides (or nucleotide base pairs) in length. In some embodiments, the nucleic acids are fragmented into pieces of about 15 to about 10,000, about 15 to about 5,000, about 15 to about 2,500, about 15 to about 1000, or about 15 to about 500 nucleotides in length. In some embodiments, the nucleic acids are fragmented into pieces of about 50 to about 15,000, about 50 to about 10,000, about 50 to about 5,000, about 50 to about 2,500, about 50 to about 1000, or about 50 to about 500 nucleotides in length. In some embodiments, the nucleic acids are fragmented into pieces of about 100 to about 15,000, about 100 to about 10,000, about 100 to about 5,000, about 100 to about 2,500, about 100 to about 1000, or about 100 to about 500 nucleotides in length.

In some embodiments, the ends of double-stranded nucleic acids (or double-stranded nucleic acid fragments, used interchangeably herein) are blunted. As used herein, "blunted" nucleic acid or "blunt-ended" nucleic acid may refer to molecules that terminate in a base pair at both ends (i.e., at the 5' end and at the 3' end). Blunt-ended nucleic acids do not have unpaired nucleotides in the ends of the nucleic acid (e.g., 5' or 3' overhangs). Blunt ending of nucleic acids may be achieved by various methods known in the art including, without limitation, the use of protocols/kits that utilize T4 DNA polymerase (e.g., the Quick Blunting™ Kit, New England Biolabs, U.S.A.), the use of protocols that utilize Mung bean nuclease, and other commercially-available blunt ending kits. T4 DNA polymerase, as an example, has both 3'→5' exonuclease activity and 5'→3' polymerase activity. In some embodiments, the blunt-ended double-stranded nucleic acid is further phosphorylated at its 5' end to provide for subsequent ligation reactions. Blunt ending may be used to convert nucleic acid (e.g., DNA) with incompatible 5' or 3' overhangs to 5' phosphorylated, blunt-ended nucleic acid in a single reaction using, for example, the Quick Blunting™ Kit, which provides T4 kinase. Other means and kinases may be used to phosphorylate the 5' ends of blunt-ended double-stranded nucleic acid.

In some embodiments, after the DNA has been blunt ended, it may be necessary to remove excess deoxynucleotide triphosphates (dNTPs) so that they do not interfere with downstream applications, for example, addition of the 3' homopolymer. Removal of excess dNTPs may be achieved by various methods known in the art including, without limitation, gel filtration or size exclusion chromatography, nucleic acid precipitation, and nucleic acid purification using commercially available kits.

In some embodiments, a homopolymer may be added by ligation. As used herein, "ligation" may refer to the covalent linking of two ends of nucleic acids using, for example, a ligase. In some embodiments, a homopolymer is added to the 5' and/or 3' end of a single-stranded, double-stranded or partially double-stranded DNA molecules using DNA ligase (e.g., T4 DNA ligase, originating from T4 bacteriophage). DNA ligation involves creating a phosphodiester bond between the 3' hydroxyl of one nucleotide and the 5' phosphate of another. One molecule may contain a 5' phosphate for ligation, or the other molecule may be 5' pre-adenylated, in which case the ligation reaction may not require ATP. In some embodiments, a homopolymer is added to the 5' and/or 3' end of a single-stranded, double-stranded or partially double-stranded RNA molecules using RNA ligase. In some embodiments, a ligation reaction is carried out using nucleic acids that have blunt or compatible cohesive ends, buffer containing ATP (e.g., about 0.25 to about 1 mM), ligase (e.g., about 0.01 to about 1.0 unit or more, depending on the amount of nucleic acid), and water at a temperature of about 4° C., room temperature (e.g., about 25° C.), or about 14° C. to about 16° C. for about 30 minutes, a couple of hours, or overnight.

In some embodiments, the nucleic acids provided herein may be amplified by polymerase chain reaction (PCR) in combination with various techniques including, without limitation, DNA cloning for sequencing, DNA-based phylogeny, or functional analysis of genes, the diagnosis of hereditary diseases, the identification of genetic fingerprints (e.g., used in forensic sciences and paternity testing), the sequencing of ancient DNA recovered from frozen, mummified or otherwise preserved samples, and the detection and diagnosis of infectious diseases. An example of a basic PCR reaction includes a nucleic acid containing the target nucleic acid to be amplified, two primers that are complementary to the 3' ends of each of the sense and anti-sense strand of the nucleic acid target, polymerase (e.g., Taq polymerase), deoxynucleoside triphosphates (dNTPs), buffer, divalent cations (e.g., magnesium or manganese ions), and monovalent cation potassium ions. Generally, PCR includes a series of repeated temperature changes (i.e., "cycles"), as follows, though PCR is not limited to the following conditions:

Initialization step. This step may comprise heating the reaction to a temperature of about 94 to about 98° C., which may held for about 1 to about 9 minutes. This step is only used if thermostable polymerases are employed (see e.g., Sharkey, D. J., et al., *Bio/Technology*, 1994, 12 (5):506-509, incorporated by referene herein in its entirety).

Denaturation step. This step is typically the first regular cycling event and may comprise heating the reaction to about 94° C. to about 98° C. for about 20 to about 30 seconds. It causes melting of the DNA template by disrupting the hydrogen bonds between complementary bases, yielding single-stranded DNA.

Annealing step. The reaction temperature is lowered to about 50° C. to about 65° C. for about 20 to about 40 seconds, allowing annealing of the primers to the single-stranded DNA. The annealing temperature may be about 3-5° C. below the melting temperature of the primers used. Stable DNA-DNA hydrogen bonds are formed when the primer sequence very closely matches the template sequence. The polymerase binds to the primer-template hybrid and begins DNA formation.

Extension/elongation step. The temperature at this step depends on the DNA polymerase used. For example, Taq polymerase has its optimum activity temperature at about 75° C. to about 80° C. (see e.g., Chien A., et al., *J. Bacteriol*, 1976, 127 (3):1550-1557; Lawyer F., et al., *PCR methods and applications*, 1993, 2(4):275-287, each of which is incorporated by referene herein in its entirety), and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time may depend both on the DNA polymerase used and on the length of the DNA fragment to be amplified.

Final elongation. This step may be performed at a temperature of about 70° C. to about 74° C. for about 5 to about 15 minutes after the last PCR cycle to ensure that any remaining single-stranded DNA is fully extended.

Final hold. This step may be performed at about 4° C. to about 15° C. for any desired time and may be employed for short-term storage of the reaction.

In some embodiments, the methods and compositions provided herein are used in Whole Genome Amplification (WGA). Whole genome amplification generates microgram quantities of genomic DNA starting from a sample of as little as a few femtograms (see e.g., Hughes, S. and Lasken, R. S., *Whole Genome Amplification: Methods Express,* Scion Publishing Ltd., 2005)

In some embodiments, the methods and compositions provided herein are used in Massive Parallel Sequencing (MPS). Massive parallel sequencing encompasses several high-throughput approaches to DNA sequencing; it is also referred to as next generation sequencing (NGS) or second-generation sequencing. DNA sequencing with commercially available NGS platforms may be conducted with the following steps. First, DNA sequencing libraries may be generated by clonal amplification by PCR in vitro. Second, the DNA may be sequenced by synthesis, such that the DNA sequence is determined by the addition of nucleotides to the complementary strand rather through chain-termination chemistry. Third, the spatially segregated, amplified DNA templates may be sequenced simultaneously in a massively parallel fashion without the requirement for a physical separation step. While these steps are followed in most NGS platforms, each utilizes a different strategy (see e.g., Anderson, M. W. and Schrijver, I., 2010, *Genes,* 1: 38-69.). Examples of NGC platforms are shown in Table II.

TABLE II

| Platform | Template Preparation | Chemistry | Read length (bases) |
|---|---|---|---|
| Roche 454 | Clonal-emPCR | Pyrosequencing | 400‡ |
| GS FLX Titanium | Clonal-emPCR | Pyrosequencing | 400‡ |
| Illumina | Clonal Bridge Amplification | Reversible Dye Terminator | 35-100 |
| HiSeq 2000 | Clonal Bridge Amplification | Reversible Dye Terminator | 35-100 |
| Genom Analyzer IIX, IIE | Clonal Bridge Amplification | Reversible Dye Terminator | 35-100 |
| IScanSQ | Clonal Bridge Amplification | Reversible Dye Terminator | 35-75 |
| Life Technologies Solid 4 | Clonal-emPCR | Oligonucleotide Probe Ligation | 35-50 |
| Helicos Biosciences Heliscope | Single Molecule | Reversible Dye Terminator | 35‡ |
| Pacific Biosciences SMART | Single Molecule | Phospholinked Fluorescent Nucleotides | 800-1000 |

Additional uses for the compositions and methods provided herein are further described in the following references: Troy E. B., et al. *Infect Immun.,* 2013, 81(7):2347-57; Dalia, A. B. et al. *J Bacteriol.,* 2013, 195(10):2389-99; Seed, K. D. et al., *Nature,* 2013, 494(7438):489-91; Lazinski, D. W. and Camilli, A. *Biotechniques,* 2013, 54(1):25-34; Klein, B. A. et al., *BMC Genomics,* 2012, 31; 13:578, each of which is incorporated by reference herein).

EXAMPLES

Example 1

This Example demonstrates use of the methods provided herein for massively-parallel sequencing the Illumina® HiSeq™ 2000 Sequencing System. The method described in this Example is schematized, generally, in FIG. 1.

Step 1: Fragmentation of DNA. As discussed above, fragmentation of DNA provides DNA pieces (also referred to as fragments) of various lengths and end structures. First, double-stranded genomic DNA (gDNA) dissolved in a total volume of approximately 50-100 μl was put through a Performa DTR Gel Filtration Cartridge (Edge Bio), centrifuging at 900×g for 2 min, in order to remove any residual small molecules that might have carried over during the initial DNA purification. Then, 50-100 μl of the gDNA was fragmented by sonication in a 2 ml microcentrifuge tube (with a parabolic bottom) in a pre-chilled Branson High Intensity Cup Horn Sonifier for 2 minutes at 100% intensity with a 10 seconds ON/5 seconds OFF duty cycle. A small aliquot of the fragmented gDNA was run on a 2% agarose gel to confirm that most of the gDNA has been sheared to below 600 nucleotides in length.

Step 2: Blunt the ends of the DNA molecules and phosphorylate the 5' termini. The double-stranded gDNA used in this Example has blunt ends with 3' hydroxyls and 5' phosphates. The 3' hydroxyls are used for homopolymer addition in Step 3 below, and the 5' phosphates are used for the ligation in Step 4. The ends of the fragmented gDNA were blunted using the following reaction:

gDNA (1 ng-2 μg) from Step 1=15 μl
10× NEB Quick Blunting Kit buffer=2 μl
1 mM dNTPs=2 μl
NEB Quick Blunting Kit enzyme mix=1 μl The reaction was incubated at 20° C. for 60 minutes then heat inactivated at 75° C. for 30 minutes. Salt and excess deoxynucleotide triphosphates (dNTPs) were removed using a Performa DTR Gel Filtration.

Step 3: Add homopolymer to 3' termini. A homopolymer was added to the 3' termini of the gDNA using terminal deoxynucleotidyl transferase (TdT), a single dNTP, and a single dideoxynucleotide triphosphate (ddNTP) in a suitable buffer in the following reaction:

gDNA from Step 2=14.5 μl
9.5 mM dCTP/0.5 mM ddCTP=1 μl
5× TdT Promega reaction buffer=4 μl
TdT Promega enzyme=0.5 μl The above reaction proceeded at 37° C. for 1 hour, then was heat inactivated at 75° C. for 20 minutes. Salts, dCTP and ddCTP were removed using a Performa DTR Gel Filtration Cartridge.

Controlling the length of the homopolymer by addition of a ddNTP improved the overall efficiency in this Example. A 19:1 molar ratio of dCTP:ddCTP was used, which resulted in an average dC tail length of 20 nucleotides. This length is sufficient to anneal to the PCR reverse primer in Step 5. A longer homopolymer may, in some instances, be less efficient than a short one, because the complementary, shorter homopolymer attached to an oligonucleotide (e.g., primer) would have a larger region to "search" for proper annealing adjacent to the 5' phosphate for subsequent ligation. In addition, as described below in Step 5, the final PCR reaction requires annealing of a reverse primer to the homopolymer. If annealing occurs far downstream in a long homopolymer, then the final PCR product may contain a long homopolymer that may reduce, or possibly prevent, the ability to obtain useful sequence from that end of the molecule. Furthermore, this longer molecule may, in some instances, amplify less efficiently in Massive Parallel Sequencing (MPS) protocols (e.g., Illumina® HiSeq2000, SOLiD™ and 454 Life Sciences MPS platforms).

Step 4: Anneal and ligate chimeric oligonucleotide to 5' termini. A chimeric oligonucleotide having the structure "X-G$_7$" (olj1j623: 5'-AATGATACGGCGACCACCGAGA TCTACACTCTTTCCCTACACGACGCTCGGGGGGG-3'; SEQ ID NO:47) was annealed to the 3' homopolymer and subsequently ligated to the recessed 5' termini using T4 DNA ligase, as follows using the NEB Quick Ligation Kit:
  DNA from Step 4=9.5 µl
  NEB 2× Quick Ligation buffer=12.5 µl
  olj623 (30 µM)=2 µl
  NEB Quick Ligase Enzyme=1 µl The ligation reaction proceeded for 1 hour at room temperature. Primer olj623 is the Illuminal sequence (Illumina®) plus a $G_7$ homopolymer (homopolymer of 7 guanines) 3' extension. This provided for subsequent PCR amplification using X and Y containing primers and for MPS using Illumina® HiSeq2000 Sequencing System. The annealing of $X$-$G_7$ to the recessed 5' terminus greatly increased the efficiency of the subsequent ligation of this chimeric oligonucleotide to the 5' terminus. The length of the guanine homopolymer was optimal in the Example, though other lengths (e.g., four, five, and six nucleotides) also provided for efficient annealing at 20° C. to the 3' cytosine homopolymer, and subsequent ligation to the recessed 5' termini. In some instances, the 5' homopolymer may be shorter that the 3' homopolymer so as to avoid competition with the other chimeric primer (e.g., "Y'-$G_{16}$") of the PCR reaction (see e.g., FIG. 1), as this may yield nucleic acid products flanked on each end by X, instead of by X and Y.

A consideration for selecting homopolymer length and composition is whether or not endogenous homopolymer tracts in the starting DNA (e.g., DNA without synthetic homopolymers) will compete for PCR amplification or other downstream application. For example, use of a cytosine homopolymer (also referred to herein as a poly-C "tail") may not be optimal when applying this method to amplification of genomic DNA that contains numerous endogenous long poly-C tracts (e.g., long stretches of cytosine nucleotides). Nonetheless, in the majority of applications, the occurrence of such endogenous homopolymer tracts may not pose a problem. One may avoid this potential problem by using 2-amino-dATP for the homopolymer. Poly-2-amino-dA form three hydrogen bonds per base pair when annealing to poly-dT (thymidine homopolymer), which is ideal for annealing to a poly-dT-containing PCR reverse primer in Step 5. With an appropriate annealing temperature, a poly-dT-containing PCR reverse primer should not anneal to endogenous poly-dA or to any sequences in the sample DNA.

Step 5: PCR amplify DNA molecules. Finally, the DNA was then PCR amplified using primer olj623 and one of the five barcoded primers olj569-olj573 provided below. Each of these barcoded primers is an Illumina2 sequence (Illumina®) attached to a homopolymer of 16 guanines. The six base barcode is underlined. The barcodes provided for combining (multiplexing) separate samples together on a single lane on the HiSeq2000™ Sequencing System. The following PCR reaction was used:
  DNA=5 µ
  10 mM dNTPs=2 µl
  10× EasyA (Stratagene®) buffer=5 µl
  30 µM olj623=1 µl
  30 µM barcoded primer=1 µl
  pure water=35 µl
  Easy A enzyme (Stratagene®)=1 µl The reaction was heated to 95° C. for 2 minutes, then subjected to 12-36 cycles of the following:
  denaturation at 95° C. for 30 seconds;
  annealing at 65° C. for 30 seconds;
  extension at 72° C. for 120 seconds;
  an extra final extension at 72° C. for 120 seconds; and
  chilling at 4° C.

The number of cycles is dependent on the amount of DNA used in the PCR reaction. Also, because both olj623 and the barcoded primer are considered to be long, they are less efficient (than shorter primers) at PCR, thus more cycles were needed than for a standard PCR reaction. If it is desired (or necessary) to limit the number of cycles, so as to preserve higher original sample complexity, then three PCR reactions may be done per sample using, for example, 12, 24 and 36 cycles. Running a gel then allows for determination of the minimum number of cycles which may yield an amount of product sufficient for MPS.

The PCR products were then cleaned using the QIAquick® PCR Purification Kit (Qiagen) according to the manufacturer's instructions. The resulting DNA concentration was determined using the 2100 Bioanalyzer (Agilent), according to the manufacturer's instructions Finally, the PCR products were submitted for sequencing using the Illumina® HiSeg2000™ Sequencing System, according to the manufacturer's instructions using the custom sequencing primer, olj628 (5'-ACACTCTTTCCCTA-CACGACGCTCGGGGGGG-3') (SEQ ID NO:48) provided at 30 µM in pure water.

Barcoded primers (each is shown 5' to 3' with the barcode underlined):

olj569
(SEQ ID NO: 49)
CAAGCAGAAGACGGCATACGAGATAAAAAAGTGACTGGAGTTCAGACGTG

TGCTCTTCCGATCTGGGGGGGGGGGGGGG olj570
(SEQ ID NO: 50)
CAAGCAGAAGACGGCATACGAGATACACACGTGACTGGAGTTCAGACGTG

TGCTCTTCCGATCTGGGGGGGGGGGGGGG olj571
(SEQ ID NO: 51)
CAAGCAGAAGACGGCATACGAGATAGAGAGGTGACTGGAGTTCAGACGTG

TGCTCTTCCGATCTGGGGGGGGGGGGGGG olj572
(SEQ ID NO: 52)
CAAGCAGAAGACGGCATACGAGATATATATGTGACTGGAGTTCAGACGTG

TGCTCTTCCGATCTGGGGGGGGGGGGGGG olj573
(SEQ ID NO: 53)
CAAGCAGAAGACGGCATACGAGATCACACAGTGACTGGAGTTCAGACGTG

TGCTCTTCCGATCTGGGGGGGGGGGGGGG

Example 2

DNA was fragmented into a size range appropriate for the downstream application. The ends of the DNA were blunted and 5' ends were phosphorylated to provide for later ligation. A homopolymer (e.g., poly dC) of controlled length was added to the 3' termini using terminal deoxynucleotidyl transferase (TdT) and a mixture of deoxynucleoside triphosphate (e.g., dCTP) and chain-terminator (e.g., ddCTP). For homopolymer addition, an average length of 20 nucleotides was achieved by adjusting the ratio of deoxynucleotide to dideoxynucleotide to 19:1. After homopolymer addition, a polypeptide with a defined sequence, X, at its 5' end and 4-7 complementary deoxyguanosines (7 appeared to be optimal [data not shown]) at its 3' end was annealed to the homopolymer and joined to the 5' end of the opposing strand using T4 DNA ligase. Due to the stable nature of the seven dC:dG base-pairs, this ligation event was extremely efficient. The DNA was next amplified by PCR using the same oligonucleotide used for ligation as the forward primer, and a reverse primer composed of Y' at its 5' end and 16 complementary deoxyguanosines (dG) at its 3' end that are used to prime DNA synthesis from the homopolymer. The reverse primer can anneal to and prime from anywhere along the homopolymer. In the absence of a chain terminator, the homopolymer length generated can exceed hundreds of nucleotides (data not shown). By using ddCTP in the polymerization reaction, the contribution of poly dC to the final product was effectively limited. Although either titration of TdT or reduction of reaction time could also be used to limit tail length, the use of chain terminators in the context of excess enzymatic activity yielded the most precise and reproducible results (data not show).

In this Example, a method according to the invention was utilized in conjunction with massively parallel sequencing to determine the sequence of a previously un-sequenced bacterial strain, *V. cholerae* E7947. After fragmenting the genomic DNA by high intensity sonication, DNA concentrations over a range of four orders of magnitude (100-0.01 ng) were individually blunted, 5' end phosphorylated and treated with TdT in the presence of a 19:1 ratio of dCTP:ddCTP to generate 3' homopolymer tails averaging 20 nucleotides in length. The tailed substrate was then ligated to the chimeric oligonucleotide olj623, which has seven guanine nucleotides at its 3' end and the leftward sequences required for Illumina® sequencing at its 5' end. Finally, the products of this reaction were amplified by PCR using primers o1j623 and a barcode-containing primer that contains sixteen guanine nucleotides at its 3' end and the rightward sequence required for Illumina® sequencing at its 5' end. The reactions with 1-100 ng of input template yielded a range of product lengths from approximately 150-1000 bp (FIG. 4, lanes 1, 6-8 and 11-13). Twelve cycles of PCR were sufficient only for the highest amount (100 ng) of input genomic DNA (lane 1), while 24 cycles were sufficient for input amounts down to 1 ng (lanes 6-8). For the lowest input amounts (0.1 and 0.01 ng), visible products were only observed in the 36 cycle samples (lanes 14 and 15). The size range of the resulting products was distinctly lower than in the other lanes. MPS (see below) revealed that the products in lanes 14 and 15 were a mixture of bona fide *V. cholerae* sequences and unintended sequences derived from primers and contaminating human (possibly investigator) DNA.

Samples from lanes 11-15 were subjected to Illumina® sequencing and the resulting sequences were aligned to the complete genome sequence of a closely related *V. cholerae* reference strain, N16961 (3). Conventional Illumina® library preparation was also used to sequence E7946. When compared to the published sequence of the N16961 reference strain, the E7946 sequence contained 92 single-nucleotide polymorphisms (SNPs) and 100 deletion/insertion polymorphisms (DIPs), (Tables III and IV). For the samples in lanes 11-13, 96.8%, 94.6% and 68.1% of the raw unfiltered sequencing reads could be mapped to the N16961 reference genome, respectively. After filtering for quality, 99.7%, 99.1% and 89.5% of the respective reads were mapped to the reference sequence. All of the SNPs and DIPs observed with the conventional Illumina® library preparation were observed with the samples from lanes 11-13. In other words, the traditional method and this method provided herein yielded identical results; however, while 5 µg of genomic DNA were used to prepare the traditional library, 5,000 fold less DNA (1 ng; lane 13) was needed for preparation by the method provided herein. For the samples from lanes 14 and 15, even after the reads were filtered for quality, only 56.9% and 11.0% respectively were mapped to the N16961 genome. Still, there was sufficient data from each sample to cover greater than >99% of the E7946 genome and >90% of the SNPs were detected. Therefore, the method provided herein was at least partially successful down to 0.01 ng of input DNA, which is 100,000-500,000-fold less than that recommended by Illumina® for their method. As a point of reference, 0.01 ng DNA is the amount present in one and one-third human diploid cells.

Due to the 16 guanine nucleotides present at the 3' end of one of the PCR primers used, the genomic DNA can only be amplified if it contains a stretch of complementary cytosine nucleotides of a similar or greater length. In most molecules, the exogenously added cytosine homopolymer provides that requirement; however, if long cytosine (e.g., homopolymer) stretches exist naturally in the genome, these sites could be amplified in a tail-independent manner. Furthermore, because amplification of endogenous sites does not depend upon the efficiency of tailing, this amplification might be very efficient resulting in the over-representation of endogenous homopolymers in the final library. For this Example, this theoretical objection is not applicable as nowhere within the *V. cholerae* genome is there a cytosine stretch that exceeds 11 nucleotides in length (Heidelberg, J. F., et al., Nature, 2000, 406:477-484). Nonetheless, in larger more complex genomes such as the human genome, numerous endogenous cytosine stretches of at least 16 nucleotides do exist (International Human Genome Sequencing Consortium, Nature, 2001, 409:860-921; Venter, J. C., et al., Science, 2001, 291:1304-1351, each of which is incorporated by referene herein in its entirety).

Figure 6:
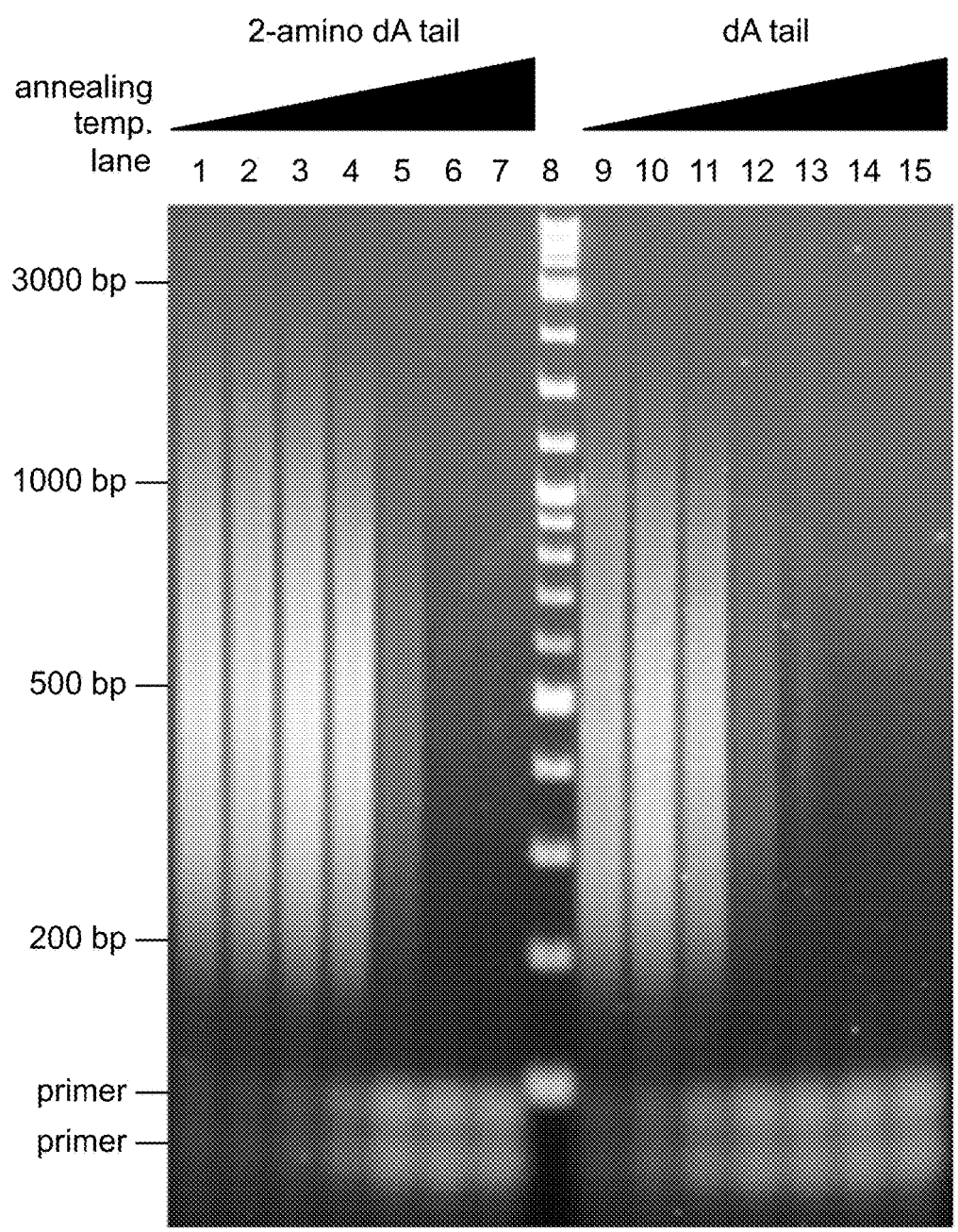
FIG. 6 provides an image of an electrophoretic gel showing PCR amplified products having different homopolymers, at different annealing temperatures.

To examined whether it was possible to modify the specifics of the homopolymer and PCR reactions to prevent the amplification of endogenous homopolymer sites, two different homopolymers were added to *V. cholerae* genomic DNA. While the dA:dT base pair involves only two hydrogen bonds, when the artificial base 2-amino deoxyadenosine (2-amino dA) pairs with dT, three hydrogen bonds can form (Howard, F. B, et al., J. Biol. Chem., 1966, 241:4293-4295; Rackwitz, H. R., et al., Eur. J. Biochem., 1976, 72:191-200; Scheit, K. H., et al., Nucl. Acids Res., 1982, 10:4059-4069; Cheong, C., et al., Nucl. Acids Res., 1988, 16:5115-5122, each of which is incorporated by referene herein in its entirety). It was hypothesized that if a tail composed of 2-amino dA was created, the added stability from pairing of this tail with an oligo dT primer could enable priming at PCR annealing temperatures where priming of the endogenous poly dA stretches would not occur. In the first case, an oligo dA homopolymer with a 30 nucleotide (nt) average length was added using TdT and a 29:1 ratio of dATP:ddATP. This tail was used as a surrogate for an endogenous dA stretch and was used to define the maximum annealing temperature at which oligo dT can prime from oligo dA. The second case was identical to the first except that 2-amino dATP was substituted. Each tailed substrate was first ligated to an oligonucleotide that has seven dT nucleotides at its 3' end and then subjected to PCR using this same oligonucleotide together with a second oligonucleotide that has 22 dT nucleotides at its 3' end. For each tailed substrate, seven different PCR annealing temperatures were tested and the results are shown in FIG. 6. The intensity of products generated with the 2-amino dA-tailed substrate at an annealing temperature of 62.4° C. was very similar to that obtained with the dA-tailed substrate at 58.3° C. (compare lanes 5 and 12), whereas no product was formed for the dA-tailed substrate at an annealing temperature of 62.4° C. (lane 13). Hence, the maximum allowed annealing temperature is increased by more than 4° C. when 2-amino dATP was substituted for dATP in the tailing reaction. The exogenously added poly dA sequence is chemically equivalent to an endogenous poly dA sequence that might naturally occur within a genome. By using 2-amino dATP in the polymerization (or "tailing") reaction and an annealing temperature of 62.4° C. during PCR, it was possible to prime from exogenous homopolymers without priming from endogenous ones.

Materials and Methods

DNA Fragmentation and Homopolymer Tail Addition

Genomic DNA was prepared from *Vibrio cholerae* strain E7946 using the Blood and Tissue kit (Qiagen). One microgram of E7946 DNA was brought to a total volume of 100 µl in pure water and put through a Performa DTR Gel Filtration Cartridge (Edge Biosystems) according to the manufacturer's instructions to remove any small molecules. The eluate was placed in a 2 mL microfuge tube and sheared to a size range of 100-800 bp in a pre-chilled (4° C.) Branson High Intensity Cup Horn Sonifier for 2 minutes at 100% intensity using a 10 seconds On and 5 seconds Off duty cycle. The DNA ends (100 ng, 10 ng, 1 ng, 0.1 ng or 0.01 ng of sheared template) were made blunt and 5' ends phosphorylated by treatment with the Quick Blunting kit (New England Biolabs) according to the manufacturer's directions, then heat-inactivated at 75° C. for 30 minutes. Small molecules were removed using a Performa DTR Gel Filtration Cartridge. A cytosine homopolymer tail of 20 nucleotide average length was added to the 3' ends of DNA by treatment with 0.5 µL Terminal deoxynucleotidyl transferase (Promega), 450 µM 2'-deoxycytidine 5'-triphosphate (dCTP), 50 µM 2',3'-dideoxycytidine 5'-triphosphate (ddCTP) and 1× TdT reaction buffer (Promega) at 37° C. for 1 hour. Alternatively, a homopolymer tail of 2-amino deoxyadenosine 5'-triphosphate was added to 100 ng of blunted template DNA using a 29:1 molar ratio of 2-amino dATP:ddATP (Trilink Biotechnologies) as above. The reactions were heat-inactivated at 75° C. for 30 minutes and small molecules were removed using a Performa DTR Gel Filtration Cartridge.

Oligonucleotide Ligation

The oligonucleotide olj623 (5'-AATGATACGGCGAC-CACCGAGATCTAC ACTCTTTCCCTACAC-GACGCTCGGGGGGG-3') (SEQ ID NO:82); leftward Illumina® sequence underlined) or olj682 (5'-AATGATACGGCGACCACCGAGATCTACAC TCTTTCCCTACACGACGCTCGGGTTTTTTT-3') (SEQ ID NO:83) was ligated to the 5' ends of the *V. cholerae* dC or 2-amino dA homopolymer tailed DNA samples, respectively, using the T4 DNA ligase (New England Biolabs) as follows: 24 µl of DNA, 2 µl of 30 µM oligonucleotide, 3 µl 10× T4 DNA Ligase buffer and 1 µl T4 DNA Ligase and incubated at room temperature for 1 hour. Small molecules were removed using a Performa DTR Gel Filtration Cartridge.

Amplification by PCR

The dC and 2-amino dA homopolymer tailed gDNA samples were amplified in single PCR reactions as follows: 28 µl DNA, 2 µl of 10 mM dNTPs, 5 µl 10× EasyA reaction buffer (Stratagene), 1 µl 30 µM forward primer, 1 µl 30 µM reverse primer, 12 µl water and 1 µl Easy A enzyme (Stratagene). For the dC-tailed sample, the primers were olj623 (above) and a barcoded primer of the form (5'-CAAGCAGAAGACGGCATACGAGATNNNNNNGT GACTGGAGTTCAGACGTGTGCTCTTC-CGATCTGGGGGGGGGGGGGGGG-3' (SEQ ID NO:84); where NNNNNN designates the reverse complement of the barcode used and the rightward Illumina® sequence is underlined) and the amplification conditions were as follows: 95° C. for 2 minutes; 12-36 cycles of 95° C. for 30 seconds, 65° C. for 30 seconds, 72° C. for 120 seconds; 72° C. for 120 seconds; 4° C. hold. For the 2-amino dA-tailed sample, the primers were olj682 (above) and olj684 (5'-CAAGCAGAAGACGGCATACGAGATCGTGAT GTGACTGGAGTTCAGACGTGTGCTCTTC-CGATCTTTTTTTTTTTTTTTTTTTTTT-3') (SEQ ID NO:85) and the amplification conditions were as follows: 95° C. for 2 minutes; 15 cycles of 95° C. for 30 seconds, one of seven different annealing temperatures (48° C., 52.1° C., 54.7° C., 58.3° C., 62.4° C., 65.7° C., or 68.4° C.) for 30 seconds, 72° C. for 120 seconds; 72° C. for 120 seconds; 4° C. hold.

DNA Sequencing and Data Analysis

The DNA was sequenced for 51 bases from a single-end using a HiSeq2000 (Illumina) with the custom sequencing primer: olj628 (5'-ACACTCTTTCCCTACAC-GACGCTCGGGGGGG-3') (SEQ ID NO:86). The resulting sequencing reads were manipulated and mapped to the reference genome using Genomics Workbench (CLC). Reads were filtered for quality using the "trim sequences" feature with the following input parameters: trim using quality scores limit=0.001, maximum number of ambiguities=0, discard reads below length=51. Next, filtered or unfiltered reads were used with the reference genome (accession numbers NC_002505, NC_002506, and AB374228) as input for the "map reads to reference" feature with the mismatch cost=1, limit=6, fast ungapped alignment unchecked, insertion cost=2, deletion cost=2, and global alignment checked. Finally, the single nucleotide polymorphism (SNP) and deletion/insertion polymorphism (DIP) detection features were used with *V. cholerae* reference assemblies and default input parameters except that the minimum coverage was set to 4 for both SNP and DIP detection while the minimum SNP variant frequency was set to 90% and the minimum DIP variant frequency was set to 70%.

Example 3

This Example demonstrates use of the methods provided herein for sequencing nucleic acids that have Mariner mini-transposon insertions within bacterial genomic DNA. The method described in this Example is schematized, generally, in FIG. 2.

The concentration of genomic DNA (gDNA) was confirmed to be at least 72 ng/µl Then, 50-100 µl of the gDNA was put through a Performa DTR Gel Filtration Cartridge in order to remove any residual small molecules that might have carried over during initial DNA purification.

Next, 50-100 µl of the gDNA was sonicated in a 2 ml microcentrifuge tube (with a parabolic bottom) in a pre-chilled Branson High Intensity Cup Horn Sonifier for 2 minutes at 100% intensity with a 10 seconds ON/5 seconds OFF duty cycle. A small aliquot was run on a 2% agarose gel to confirm that most of the DNA has been sheared to below 600 bp.

Cytosine homopolymers were added to the 3' ends using Terminal deoxynucleotidyl transferase (TdT) using the following reaction:

gDNA=14.5 µl
9.5 mM dCTP/0.5 mM ddCTP=1 µl
5× TdT Promega reaction buffer=4 µl
TdT enzyme (Promega)=0.5 µl The reaction proceeded at 37° C. for 1 hour, then heat inactivated at 75° C. for 20 minutes. Salts, dCTP and ddCTP were removed using a Performa DTR Gel Filtration Cartridge. The DNA was then PCR amplified using primer olj510 (5'-CCAAAATCCGTTCCTT TTTCATAGTTC-CTA-TATAGTTATACGC-3') (SEQ ID NO:54) and olj376 (5'-GTGACTGGAGTTCA GACGTGTGCTCTTCCG-ATCTGGGGGGGGGGGGGGGG-3') (SEQ ID NO:55). Primer olj510 is site-specific, annealing to a unique sequence within one end of the mini-Mariner transposon. Primer olj376 is specific for the cytosine homopolymers. With reference to FIG. 2, the known sequence, EEEEEEE, flanking the right junction of interest provides for a PCR priming site. "EEEEEEE" is not meant to indicate a repeat sequence, but instead indicates the sequence at the right end of the known region. The EEEEEEE sequence is a unique sequence of sufficient length to serve as a PCR primer. X and Y oligonucleotides may be any defined sequences. Inclusion of X and/or Y sequences in this step is optional. The PCR reaction may be done using chimeric primer pairs EEEEEEE/Y'-homopolymer, X-EEEEEEE/homopolymer, or EEEEEEE/homopolymer. Many applications may require the addition of X and Y sequences to the ends of the DNA molecules. In this Example, X and Y were specific for subsequent sequencing on the Illumina® HiSeg2000™ Sequencing System.

The following PCR reaction conditions were used:
DNA=5 µl
10 mM dNTP=2 µl
10× EasyA reaction buffer=5 µl
30 µM olj510=1 µl
30 µM olj376=3 µl
pure water=33 µl
Easy A enzyme (Stratagene®)=1 µl The reaction was heated at 95° C. for 2 minutes, followed by 24 cycles of the following:
denaturation at 95° C. for 30 seconds;
annealing at 60° C. for 30 seconds;
extension at 72° C. for 120 seconds;
an extra final extension at 72° C. for 120 seconds; and
chilling at 4° C.

A second PCR amplification reaction was performed using primer olj511 (5'-AATGATACGGCGACCACCGA-GATCTACACTCTTTGACCGGGGACTTATCAGCCA ACCTGTTA-3') (SEQ ID NO:56) and one of the 24 barcoded primers BC33-BC56 provided below. The purpose of this second PCR reaction was twofold: first, it used a nested mini-Mariner transposon primer (olj511) to provide added specificity, and second, it appended the sequences needed for Illumina® sequencing to the final product.

DNA from step 4=1 µl
10 mM dNTP=2 µl
10× EasyA reaction buffer=5 µl
30 µM olj511=1 µl
30 µM barcode primer=1 µl
pure water=39 µl
Easy A enzyme (Stratagene)=1 µl The reaction was heated to 95° C. for 2 minutes, then subjected to 10-15 cycles of the following:
denaturation at 95° C. for 30 seconds;
annealing at 60° C. for 30 seconds;
extension at 72° C. for 120 seconds;
an extra final extension at 72° C. for 120 seconds; and
chilling at 4° C.

A small aliquot of the PCR product was electrophoresed on a 2% agarose gel. The library DNA products comprised a broad band (smear) that started at 120 nucleotide base pairs and ran to greater than 600 nucleotide base pairs. The bulk of the signal was between 200-600 nucleotide base pairs. The library was cleaned using the QIAquick PCR Purification Kit (Qiagen), according to the manufacturer's instructions. The concentration of the library product was determined using the 2100 Bioanalyzer (Agilent), according to the manufacturer's instructions.

The products were submitted for sequencing on the Illumina® HiSeq2000 Sequencing System, according to the manufacturer's instructions using the custom sequencing primer olj512 (5'-ACACTCTTTGACCGGGGACT-TATCAGCCAACCTGTTA-3') (SEQ ID NO:57) provided at 30 µM in pure water.

Barcode primers (each is shown 5' to 3' with the barcode underlined; note that the resulting sequencing reads will contain the reverse complement of the barcodes shown):

BC33
(SEQ ID NO: 58)
CAAGCAGAAGACGGCATACGAGAT<u>CGTGAT</u>GTGACTGGAGTTCAGACGTG
TGCTCTTCCGATCT

BC34
(SEQ ID NO: 59)
CAAGCAGAAGACGGCATACGAGAT<u>ACATCG</u>GTGACTGGAGTTCAGACGTG
TGCTCTTCCGATCT

BC35
(SEQ ID NO: 60)
CAAGCAGAAGACGGCATACGAGAT<u>GCCTAA</u>GTGACTGGAGTTCAGACGTG
TGCTCTTCCGATCT

BC36
(SEQ ID NO: 61)
CAAGCAGAAGACGGCATACGAGAT<u>TGGTCA</u>GTGACTGGAGTTCAGACGTG
TGCTCTTCCGATCT

BC37
(SEQ ID NO: 62)
CAAGCAGAAGACGGCATACGAGAT<u>CACTGT</u>GTGACTGGAGTTCAGACGTG
TGCTCTTCCGATCT

BC38
(SEQ ID NO: 63)
CAAGCAGAAGACGGCATACGAGAT<u>ATTGGC</u>GTGACTGGAGTTCAGACGTG
TGCTCTTCCGATCT

BC39
(SEQ ID NO: 64)
CAAGCAGAAGACGGCATACGAGAT<u>GATCTG</u>GTGACTGGAGTTCAGACGTG
TGCTCTTCCGATCT

BC40
(SEQ ID NO: 65)
CAAGCAGAAGACGGCATACGAGAT<u>TCAAGT</u>GTGACTGGAGTTCAGACGTG
TGCTCTTCCGATCT

BC41
(SEQ ID NO: 66)
CAAGCAGAAGACGGCATACGAGAT<u>CTGATC</u>GTGACTGGAGTTCAGACGTG
TGCTCTTCCGATCT

BC42
(SEQ ID NO: 67)
CAAGCAGAAGACGGCATACGAGATAAGCTAGTGACTGGAGTTCAGACGTG

TGCTCTTCCGATCT

BC43
(SEQ ID NO: 68)
CAAGCAGAAGACGGCATACGAGATGTAGCCGTGACTGGAGTTCAGACGTG

TGCTCTTCCGATCT

BC44
(SEQ ID NO: 69)
CAAGCAGAAGACGGCATACGAGATTACAAGGTGACTGGAGTTCAGACGTG

TGCTCTTCCGATCT

BC45
(SEQ ID NO: 70)
CAAGCAGAAGACGGCATACGAGATTGTTGACTGTGACTGGAGTTCAGACG

TGTGCTCTTCCGATCT

BC46
(SEQ ID NO: 71)
CAAGCAGAAGACGGCATACGAGATACGGAACTGTGACTGGAGTTCAGACG

TGTGCTCTTCCGATCT

BC47
(SEQ ID NO: 72)
CAAGCAGAAGACGGCATACGAGATTCTGACATGTGACTGGAGTTCAGACG

TGTGCTCTTCCGATCT

BC48
(SEQ ID NO: 73)
CAAGCAGAAGACGGCATACGAGATCGGGACGGGTGACTGGAGTTCAGACG

TGTGCTCTTCCGATCT

BC49
(SEQ ID NO: 74)
CAAGCAGAAGACGGCATACGAGATGTGCGGACGTGACTGGAGTTCAGACG

TGTGCTCTTCCGATCT

BC50
(SEQ ID NO: 75)
CAAGCAGAAGACGGCATACGAGATCGTTTCACGTGACTGGAGTTCAGACG

TGTGCTCTTCCGATCT

BC51
(SEQ ID NO: 76)
CAAGCAGAAGACGGCATACGAGATAAGGCCACGTGACTGGAGTTCAGACG

TGTGCTCTTCCGATCT

BC52
(SEQ ID NO: 77)
CAAGCAGAAGACGGCATACGAGATACCGAAACGTGACTGGAGTTCAGACG

TGTGCTCTTCCGATCT

BC53
(SEQ ID NO: 78)
CAAGCAGAAGACGGCATACGAGATTACGTACGGTGACTGGAGTTCAGACG

TGTGCTCTTCCGATCT

BC54
(SEQ ID NO: 79)
CAAGCAGAAGACGGCATACGAGATATCCACTCGTGACTGGAGTTCAGACG

TGTGCTCTTCCGATCT

BC55
(SEQ ID NO: 80)
CAAGCAGAAGACGGCATACGAGATATATCAGTGTGACTGGAGTTCAGACG

TGTGCTCTTCCGATCT

BC56
(SEQ ID NO: 81)
CAAGCAGAAGACGGCATACGAGATAAAGGAATGTGACTGGAGTTCAGACG

TGTGCTCTTCCGATCT

Example 4

In this Example, single-stranded DNA (ssDNA) is fragmented using enzymes that cleave internal sites on ssDNA, as depicted in FIG. 3. The 5' end is phosphorylated using a kinase, then a 3' homopolymer is added. An oligonucleotide, X, having a 5' hydroxyl and 3' hydroxyl is then added to the 5' end of the ssDNA through ligation. The 5' hydroxyl on the oligonucleotide prevents self-ligation, e.g., prevents oligonucleotide dimer formation. In addition, the dideoxynucleotide at the 3' end of the homopolymer on the DNA lacks a 3' hydroxyl and thus cannot self-ligate either. The prevention of formation of these side products increases the efficiency of the reaction. Excess, unligated oligonucleotide X may be left in the products of this reaction because it is used as a PCR primer.

Following PCR amplification, the PCR products have an X and Y sequence flanking the unknown DNA sequence for downstream application.

TABLE III

| Mapping | Reference Position | Variation Type | Ref. | SNP | Frequencies (%) | Counts | Coverage | Overlapping Annotations | Amino Acid Change |
|---|---|---|---|---|---|---|---|---|---|
| NC_002505 mapping | 42082 | SNP | A | C | 100 | 107 | 107 | Gene: Gene, CDS: sun protein | Asp407Glu |
| NC_002505 mapping | 125122 | SNP | A | C | 100 | 261 | 261 | Gene: Gene, CDS: GGDEF family protein | Asn451His |
| NC_002505 mapping | 162660 | SNP | N | C | 100 | 207 | 207 | Gene: Gene, CDS: hypothetical protein | Xxx330Gly |
| NC_002505 mapping | 172531 | SNP | K | T | 100 | 224 | 224 | Gene: Gene, CDS: peptide ABC transporter,_permease protein | Xxx178Leu |
| NC_002505 mapping | 262291 | SNP | G | T | 94.4 | 17 | 18 | Gene: Gene, CDS: rfbT-related protein | Cys65Phe |
| NC_002505 mapping | 263544 | SNP | T | C | 100 | 5 | 5 | Gene: Gene, CDS: rfbT protein | |
| NC_002505 mapping | 263545 | SNP | A | C | 100 | 8 | 8 | Gene: Gene, CDS: rfbT protein | Thr4Pro |

TABLE III-continued

| Mapping | Reference Position | Variation Type | Ref. | SNP | Frequencies (%) | Counts | Coverage | Overlapping Annotations | Amino Acid Change |
|---|---|---|---|---|---|---|---|---|---|
| NC_002505 mapping | 364992 | SNP | K | G | 99.1 | 211 | 213 | Gene: Gene, CDS: hypothetical protein | Xxx69Gly |
| NC_002505 mapping | 401063 | SNP | A | G | 100 | 227 | 227 | Gene: Gene, CDS: phosphoadenosine phosphosulfate reductase | |
| NC_002505 mapping | 424629 | SNP | G | T | 100 | 170 | 170 | Gene: Gene, CDS: regulatory protein CsrD | |
| NC_002505 mapping | 424772 | SNP | G | T | 98.6 | 207 | 210 | Gene: Gene, CDS: regulatory protein CsrD | Arg504Leu |
| NC_002505 mapping | 479266 | SNP | G | T | 91.7 | 11 | 12 | | |
| NC_002505 mapping | 575609 | SNP | A | G | 100 | 228 | 228 | Gene: recA, CDS: recA | Tyr363Cys |
| NC_002505 mapping | 581125 | SNP | T | G | 98.6 | 70 | 71 | Gene: tRNA-Arg-3, tRNA: tRNA-Arg-3 | |
| NC_002505 mapping | 663766 | SNP | T | A | 99.5 | 217 | 218 | Gene: Gene, CDS: hypothetical protein | Leu82Phe |
| NC_002505 mapping | 697746 | SNP | A | G | 100 | 288 | 288 | Gene: Gene, CDS: c-di-GMP phosphodiesterase A-related protein | Val555Ala |
| NC_002505 mapping | 854836 | SNP | K | G | 100 | 168 | 168 | Gene: Gene, CDS: citrate lyase,_beta subunit | Xxx91Gly |
| NC_002505 mapping | 906942 | SNP | A | G | 100 | 195 | 195 | Gene: Gene, CDS: hypothetical protein | |
| NC_002505 mapping | 929971 | SNP | T | C | 100 | 88 | 88 | Gene: Gene, CDS: Slt family transglycosylase | |
| NC_002505 mapping | 1011632 | SNP | W | A | 99.6 | 233 | 234 | Gene: Gene, CDS: D-alanyl-D-alanine carboxypeptidase | Xxx194Asp |
| NC_002505 mapping | 1183050 | SNP | A | G | 100 | 200 | 200 | Gene: Gene, CDS: 8-amino-7-oxononanoate synthase | Arg20Gly |
| NC_002505 mapping | 1237259 | SNP | C | G | 97.9 | 187 | 191 | Gene: Gene, CDS: hypothetical protein | Glu192Gln |
| NC_002505 mapping | 1237260 | SNP | G | C | 98.9 | 188 | 190 | Gene: Gene, CDS: hypothetical protein | His191Gln |
| NC_002505 mapping | 1335598 | SNP | A | G | 100 | 157 | 157 | Gene: Gene, CDS: hypothetical protein | Asn107Ser |
| NC_002505 mapping | 1417919 | SNP | T | G | 99.4 | 158 | 159 | Gene: Gene, CDS: hypothetical protein | |
| NC_002505 mapping | 1542173 | SNP | C | T | 99.4 | 180 | 181 | Gene: Gene, CDS: sensor histidine kinase/response regulator | Ser241Leu |
| NC_002505 mapping | 1561424 | SNP | K | G | 100 | 174 | 174 | Gene: Gene, CDS: RTX toxin RtxA | Xxx3773Asp |
| NC_002505 mapping | 1561926 | SNP | S | C | 100 | 164 | 164 | Gene: Gene, CDS: RTX toxin RtxA | Xxx3940Ala |
| NC_002505 mapping | 1561942 | SNP | S | G | 100 | 151 | 151 | Gene: Gene, CDS: RTX toxin RtxA | |
| NC_002505 mapping | 1561949 | SNP | W | A | 100 | 158 | 158 | Gene: Gene, CDS: RTX toxin RtxA | Xxx3948Asn |
| NC_002505 mapping | 1587146 | SNP | K | G | 100 | 4 | 4 | Gene: Gene, CDS: ATP-dependent protease LA-related protein | |
| NC_002505 mapping | 1587147 | SNP | Y | T | 100 | 4 | 4 | Gene: Gene, CDS: ATP-dependent protease LA-related protein | |
| NC_002505 mapping | 1587148 | SNP | Y | C | 100 | 6 | 6 | Gene: Gene, CDS: ATP-dependent protease LA-related protein | |
| NC_002505 mapping | 1587149 | SNP | Y | T | 100 | 10 | 10 | Gene: Gene, CDS: ATP-dependent protease LA-related protein | Xxx196Ser |
| NC_002505 mapping | 1587765 | SNP | W | T | 99.5 | 205 | 206 | Gene: Gene, CDS: ATP-dependent protease LA-related protein | Xxx401Val |
| NC_002505 mapping | 1591816 | SNP | A | G | 100 | 194 | 194 | Gene: Gene, Restriction site: BsaBI, CDS: ABC transporter ATPase component | |
| NC_002505 mapping | 1670764 | SNP | W | T | 100 | 234 | 234 | | |
| NC_002505 mapping | 1696639 | SNP | Y | C | 99.2 | 130 | 131 | Gene: Gene, CDS: catalase | Asx522Asp |
| NC_002505 mapping | 1696645 | SNP | Y | C | 99.2 | 119 | 120 | Gene: Gene, CDS: catalase | Xxx520Ala |
| NC_002505 mapping | 1735241 | SNP | M | C | 99.5 | 201 | 202 | Gene: Gene | |

TABLE III-continued

| Mapping | Reference Position | Variation Type | Ref. | SNP | Frequencies (%) | Counts | Coverage | Overlapping Annotations | Amino Acid Change |
|---|---|---|---|---|---|---|---|---|---|
| NC_002505 mapping | 1792474 | SNP | C | A | 100 | 246 | 246 | Gene: Gene | |
| NC_002505 mapping | 2010846 | SNP | G | A | 100 | 112 | 112 | Gene: Gene, CDS: methyl-accepting chemotaxis protein | Arg483Cys |
| NC_002505 mapping | 2076300 | SNP | A | G | 100 | 187 | 187 | Gene: Gene, CDS: C4-dicarboxylate transport sensor protein | Asn187Ser |
| NC_002505 mapping | 2122955 | SNP | R | G | 100 | 145 | 145 | Gene: Gene, CDS: 0-succinylbenzoic acid--CoA ligase | |
| NC_002505 mapping | 2122956 | SNP | M | C | 100 | 144 | 144 | Gene: Gene, CDS: 0-succinylbenzoic acid--CoA ligase | Xxx110Trp |
| NC_002505 mapping | 2148579 | SNP | A | G | 100 | 201 | 201 | Gene: Gene, CDS: protease IV | |
| NC_002505 mapping | 2153724 | SNP | T | A | 98.9 | 174 | 176 | Gene: Gene, CDS: hypothetical protein | Ile106Asn |
| NC_002505 mapping | 2179341 | SNP | C | G | 100 | 177 | 177 | Gene: maf, CDS: maf | Leu47Val |
| NC_002505 mapping | 2318560 | SNP | G | A | 100 | 9 | 9 | Gene: Gene, CDS: hypothetical protein | Leu 1 9Phe |
| NC_002505 mapping | 2378839 | SNP | N | G | 100 | 214 | 214 | Gene: Gene, CDS: GGDEF family protein | Xxx227Ser |
| NC_002505 mapping | 2379972 | SNP | A | G | 100 | 128 | 128 | Gene: upp, CDS: upp | Ile135Thr |
| NC_002505 mapping | 2488985 | SNP | G | T | 99.6 | 252 | 253 | Gene: Beta Galactosidase (LacZ) | |
| NC_002505 mapping | 2496376 | SNP | T | C | 100 | 196 | 196 | Gene: Gene, CDS: elongation factor G | Ser370Gly |
| NC_002505 mapping | 2590300 | SNP | R | A | 100 | 194 | 194 | Gene: Gene, CDS: 2`,3`-cyclic-nucleotide 2`-phosphodiesterase, putative | Xxx481Glu |
| NC_002505 mapping | 2682957 | SNP | R | G | 100 | 178 | 178 | Gene: Gene, CDS: hypothetical protein | Xxx73Pro |
| NC_002505 mapping | 2682978 | SNP | S | G | 100 | 142 | 142 | Gene: Gene, CDS: hypothetical protein | Xxx66Pro |
| NC_002505 mapping | 2881400 | SNP | C | A | 98.8 | 164 | 166 | Gene: Gene, CDS: bifunctional (p)ppGpp synthetase II/ guanosine-3',5'-bis pyrophosphate 3'-pyrophosphohydrolase | Pro142His |
| NC_002506 mapping | 44129 | SNP | A | G | 100 | 57 | 57 | Gene: Gene, CDS: serine/threonine transporter SstT | Val390Ala |
| NC_002506 mapping | 85485 | SNP | T | G | 100 | 124 | 124 | Gene: Gene, CDS: hypothetical protein | 11e247Leu |
| NC_002506 mapping | 152561 | SNP | C | A | 99.6 | 247 | 248 | Gene: glpT, CDS: glpT | Gly44Val |
| NC_002506 mapping | 161478 | SNP | C | G | 99.3 | 133 | 134 | Gene: Gene, CDS: hypothetical protein | Arg377Gly |
| NC_002506 mapping | 186754 | SNP | C | T | 100 | 5 | 5 | Gene: Gene, CDS: hypothetical protein | |
| NC_002506 mapping | 219397 | SNP | T | C | 99.2 | 131 | 132 | Gene: Gene, CDS: hypothetical protein | |
| NC_002506 mapping | 277301 | SNP | A | G | 100 | 157 | 157 | Gene: Gene, CDS: sensor histidine kinase | |
| NC_002506 mapping | 310944 | SNP | G | T | 100 | 17 | 17 | | |
| NC_002506 mapping | 310945 | SNP | C | A | 100 | 16 | 16 | | |
| NC_002506 mapping | 310946 | SNP | T | A | 100 | 9 | 9 | | |
| NC_002506 mapping | 312308 | SNP | G | A | 100 | 4 | 4 | | |
| NC_002506 mapping | 312309 | SNP | C | A | 100 | 10 | 10 | | |
| NC_002506 mapping | 312310 | SNP | G | A | 100 | 16 | 16 | | |
| NC_002506 mapping | 356433 | SNP | Y | T | 100 | 24 | 24 | | |
| NC_002506 mapping | 366180 | SNP | Y | C | 100 | 186 | 186 | Gene: Gene, CDS: toxin resistance protein | |
| NC_002506 mapping | 566512 | SNP | C | G | 97.7 | 209 | 214 | Gene: Gene, CDS: hypothetical protein | Arg256Pro |
| NC_002506 mapping | 566513 | SNP | G | C | 100 | 204 | 204 | Gene: Gene, CDS: hypothetical protein | Arg256Gly |

TABLE III-continued

| Mapping | Reference Position | Variation Type | Ref. | SNP | Frequencies (%) | Counts | Coverage | Overlapping Annotations | Amino Acid Change |
|---|---|---|---|---|---|---|---|---|---|
| NC_002506 mapping | 588148 | SNP | C | G | 100 | 149 | 149 | Gene: Gene, CDS: PTS system,_sucrose-specific IIBC component | Arg115Pro |
| NC_002506 mapping | 646810 | SNP | Y | T | 100 | 220 | 220 | Gene: Gene, CDS: phosphoglycerate transport regulatory protein PgtB,_putative | |
| NC_002506 mapping | 788542 | SNP | G | T | 99.6 | 228 | 229 | | |
| NC_002506 mapping | 811408 | SNP | T | C | 100 | 216 | 216 | Gene: Gene, CDS: hypothetical protein | |
| NC_002506 mapping | 886005 | SNP | C | T | 100 | 91 | 91 | | |
| NC_002506 mapping | 894743 | SNP | G | T | 99.5 | 205 | 206 | Gene: malF, CDS: malF | Phe397Leu |
| NC_002506 mapping | 901045 | SNP | C | T | 100 | 206 | 206 | Gene: Gene, CDS: hypothetical protein | Ser36Phe |
| NC_002506 mapping | 980511 | SNP | C | G | 96.6 | 199 | 206 | Gene: Gene | |
| NC_002506 mapping | 980512 | SNP | G | C | 100 | 201 | 201 | Gene: Gene | |
| NC_002506 mapping | 980632 | SNP | C | G | 98.3 | 229 | 233 | Gene: Gene | |
| NC_002506 mapping | 980633 | SNP | G | C | 97 | 227 | 234 | Gene: Gene | |
| NC_002506 mapping | 986611 | SNP | A | G | 100 | 6 | 6 | Gene: Gene | |
| NC_002506 mapping | 993684 | SNP | C | A | 100 | 101 | 101 | Gene: Gene, CDS: tagE protein | |
| NC_002506 mapping | 993701 | SNP | T | C | 100 | 7 | 7 | Gene: Gene, CDS: tagE protein | Arg200Gly |
| NC_002506 mapping | 1004685 | SNP | T | G | 100 | 126 | 126 | Gene: Gene, CDS: LysR family transcriptional regulator | Val73Gly |
| AB374228 mapping | 4195 | SNP | A | T | 99.6 | 239 | 240 | Gene: cII, CDS: cII | Gln103Leu |
| AB374228 mapping | 4296 | SNP | A | T | 100 | 87 | 87 | Gene: cII, CDS: cII | Ser137Cys |
| AB374228 mapping | 4302 | SNP | A | G | 100 | 99 | 99 | Gene: cII, CDS: cII | Thr139Ala |

TABLE IV

| Mapping | Reference Position | Length | Reference | DIP Variations | Frequencies (%) | Counts | Coverage | Overlapping Annotations | Amino Acid Change |
|---|---|---|---|---|---|---|---|---|---|
| NC_002505 mapping | 359986 | 1 | — | T | 85.3 | 185 | 217 | Gene: Gene, CDS: ribosome-associated GTPase | Change, frameshift |
| NC_002505 mapping | 424645 | 1 | — | G | 87 | 120 | 138 | Gene: Gene, CDS: regulatory protein CsrD | Change, frameshift |
| NC_002505 mapping | 424670 | 1 | G | — | 88.2 | 67 | 76 | Gene: Gene, CDS: regulatory protein CsrD | Change, frameshift |
| NC_002505 mapping | 479266 | 1 | G | — | 94.2 | 196 | 208 | | |
| NC_002505 mapping | 540850 | 1 | C | — | 90.3 | 176 | 195 | | |
| NC_002505 mapping | 553569 | 1 | — | C | 97.4 | 190 | 195 | Gene: dnaG, CDS: dnaG | Change, frameshift |
| NC_002505 mapping | 555404 | 1 | — | G | 79.2 | 80 | 101 | Gene: gcp, CDS: gcp | Change, frameshift |
| NC_002505 mapping | 612959 | 1 | — | A | 86.8 | 165 | 190 | Gene: Gene | |
| NC_002505 mapping | 623228 | 1 | — | G | 94 | 205 | 218 | Gene: Gene, CDS: glutamyl-Q tRNA(Asp) synthetase | Change, frameshift |
| NC_002505 mapping | 638168 | 1 | — | T | 90.5 | 218 | 241 | Gene: Gene | |
| NC_002505 mapping | 807832 | 1 | — | G | 95.5 | 171 | 179 | | |
| NC_002505 mapping | 849965 | 1 | — | G | 89.2 | 91 | 102 | Gene: Gene, Gene: oadA-2, CDS: oadA-2 | Change, frameshift |
| NC_002505 mapping | 872713 | 1 | — | A | 81.4 | 114 | 140 | | |

TABLE IV-continued

| Mapping | Reference Position | Length | Reference | DIP Variations | Frequencies (%) | Counts | Coverage | Overlapping Annotations | Amino Acid Change |
|---|---|---|---|---|---|---|---|---|---|
| NC_002505 mapping | 881244 | 1 | — | T | 87.8 | 158 | 180 | Gene: Gene, CDS: hypothetical protein | Change, frameshift |
| NC_002505 mapping | 998435 | 1 | — | C | 95.8 | 205 | 214 | Gene: Gene, Gene: Gene, CDS: hypothetical protein, CDS: hypothetical protein | Change, frameshift |
| NC_002505 mapping | 1087962 | 1 | — | G | 95.4 | 103 | 108 | Gene: uvrB, CDS: uvrB | Change, frameshift |
| NC_002505 mapping | 1145407 | 1 | — | G | 90.6 | 116 | 128 | Gene: Gene, CDS: AraC/Xy1S family transcriptional regulator | Change, frameshift |
| NC_002505 mapping | 1228191 | 1 | — | C | 91.9 | 113 | 123 | Gene: Gene, Gene: Gene, CDS: sensor histidine kinase, CDS: response regulator | Change, frameshift |
| NC_002505 mapping | 1337746 | 1 | T | — | 85.5 | 106 | 124 | | |
| NC_002505 mapping | 1389484 | 1 | — | C | 90.8 | 138 | 152 | Gene: Gene | |
| NC_002505 mapping | 1470952 | 1 | — | G | 96 | 167 | 174 | Gene: Gene, CDS: GGDEF family protein | Change, frameshift |
| NC_002505 mapping | 1486534 | 1 | — | C | 88.5 | 54 | 61 | Gene: Gene | |
| NC_002505 mapping | 1489715 | 1 | — | T | 81.7 | 161 | 197 | Gene: Gene, CDS: chemotaxis protein methyltransferase CheR | Change, frameshift |
| NC_002505 mapping | 1530608 | 1 | — | C | 79.7 | 55 | 69 | | |
| NC_002505 mapping | 1618601 | 1 | — | C | 91.8 | 157 | 171 | Gene: Gene, CDS: hypothetical protein | Change, frameshift |
| NC_002505 mapping | 1625933 | 1 | — | C | 91.6 | 98 | 107 | Gene: Gene | |
| NC_002505 mapping | 1649049 | 1 | C | — | 90.4 | 103 | 114 | Gene: Gene, CDS: hypothetical protein | Change, frameshift |
| NC_002505 mapping | 1676600 | 1 | — | C | 87.6 | 113 | 129 | Gene: Gene, CDS: hypothetical protein | Change, frameshift |
| NC_002505 mapping | 1676702 | 1 | — | C | 95.2 | 216 | 227 | Gene: Gene, CDS: hypothetical protein | Change, frameshift |
| NC_002505 mapping | 1676704 | 1 | — | A | 86 | 203 | 236 | Gene: Gene, CDS: hypothetical protein | Change, frameshift |
| NC_002505 mapping | 1748765 | 1 | — | C | 92.4 | 133 | 144 | Gene: Gene | |
| NC_002505 mapping | 1771830 | 1 | — | A | 85.8 | 199 | 232 | Gene: Gene, CDS: hypothetical protein | Change, frameshift |
| NC_002505 mapping | 1875074 | 1 | — | T | 84.1 | 191 | 227 | Gene: Gene, CDS: hypothetical protein | Change, frameshift |
| NC_002505 mapping | 1900854 | 1 | T | — | 86.9 | 185 | 213 | Gene: Gene, CDS: hypothetical protein | Change, frameshift |
| NC_002505 mapping | 1990030 | 1 | — | T | 93.8 | 121 | 129 | Gene: Gene, CDS: UDP-2,3-diacylglucosamine hydrolase | Change, frameshift |
| NC_002505 mapping | 2051793 | 1 | — | C | 80.9 | 161 | 199 | | |
| NC_002505 mapping | 2081077 | 1 | — | C | 90.1 | 183 | 203 | | |
| NC_002505 mapping | 2194678 | 1 | — | G | 88.1 | 155 | 176 | Gene: Gene, CDS: hypothetical protein | Change, frameshift |
| NC_002505 mapping | 2262543 | 1 | T | — | 83.3 | 169 | 203 | Gene: Gene, Gene: Gene, CDS: hypothetical protein, CDS: hypothetical protein | Change, frameshift |
| NC_002505 mapping | 2266655 | 1 | — | C | 94.7 | 89 | 94 | Gene: Gene | |
| NC_002505 mapping | 2318560 | 1 | G | — | 91 | 91 | 100 | Gene: Gene, CDS: hypothetical protein | Change, frameshift |
| NC_002505 mapping | 2358194 | 1 | — | C | 92.9 | 221 | 238 | Gene: vibF, CDS: vibF | Change, frameshift |
| NC_002505 mapping | 2365248 | 1 | — | G | 85.8 | 187 | 218 | | |
| NC_002505 mapping | 2489046 | 1 | — | G | 91.9 | 148 | 161 | Gene: Beta Galactosidase (Lac Z) | |
| NC_002505 mapping | 2564032 | 1 | — | C | 90.1 | 182 | 202 | Gene: 1pxC, CDS: 1pxC | Change, frameshift |
| NC_002505 mapping | 2612864 | 1 | — | C | 87.1 | 128 | 147 | Gene: Gene | |
| NC_002505 mapping | 2657595 | 1 | — | C | 95.5 | 213 | 223 | Gene: Gene, CDS: hypothetical protein | Change, frameshift |
| NC_002505 mapping | 2738434 | 1 | — | C | 92.7 | 203 | 219 | Gene: Gene, CDS: hypothetical protein | Change, frameshift |
| NC_002505 mapping | 2839613 | 1 | — | C | 96.8 | 181 | 187 | Gene: Gene, CDS: ribonuclease activity regulator protein RraA | Change, frameshift |

TABLE IV-continued

| Mapping | Reference Position | Length | Reference | DIP Variations | Frequencies (%) | Counts | Coverage | Overlapping Annotations | Amino Acid Change |
|---|---|---|---|---|---|---|---|---|---|
| NC_002505 mapping | 2879855 | 1 | T | — | 91 | 181 | 199 | Gene: Gene, CDS: hypothetical protein | Change, frameshift |
| NC_002505 mapping | 2907037 | 1 | — | G | 90.3 | 187 | 207 | Gene: Gene | |
| NC_002506 mapping | 17393 | 1 | C | — | 96.5 | 165 | 171 | Gene: Gene, Gene: Gene, CDS: hypothetical protein, CDS: glycogen branching enzyme | Change, frameshift |
| NC_002506 mapping | 53608 | 1 | T | — | 90.8 | 177 | 195 | Gene: Gene, Gene: Gene, CDS: hypothetical protein, CDS: protease-related protein | Change, frameshift |
| NC_002506 mapping | 57465 | 1 | — | G | 89.6 | 103 | 115 | Gene: Gene, Gene: Gene, CDS: GGDEF family protein, CDS: hypothetical protein | Change, frameshift |
| NC_002506 mapping | 97575 | 1 | G | — | 92.2 | 202 | 219 | Gene: Gene, CDS: proton/glutamate symporter | Change, frameshift |
| NC_002506 mapping | 144626 | 1 | A | — | 82.4 | 122 | 148 | Gene: rbsC, CDS: rbsC | Change, frameshift |
| NC_002506 mapping | 184512 | 1 | — | C | 87 | 47 | 54 | | |
| NC_002506 mapping | 186168 | 1 | — | G | 98.9 | 86 | 87 | Gene: Gene, Gene: Gene, CDS: hypothetical protein, CDS: hypothetical protein | Change, frameshift |
| NC_002506 mapping | 255374 | 1 | — | G | 83 | 78 | 94 | Gene: Gene | |
| NC_002506 mapping | 279450 | 1 | — | C | 87.6 | 113 | 129 | Gene: Gene, CDS: hypothetical protein | Change, frameshift |
| NC_002506 mapping | 294983 | 1 | — | G | 86.6 | 97 | 112 | Gene: Gene | |
| NC_002506 mapping | 299055 | 1 | G | — | 94.8 | 184 | 194 | Gene: Gene | |
| NC_002506 mapping | 299080 | 1 | C | — | 87.1 | 121 | 139 | Gene: Gene | |
| NC_002506 mapping | 403877 | 1 | — | G | 95.1 | 117 | 123 | Gene: Gene, CDS: hypothetical protein | Change, frameshift |
| NC_002506 mapping | 472297 | 1 | A | — | 97.4 | 149 | 153 | Gene: Gene | |
| NC_002506 mapping | 474527 | 1 | — | C | 90 | 208 | 231 | Gene: Gene, CDS: hypothetical protein | Change, frameshift |
| NC_002506 mapping | 530511 | 1 | A | — | 96.1 | 149 | 155 | | |
| NC_002506 mapping | 535093 | 1 | G | — | 93.4 | 211 | 226 | Gene: Gene, Gene: Gene, CDS: hypothetical protein | Change, frameshift |
| NC_002506 mapping | 545436 | 1 | — | C | 92.3 | 179 | 194 | | |
| NC_002506 mapping | 609601 | 1 | — | G | 94.1 | 144 | 153 | Gene: Gene | |
| NC_002506 mapping | 631352 | 1 | — | G | 95.3 | 204 | 214 | Gene: Gene | |
| NC_002506 mapping | 631405 | 1 | — | G | 86.7 | 104 | 120 | Gene: Gene | |
| NC_002506 mapping | 686744 | 1 | — | C | 96 | 166 | 173 | | |
| NC_002506 mapping | 690275 | 1 | A | — | 97.2 | 141 | 145 | Gene: Gene | |
| NC_002506 mapping | 743256 | 1 | — | G | 89 | 121 | 136 | | |
| NC_002506 mapping | 765560 | 1 | G | — | 92.9 | 65 | 70 | Gene: Gene, CDS: magnesium transporter MgtE,_putative | Change, frameshift |
| NC_002506 mapping | 769970 | 1 | — | T | 94.8 | 147 | 155 | Gene: Gene, CDS: diaminobutyrate--2-oxoglutarate aminotransferase | Change, frameshift |
| NC_002506 mapping | 771746 | 1 | — | G | 97.6 | 160 | 164 | | |
| NC_002506 mapping | 775705 | 1 | — | G | 89.3 | 216 | 242 | Gene: Gene, CDS: acetoacetyl-CoA synthetase | Change, frameshift |
| NC_002506 mapping | 869466 | 1 | C | — | 93.7 | 178 | 190 | | |
| NC_002506 mapping | 889857 | 1 | — | G | 90.1 | 146 | 162 | Gene: Gene | |
| NC_002506 mapping | 893324 | 1 | A | — | 94.2 | 210 | 223 | | |
| NC_002506 mapping | 969852 | 1 | — | T | 92.5 | 209 | 226 | Gene: Gene, Gene: Gene, CDS: hypothetical protein, CDS: hypothetical protein | Change, frameshift |
| NC_002506 mapping | 980877 | 1 | G | — | 95 | 191 | 201 | Gene: Gene | |

TABLE IV-continued

| Mapping | Reference Position | Length | Reference | DIP Variations | Frequencies (%) | Counts | Coverage | Overlapping Annotations | Amino Acid Change |
|---|---|---|---|---|---|---|---|---|---|
| NC_002506 mapping | 980886 | 1 | — | G | 92.8 | 192 | 207 | Gene: Gene | |
| NC_002506 mapping | 981512 | 1 | A | — | 92.4 | 121 | 131 | Gene: Gene | |
| NC_002506 mapping | 986611 | 2 | AA | — | 97.5 | 118 | 121 | Gene: Gene | |
| NC_002506 mapping | 993674 | 1 | C | — | 88.3 | 91 | 103 | Gene: Gene, CDS: tagE protein | Change, frameshift |
| NC_002506 mapping | 993700 | 2 | CT | — | 94 | 78 | 83 | Gene: Gene, CDS: tagE protein | Change, frameshift |
| NC_002506 mapping | 1036512 | 1 | — | G | 95.7 | 267 | 279 | Gene: Gene, CDS: hypothetical protein | Change, frameshift |
| NC_002506 mapping | 1045002 | 1 | — | G | 94.3 | 215 | 228 | Gene: Gene | |
| NC_002506 mapping | 1060870 | 1 | — | C | 94.9 | 168 | 177 | Gene: Gene | |
| NC_002506 mapping | 1060888 | 1 | — | C | 91.7 | 133 | 145 | Gene: Gene | |
| NC_002506 mapping | 1062459 | 1 | — | G | 96.2 | 176 | 183 | Gene: Gene, CDS: hypothetical protein | Change, frameshift |
| AB374228 mapping | 4914 | 1 | A | — | 74.2 | 196 | 264 | | |
| AB374228 mapping | 5689 | 1 | — | G | 92.8 | 206 | 222 | Gene: kp9, CDS: kp9 | Change, frameshift |
| AB374228 mapping | 7865 | 1 | — | C | 80.5 | 99 | 123 | Gene: rep, CDS: rep | Change, frameshift |
| AB374228 mapping | 17096 | 1 | — | A | 94.5 | 224 | 237 | Gene: kp24, CDS: kp24 | Change, frameshift |
| AB374228 mapping | 19381 | 1 | — | G | 98.7 | 74 | 75 | Gene: kp28, CDS: kp28 | Change, frameshift |
| AB374228 mapping | 22704 | 2 | — | GC | 82.2 | 176 | 214 | Gene: kp36, CDS: kp36 | Change, frameshift |

Example 6

In the present Example, an adapted Mariner transposon system was used for mutagenesis of *Porphyromonas gingivalis* (*P. gingivalis*), and then an exemplary embodiment of the homopolymer-mediated nucleic acid amplification method of the invention was used to create an insertion mutant library. *P. gingivalis* is a Gram-negative anaerobic bacterium associated with periodontal disease onset and progression. Genetic tools for the manipulation of bacterial genomes allow for in-depth mechanistic studies of metabolism, physiology, interspecies and host-pathogen interactions. Analysis of the essential genes and protein-coding sequences necessary for survival of *P. gingivalis* by transposon mutagenesis has not previously been attempted due to the limitations of available transposon systems for the organism. By analyzing the location of insertions using massively-parallel sequencing technology and the methods provided herein, this mutant library was used to define genes essential for *P. gingivalis* survival under in vitro conditions (Klein, B. et al. *BMC Genomics* 2012, 13:578, incorporated by reference herein in its entirety).

In the mutagenesis experiments described below, 463 genes putatively essential for viability in vitro were identified in *P. gingivalis* strain ATCC 33277. Comparing the 463 *P. gingivalis* essential genes with previous essential gene studies, 364 of the 463 are homologues to essential genes in other species; 339 are shared with more than one other species. Twenty-five genes are known to be essential in *P. gingivalis* and *B. thetaiotaomicron* only. Significant enrichment of essential genes within Cluster of Orthologous Groups 'D' (cell division), 'I' (lipid transport and metabolism) and T (translation/ribosome) were identified. Previously, the *P. gingivalis* core genome was shown to encode 1,476 proteins out of a possible 1,909; 434 of 463 essential genes are contained within the core genome. Thus, for the species *P. gingivalis* twenty-two, seventy-seven and twenty-three percent of the genome respectively are devoted to essential, core and accessory functions.

Generation of the Mutant Library

Transposon insertion libraries were generated in *P. gingivalis* using a Himar 1 Mariner mini-transposon system created for use in *Bacteroides thetaiotaomicron* (Goodman A L, et al. *Cell Host Microbe* 2009, 6:279-289, incorporated by reference herein in its entirety). The *B. thetaiotaomicron* promoter of BT1331 that drives expression of himar1c9a transposase is recognized by *P. gingivalis*, allowing use of the *B. thetaiotaomicron* plasmid vector pSAM_Bt with modifications in growth media and antibiotic selection conditions. This minitransposon was constructed with two translational terminators downstream of the gene for antibiotic selection, thus eliminating read-through downstream from the insertion.

Figure 7:
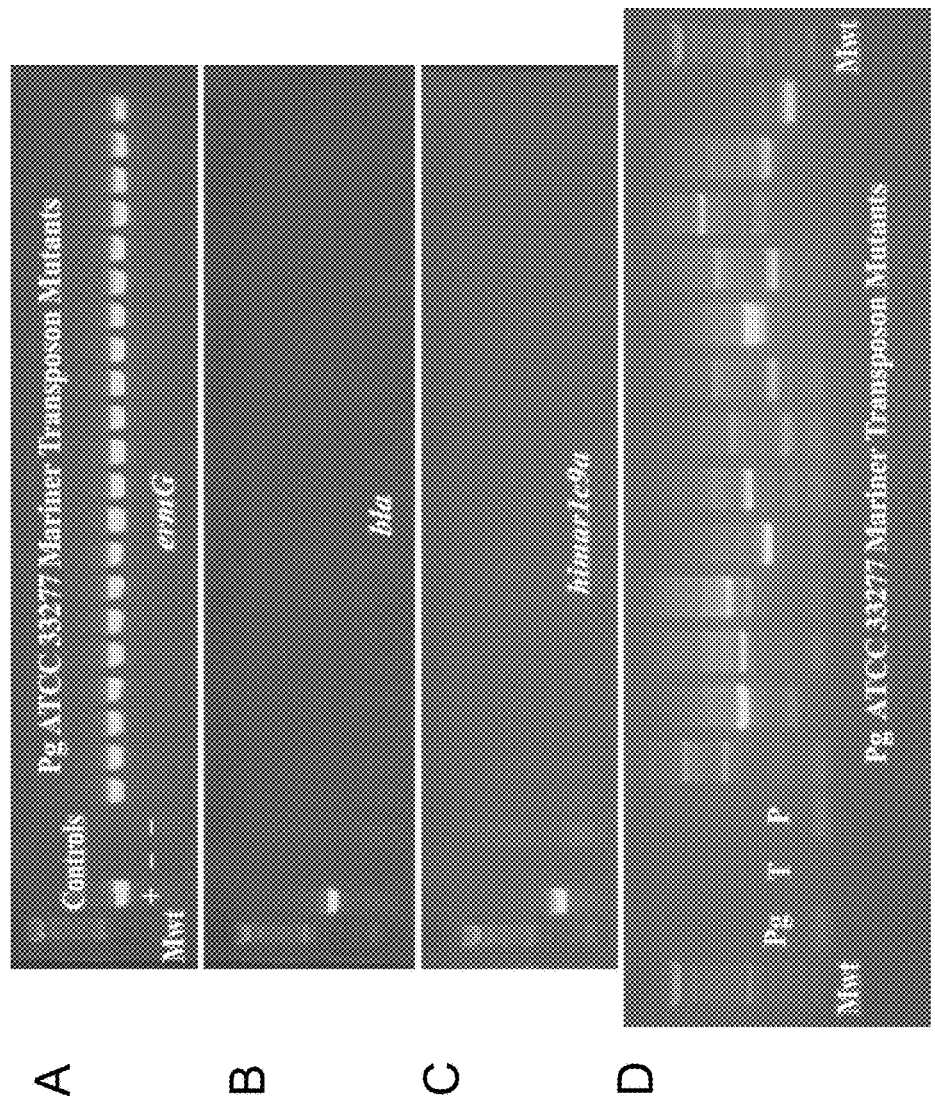
FIGS. 7A-7D provide images of electrophoretic gels showing PCR amplified transposon insertions in the *Porphyromonas gingivalis* (*P. gingivalis*) genome (confirmation of transposon insertions was performed by PCR for presence of transposon (ermG))

Mutagenesis was performed using pSAM_Bt with *P. gingivalis* strain ATCC 33277. The 4.6 kb pSAM_Bt vector containing the Mariner mini-transposon cannot replicate in *P. gingivalis* and, in addition, the plasmid lacks sequence homology with the *P. gingivalis* genome. Therefore, after the plasmid enters *P. gingivalis* by transformation, transposition from the plasmid into the genome occurs without significant background insertion of the plasmid into the genome by illegitimate recombination. This system allows for single, stable transposition events because transposase activity is lost along with the plasmid. 54,000 transposon insertion strains (individual colonies) were collected from six separate transformation experiments. Variable colony sizes were observed among the mutants harvested and pooled following 14 days of growth. Nonetheless, the majority of macroscopically visible colonies were similar in size to those of wild-type *P. gingivalis* strain ATCC 33277 after 14 days of growth. To confirm that the strains contained transposon insertions and not cryptic or full plasmid integrations, PCR was performed, which was specific for the transposon (ermG) as well as for two portions of the vector backbone (himar1c9a and bla). FIGS. 7A-7D provide images of electrophoretic gels showing PCR amplified transposon insertions in the *Porphyromonas gingivalis* (*P. gingivalis*) genome. FIGS. 7A-7C are a combination of separate gels, all of which were run using identical PCR gDNA template for each of the separate reactions. FIGS. 7B and 7C show PCR amplicons of the same samples using primers for the bla and himar1c19a genes, respectively, which are present in the plasmid, but which should be lost with proper insertion of the transposon. The PCR amplicons for individual mutant sequencing, as shown in FIG. 7D, were produced using nested semi-random PCR. Two rounds of nested PCR were performed: negative controls of wild-type *P. gingivalis* strain ATCC 33277 (Pg), template only (T) and primer only (P) lanes precede thirteen individual mutants.

Of 100 colonies that were screened for transposon insertions, all showed positive PCR reactions for the transposon gene and negative reactions for the vector backbone, indicating 'correct' transposition. 'Incorrect' transpositions can include portions of the vector backbone inserting with the transposon, the vector being stably maintained within the bacterium extrachromosomally or multiple insertions within the same genome; such transposition events were not detected in the subset of mutants tested (FIGS. 7A-7D). To determine whether the transposon inserted into different genes and not preferentially into genetic 'hot-spots,' nested semi-random PCR was performed, followed by sequencing, which confirmed that insertions occurred in multiple locations across the genome (FIG. 7D) (Beeman R W, et al. *Insect Mol Biol* 1997, 6:83-88, incorporated by reference herein in its entirety). This traditional sequencing method is effective for targeted sequencing a subset of mutants from the mutant library if massively-parallel high-throughput is neither desired nor necessary.

Validation of Tn-seq of the *P. gingivalis* Library

Having confirmed via nested semi-random PCR and subsequent sequencing that the libraries contained different transposon insertions scattered throughout the genome, the location of each insertion in the library was identified by Tn-seq analysis (van Opijnen T, et al. *Nat Methods* 2009, 6:767-772; van Opijnen T, et al. *Curr Protoc Microbiol* 2010, Chapter 1: Unit1E.3, each of which is incorporated by reference herein in its entirety). This method coupled transposon mutagenesis with massively-parallel, next-generation sequencing (NGS) technology (for review of NGS, see, e.g., Bosch, J. R., et al. *J Mol Diagn.*, 2008, 10(6): 484-492, incorporated by reference herein for its teachigns relating to NGS) to identify the location of each insertion and quantitate the relative abundance of each insertion mutant in the library.

Figure 8:
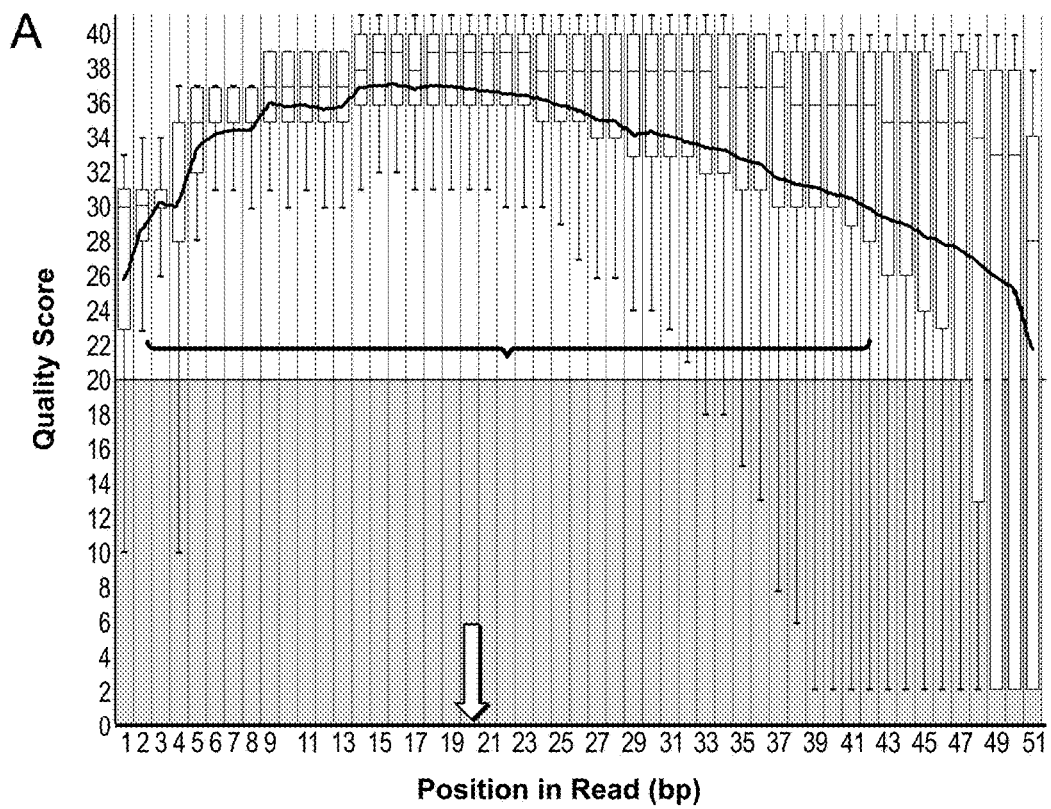
FIGS. 8A and 8B provide graphs of data showing sequencing quality control and reproducibility.
Figure 8:
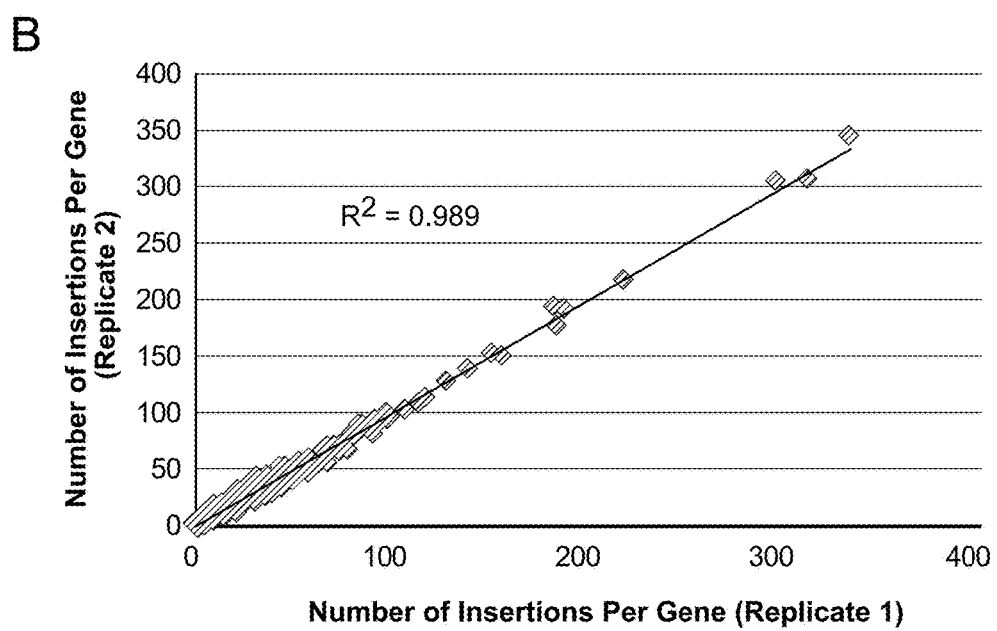

For the construction of the high-throughput sequencing library from transposon element insertions, genomic DNA containing the insertion element of interest was sheared, and then terminal deoxynucleotidyl transferase (TdT) was used to add an average of twenty deoxycytidine nucleotides to the 3' ends of all molecules. Two rounds of PCR using a poly-C-specific and an insertion element-specific primer pair were then used to amplify one of the two insertion element-genomic DNA junctions and append all user-defined sequences needed for high-throughput sequencing and indexing. This particular exemplary embodiment of a homopolymer-mediated nucleic acid amplification method of the invention does not require a ligation reaction, does not produce adapter dimers, does not require gel purification and is compatible with long sequencing reads, the size of which is limited only by the length of library fragments and the sequencing technology. Here, in contrast to the 16-18 nucleotide reads obtained with the MmeI method, 50 nucleotide reads were used, allowing for significantly more effective and precise mapping of sequences to regions with nucleotide repeats as well as genes that contain nucleotide homology (FIG. 8A). This is particularly important given that the current Illumina® HiSeq2000 base-calling algorithm gives poor quality scores for the first few bases (FIG. 8A).

Two replicate samples derived from the same master mutant library, but processed separately for sequencing, were compared. Sequencing revealed 35,937 and 35,732 distinct insertions (mutants) respectively (FIG. 8B). Of the total insertions, 7,230 and 7,193 in the respective replicate runs were in putative intergenic regions. After quality filtering sequencing reads an average 6,310,573 reads could be attributed to an average of 35,835 insertions mapped to the genome. Of note, during multiplexed Illumina® sequencing runs between 10-20 percent of sequencing reads are 'thrown out' during quality control analyses. This level of 'discarded' read data is seen by all groups performing permutations of Tn-seq, RNA-seq, ChIP-seq and other massively-parallel adapted methods. Sequencing data removed during the quality control analyses was within the 10-20 percent range previously noted. The number of insertions per gene, and the number of reads per gene when comparing the technical replicates, gave R2 values of 0.989 and 0.998, respectively (FIG. 8B). The similarity between the two technical replicates demonstrates that aliquot production from the master library, processing of the samples as well as sequencing and analyses are highly reproducible.

FIG. 8A shows quality scores of the sequencing reads for mapping. Fifty base pair single-end reads were obtained with 'high' quality out to ~42 base pairs and 'good' quality out to ~47 base pairs. The upper portion of the graph corresponds to high quality reads, the middle portion corresponds to intermediate quality reads and the lower portion corresponds to poor quality reads. Data shown are for the number of high, intermediate and low quality reads at a specific number of base pairs away from the transposon. The light gray bar encompasses the 25-75th percentile, and the darker gray horizontal bar indicates the mean. The dark gray bracket identifies the base pair position where high quality reads comprise the over 75% of the total reads; The arrow signifies the typical amount of sequencing that can be obtained when preparing DNA using the MmeI restriction site, demonstrating superior mapping and analysis ability of homopolymer-mediated amplification method of the invention. No sequencing reads shorter than 20 by were used for analyses. FIG. 8B: replicates of the same library were sequenced in separate experiments. The graph compares the number of insertions per gene for technical replicates 1 and 2 of *P. gingivalis* strain ATCC 33277 Mariner mutant library and showed excellent correlation between the replicates (R2=0.9892). The median number of insertions when excluding genes containing zero is 9, while the mean is 17. Sixteen genes have 100 insertions or greater.

Methods

Transposon Mutagenesis

*P. gingivalis* Mariner-based transposon mutagenesis was carried out as follows. Wild-type *P. gingivalis* (strain ATCC 33277) was inoculated into brain-heart infusion broth without antibiotics. Broth cultures were grown to optical densities (OD600) between 0.50 and 1.00. *Escherichia coli* strain *S*17-1 λpir containing the pSAM_Bt plasmid was grown to optical densities OD 0.50-1.00. Broth cultures were set up such that between a 5:1 and 10:1 ratio of *P. gingivalis* (recipient) to *E. coli* (donor) was achieved. Although *P. gingivalis* is categorized as an obligate anaerobe it is able to survive without significant CFU loss (less than a log10) for up to 6 hours under aerobic conditions when incubated alone on BAPHK at 37° C.

The *E. coli* donor strain carrying the Mariner transposon on a suicide plasmid vector was conjugated with wild-type *P. gingivalis* using a bi-parental procedure where the *E. coli* donor strain and *P. gingivalis* recipient strain are cultured together on a blood agar plate (trypticase soy agar supplemented with defibrinated sheep's blood (5% vol/vol), hemin (5 µg/ml), and menadione (0.5 µg/ml)) to allow for plasmid transfer. Conjugation was carried out aerobically at 37° C. for 5 hr. As *P. gingivalis* is naturally resistant to gentamicin, this antibiotic was used for selection against the donor *E. coli* following the conjugation. The transposon contains an erythromycin resistance gene (ermG) used to select for *P. gingivalis* transposon insertion mutants.

Construction and Sequencing of Libraries

Genomic DNA eluted in 100 µelution buffer (Qiagen) was placed in a 2 mL microfuge tube and sheared for 2 minutes (10 sec on and 5 sec off duty cycle, 100% intensity) using a high intensity cup horn that was cooled by a circulating bath (4° C.) and was attached to a Branson 450 sonifier. C-tails were then added to 1µg of sheared DNA in a 20 µL reaction that contained 0.5 µL TdT enzyme (Promega), 4 µL 5× TdT reaction buffer (Promega), 475 µM dCTP and 25 µM dideoxy CTP. The dideoxy CTP functions as a chain terminator to limit the length of the poly-C tails. Following a 1-hour incubation at 37° C. and a 20 minute heat-inactivation step at 75° C., dideoxy CTP and other small molecules were removed using a Performa gel filtration cartridge (Edge Biosystems). Transposon containing fragments were then amplified in a 50 µPCR reaction that contained 5 µL C-tailed template, 600 nM C tail-specific primer (olj376 5' GTGACTGGAGTTCAGACGTGTGCTCTTC-CGATCTGGGGGGGGGGGGGGGGG 3') (SEQ ID NO:87), 600 nM transposonspecificprimer (pSAM1 5' CCTGACG-GATGGCCTTT TTGCGTTTCTACC 3') (SEQ ID NO:88), 400 µM dNTPs, 5 µL 10× buffer, and 1 µL Easy-A DNA polymerase mix (Agilent). Sandwiched by an initial incubation at 95° C. for 120 sec and a final extension of 120 sec at 72° C., 24 cycles were completed using 30 sec denaturation steps at 95° C., 30 sec annealing steps at 60° C., and 120 sec extension steps at 72° C. A second PCR reaction was then used to amplify the exact transposon-genomic DNA junction and add additional sequences needed for Illumina® sequencing and indexing. This 50 µreaction contained 1 µL of template from PCR #1, 600 nM transposon endspecific primer (pSAM2 5' AATGATACGGCGACCA CCGA-GATCTACACTCTTTGACCGGGGACTTATCA TCCAACCTGTTA 3') (SEQ ID NO:89), 600 nM indexing primer (5' CA AGCAGAAGACG GCATACGA-GATNNNNNNGTGACT GGAGTTCAGACGTGTG CTCTTCCGATCT 3' (SEQ ID NO:90), where NNNNNN represents the reverse complement of the index and varied with each sample), 400 µM dNTPs, 5 µL 10× buffer, and 1 µL Easy-A DNA Polymerase Mix (Agilent). Sandwiched by an initial incubation at 95° C. for 120 sec and a final extension of 120 sec at 72° C., 12 cycles were completed using 30 sec denaturation steps at 95° C., 30 sec annealing steps at 60° C., and 120 sec extension steps at 72° C.

Libraries were then pooled and run for 51 cycles in a single end sequencing reaction on a single lane of an Illumina® Genome Analyzer II (Tufts University) using the custom sequencing primer pSAM3 (5' ACACTCTTTG ACCGGGGACTTATCATCCAACCTGTTA 3') (SEQ ID NO:91) and the standard Illumina® index sequencing primer.

Data Analysis

Approximately seven-percent of all sequencing reads contained multiple 'C' nucleotides at their 3' end as a consequence of the C-tailing reaction. These C-tails were removed using the "clip adapter sequences script" with the 3' adapter set to CCCCCCCCCCCCCCCCCCCC CCCCCC (SEQ ID NO:92) and the minimum read length set to 26. The resulting clipped reads were aligned to the *P. gingivalis* strain ATCC 33277 and W83 reference genomes, accession numbers AP009380.1 and AE015924.1 respectively, using Bowtie with its default settings. The resulting bowtie output file was then used as input for a custom script, "hopcount." Hopcount tabulates the number of times individual insertion sites in the genome were re-sequenced. An Excel spreadsheet file is generated that indicates, for each insertion site, its position in the genome, gene locus to which that position maps, the strand (positive vs. negative) associated with the site as well as the frequency of its reads. Hopcount output was used to estimate the complexity of transposon libraries and to compare the fate of specific insertions sites in input and output samples. It was also used as input for a second custom script, "aggregate hop table." The output of this script is an excel file in which all transposon insertion sites are tabulated by their collective frequency in each annotated gene of the genome. For each gene, the number of unique insertions sites observed, absolute count of sites in the positive strand, in negative strand and in both strands is recorded. Also recorded is the normalized value dvalgenome, which is an indication of whether the number of insertions observed in that gene is above or below the expected frequency. Dvalgenome equals the observed number of insertions in a gene/predicted number of insertions for that gene and the predicted number of insertions (size of that gene in base pairs divided by size of genome in base pairs) multiplied by (total number of insertions counted).

Other Methods

Bacterial strains and plasmids, media and culture conditions, and bioinformatic resources are as described in Klein, B. et al. 2012.

Example 7

The activities of DNA methyltransferases are important for a variety of cellular functions in bacteria. In this Example, an exemplary embodiment of a homopolymer-mediated nucleic acid amplification method of the invention was used to identify the undermethylated sites in the *Vibrio cholerae* genome for two DNA methyltransferases, Dam, an adenine methyltransferase, and VchM, a cytosine methyltransferase, during growth in rich medium in vitro. Many of the undermethylated sites occurred in intergenic regions, and for most of these sites, the transcription factors responsible for undermethylation were identified (see Dalia, A B, et al. *J Bacteriol.* 2013 May; 195(10):2389-99, incorporated by reference herein in its entirety). This confirmed the presence of previously hypothesized DNA-protein interactions for these transcription factors and provided insight into the biological state of these cells during growth in vitro. DNA adenine methylation has previously been shown to mediate heritable epigenetic switches in gene regulation.

However, none of the undermethylated Dam sites tested showed evidence of regulation by this mechanism. This study is believed to be the first to identify undermethylated adenines and cytosines genome-wide in a bacterium using second-generation sequencing technology.

Identification of Undermethylated Sites in the *V. cholerae* Genome

Figures 1, 9A:
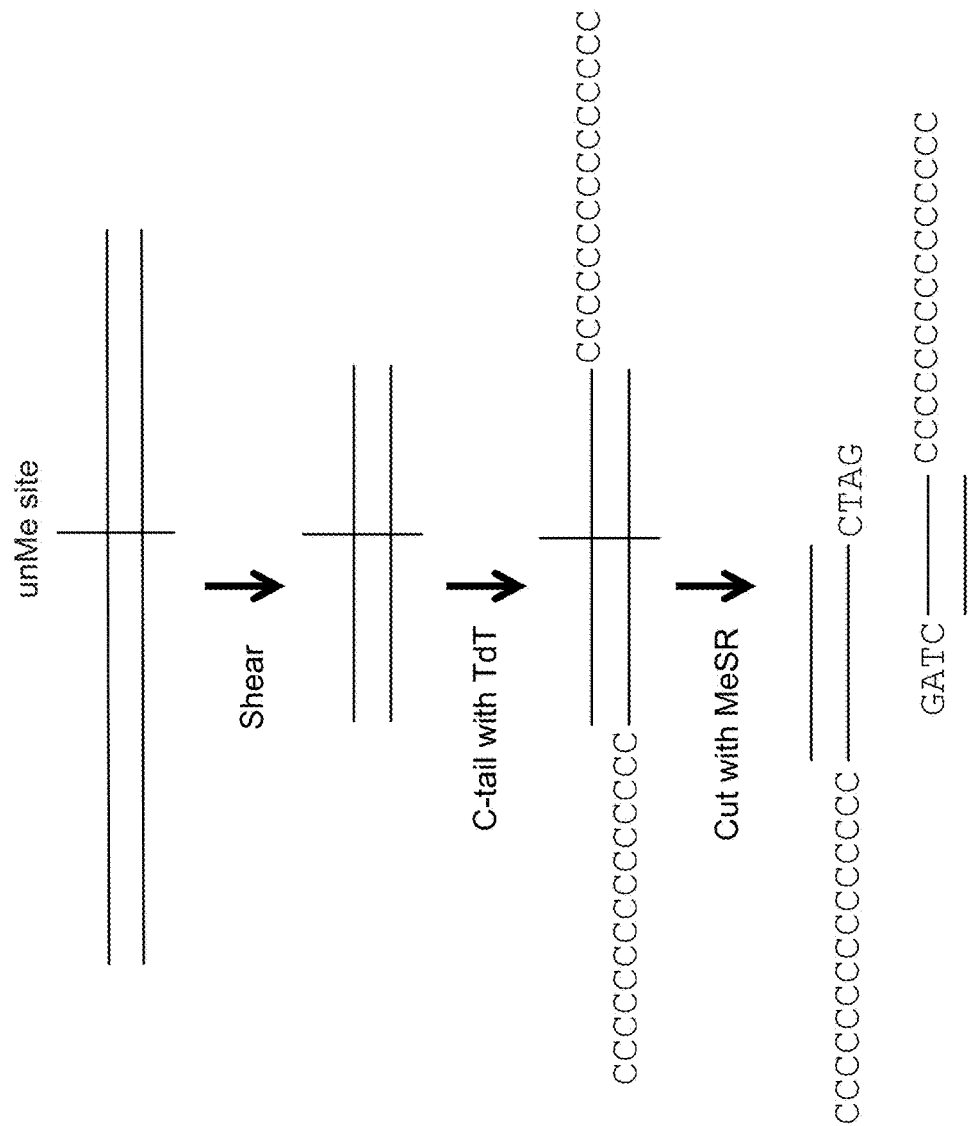
Figures 2, 9A:
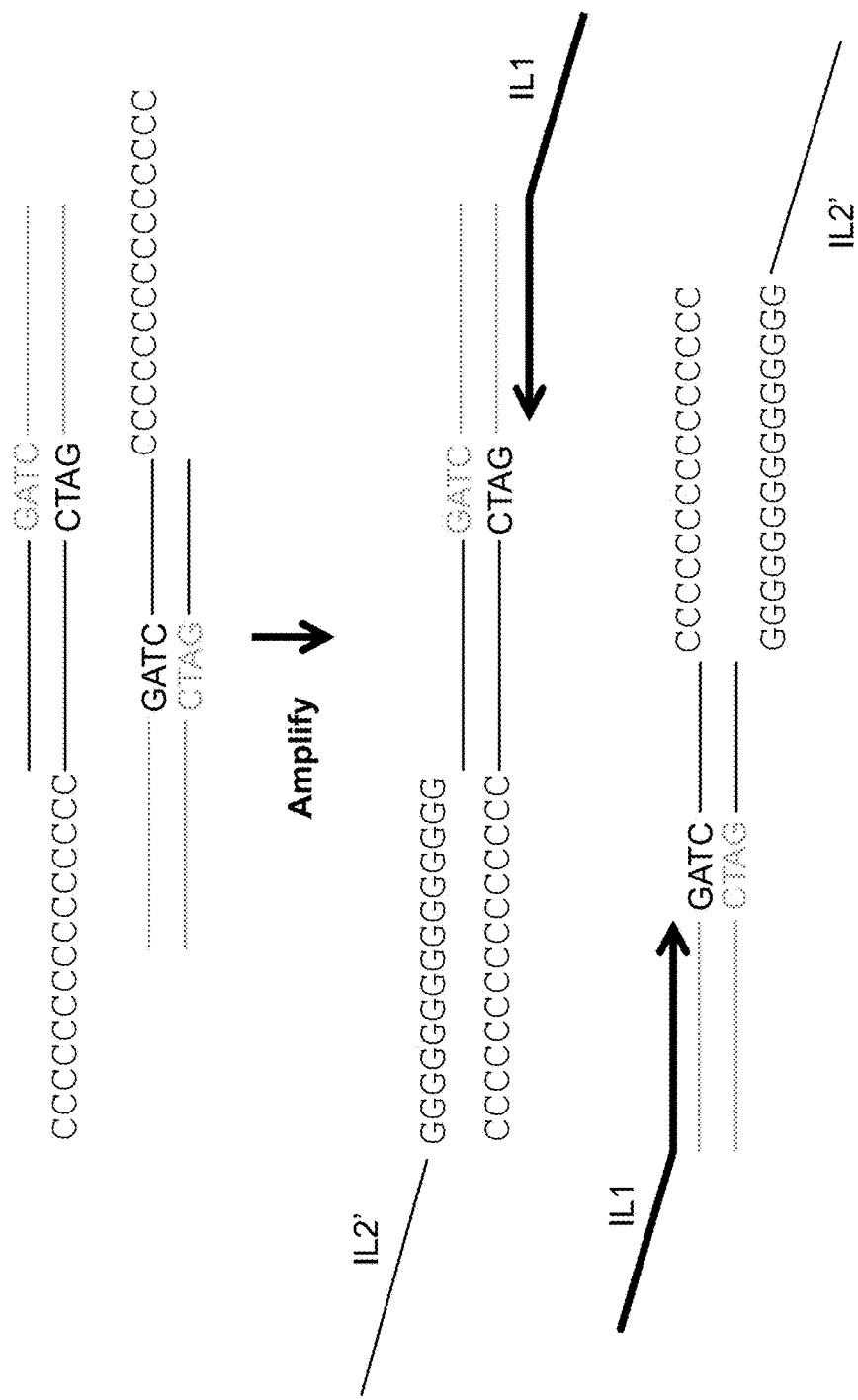

To identify the undermethylated sites in both chromosomes of the *V. cholerae* O1 El Tor strain E7946, the methods of the current Example undertook a high-throughput approach using methylation-sensitive restriction enzymes (MeSR) and next-generation sequencing (NGS). In this study, DNA was first sheared to ~200 to 600 bp, and then homopolymer C-tails were added to the 3' ends of all molecules using terminal deoxynucleotidyl transferase (TdT) (FIG. 9A). Next, a MeSR was used to cut all unmethylated sites, and the cut ends were ligated to an adaptor (tIL1) (FIG. 9A). Once ligated, libraries were amplified using oligonucleotide primers containing the sequences necessary for sequencing on the Illumina® platform (IL-1 and IL-2) (FIG. 9A).

Figure 10:
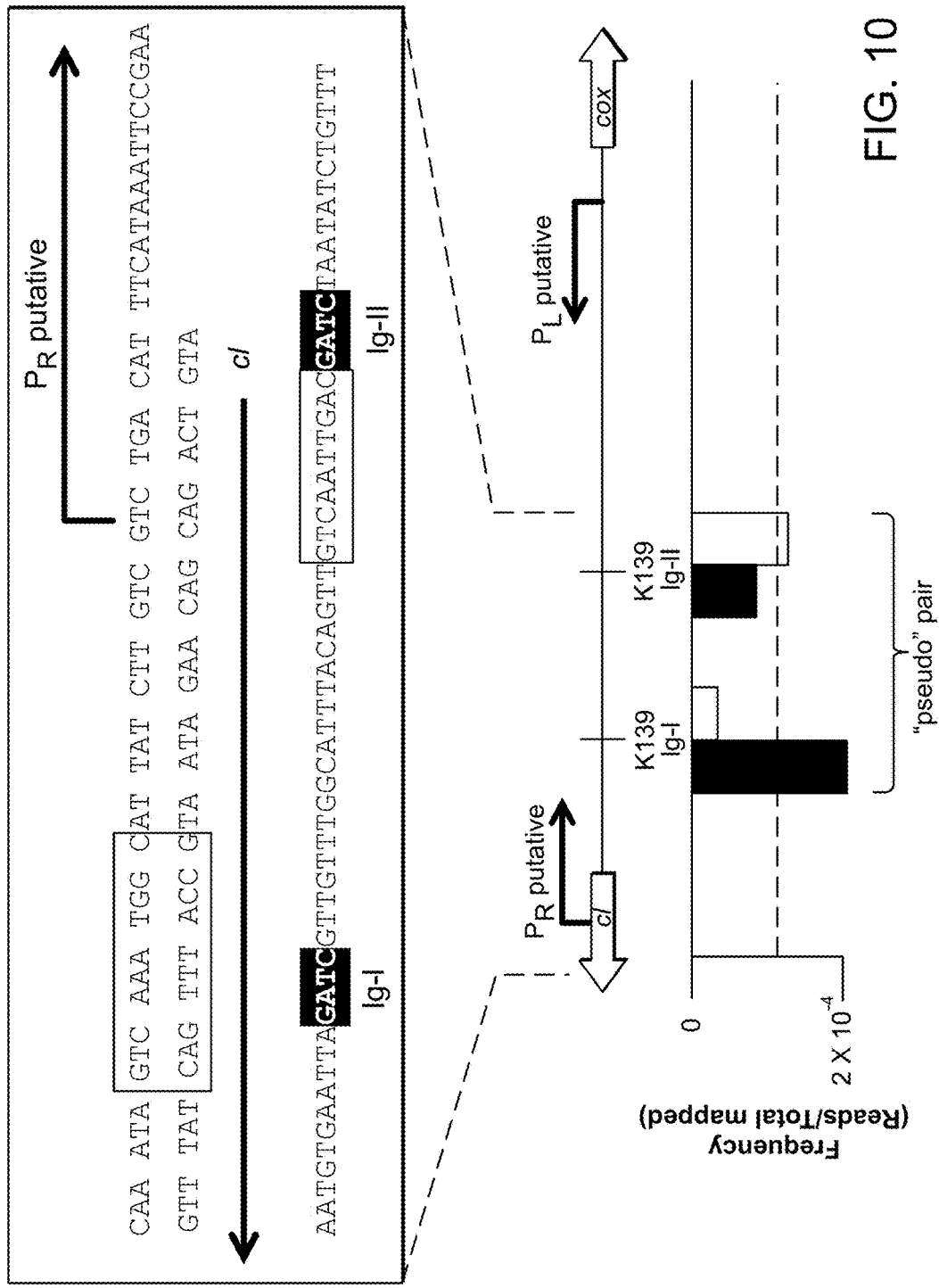
FIG. 10 provides a schematic showing the genetic architecture of undermethylated Dam sites in the K139 prophage.

To assess undermethylation of Dam and VchM sites in *V. cholerae*, the MeSRs MboI and BsrFI, respectively, were used, which perfectly overlap the recognition sites of these two MTases. The undermethylated profile was assessed for these two MTases in cultures grown to late exponential phase in the rich medium lysogeny broth (LB). The late exponential phase represents a phase of growth when nutrient depletion is sensed and major changes in bacterial gene regulation occur. These data sets were mapped to the *V. cholerae* genome. Assessing the graphed frequency of reads mapped along the *V. cholerae* genome, pairs of reads that constitute undermethylated sites were identified (FIGS. 9B to 9E). Frequencies of mapped sequencing reads (y axis) are plotted against the *V. cholera* genome (x axis) for chromosome I (FIGS. 9B and 9D) and chromosome II (FIGS. 9C and 9E). Examples of paired reads that make up a single undermethylated Dam site are highlighted by gray boxes in FIGS. 9B-9E. As a stringent measurement of undermethylated sites, the paired sites (separated by <100 bp) that are above the 99% confidence interval for the mean of the data were determined. Strikingly, there are very few Dam and VchM sites that are undermethylated in the *V. cholerae* genome. Many of the sites that are undermethylated, however, are in intergenic regions, indicating that these are likely due to transcription factor binding (Table V). Specifically for the undermethylated intergenic sites identified in the K139 prophage, this study found that the paired reads are separated by 31 bp, indicating that this site may represent two unmethylated sites in close proximity, which generates a pseudopair. Indeed, upon closer examination of this region, it was found that the outside reads spanning the two Dam sites are overrepresented compared to the inside reads between the two Dam sites, consistent with a model wherein these two sites are undermethylated (FIG. 10). Shown in FIG. 10 is the structure of the intergenic region between the outward-facing genes encoding cI and Cox. Putative PL and PR sites were annotated by Nesper et al. (*J. Bacteriol.* 1999, 181:2902-2913, incorporated by reference herein in its entirety). PL drives the expression of cI, and PR drives the expression of cox. Above the gene layout is a zoomed inset showing the sequence of putative cI operator sites (boxed) and the undermethylated Dam sites Ig-I and Ig-II (highlighted in gray). Below the gene layout is a graph plotting the frequency of mapped reads (y axis) against the genome (x axis) for the two Dam sites in this region from the sequencing data set. Two bars are shown for each Dam site, representing the forward (gray) and reverse (black) reads that result from cleavage of each site. The dotted line on this graph represents the 99% cutoff value used as a measure of significant undermethylation in this experiment.

TABLE V

| Chromosome | Position[a] | Intergenic locus[a] | Frequency[b] | Fold over-representation[c] |
|---|---|---|---|---|
| Dam data | | | | |
| chrI | 1306007 | VC1231-VC1232 | 6.96E_04 | 26.2 |
| chrI | 1306010 | VC1231-VC1232 | 5.74E_04 | 21.6 |
| chrI | 1933145 | VC1783-VC1784 | 3.28E_04 | 12.4 |
| chrI | 1933148 | VC1783-VC1784 | 4.60E_04 | 17.3 |
| chrI | 2364224 | K139p05-K139p04 | 2.02E_04 | 7.6 |
| chrI | 2364255 | K139p05-K139p04 | 1.22E_04 | 4.6 |
| chrII | 68810 | VCA0062-VCA0063 | 3.11E_04 | 11.7 |
| chrII | 68813 | VCA0062-VCA0063 | 1.07E_03 | 40.3 |
| VchM data | | | | |
| chrI | 296268 | VC0286-VC0287 | 1.10E_02 | 47.0 |
| chrI | 296271 | VC0286-VC0287 | 9.66E_03 | 41.4 |
| chrI | 1356851 | VC1280-VC1281 | 5.55E_03 | 23.8 |
| chrI | 1356854 | VC1280-VC1281 | 2.72E_03 | 11.6 |
| chrI | 1670727 | VC1558-VC1559 | 5.27E_03 | 22.6 |
| chrI | 1670730 | VC1558-VC1559 | 3.80E_03 | 16.3 |

[a]The position and locus are based on the annotated N16961 genome containing the K139 prophage genome in chromosome I. The unmethylated site is located in the intergenic region between the indicated loci.
[b]Indicates the frequency of reads mapping to the indicated site relative to the total number of reads mapped.
[c]Indicates the degree of overrepresentation of the reads at the indicated site relative to the mean number of reads obtained for all sites.

Confirmation of Undermethylated Sites by MeSR Digestion and qPCR

To validate and further characterize undermethylated sites, a previously described technique that combines MeSR digestion and qPCR (Oakes C C, et al. *Epigenetics*, 2006, 1:146-152, incorporated by reference herein in its entirety) was used. The gDNA was first digested with a MeSR and, optionally, also with a methylation dependent restriction enzyme (MeDR). Digestion at a site reduces the number of intact template molecules spanning the region. Samples were heat inactivated and then used as the template in a qPCR using oligonucleotide primers that span the methylation site of interest. The relative abundance of DNA in experimental samples was then determined against a standard curve, and the percentage of undermethylation was determined relative to the undigested control. To characterize the undermethylation of Dam sites, the MeSR MboI and the MeDR DpnI were used, and to characterize the undermethylation of VchM sites, the MeSR MspI was used.

Figure 11:
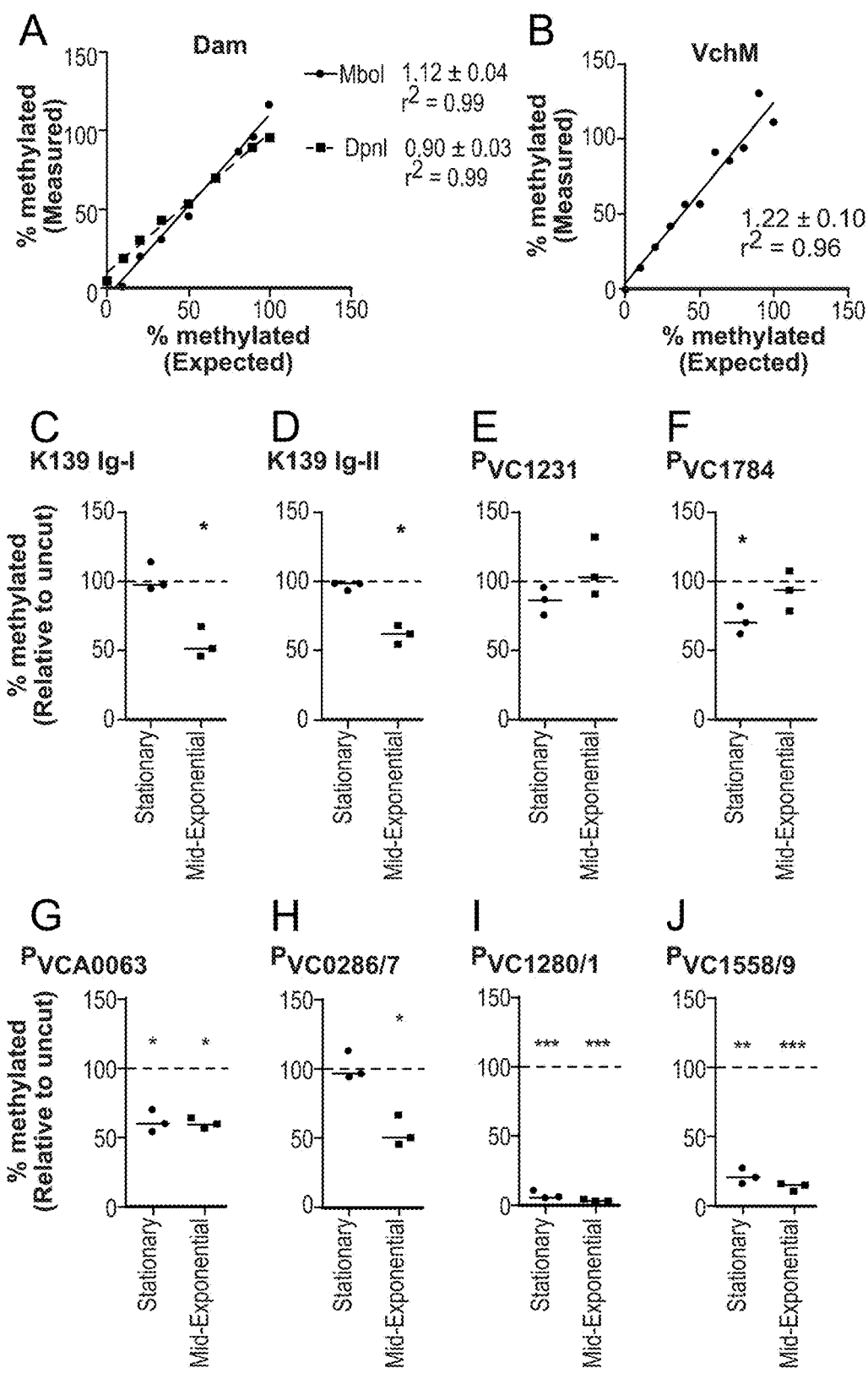
FIGS. 11A-11J provide graphs showing a characterization of intergenic undermethylated sites by MeSR digestion and qPCR; *, P<0.05; , P<0.01; *, P<0.001.

To confirm that this method yields a quantitative assessment of methylation status, two control experiments were performed. *E. coli* Dam+ (methylase-expressing) and Dam− (methylase-null mutants) gDNA(KEIO collection strains (Baba T, et al. *Mol. Syst. Biol.*, 2006, 2:2006-08)) were mixed at different ratios, ranging from 100% to 0% Dam+ in 10% increments, and subjected to the method described below. The experimentally derived values (measured) for percentage of unmethylated DNA were compared to the actual values (expected), and, as expected, both the MboI (solid line) and DpnI (dotted line) data showed linearity over this range, with slopes near 1 (FIG. 11A: the experimental values obtained (Measured) were compared to actual mixed ratios (Expected)). Thus, subsequent data for Dam undermethylation were assessed by MboI digestion alone. The same analysis was performed using mixtures of wild-type E7946 and AvchM mutant strain gDNA to validate the assay using the MeSR MspI. Again, as expected, the data show linearity over the range of ratios tested, with a slope near 1 (FIG. 11B). The data in FIG. 11B are shown as percent methylated relative to an uncut control reaction mixture. The slope of the linear regression standard error is indicated. The data in FIG. 11B are representative results from one of at least two independent experiments.

Using this method, extension of the analysis of the undermethylated sites identified as described above to cells grown to either mid-exponential or stationary phases was performed. FIGS. 11C-11J provide a characterization of Dam (FIGS. 11C to 11G) and VchM (11H to 11J) undermethylated intergenic sites using MeSR digestion and qPCR of gDNA from cultures grown to mid-exponential (optical density at 600 nm (OD600) of 0.5) or stationary (OD600, 3.0) phase. All sites assessed were significantly undermethylated in either mid-exponential, stationary, or both phases, except for PVC1231, which trended toward undermethylation in stationary phase but not to a statistically significant degree (FIGS. 11C-11J). Data are shown as percent methylated relative to an uncut control reaction mixture, and significance was determined by one-sampled Student's t test to determine if means were significantly different from 1. Each data point in FIGS. 11C to 11J represents an independent biological replicate, and a horizontal line represents the median of each sample.

Methods

Methyl Homopolymer Tail Mediated Sequencing

Genomic DNA (gDNA) was isolated using the DNeasy blood and tissue kit (Qiagen) according to the manufacturer's instructions. After isolation, between 1 and 2 µg of gDNA was sheared to ~400 bp (range 200 to 600 bp) using a pre-chilled Branson high-intensity cup horn sonifier (Branson) for 2 min at 50% intensity with a 5-s-on/5-s-off duty cycle. Homopolymer tails of cytosine were added to the 3' ends of all sheared molecules using terminal deoxynucleotidyl transferase (TdT) according to the manufacturer's instructions (Promega). For these reactions, a 20:1 mixture of dCTP and ddCTP (a chain terminator) was used to generate C-tails of approximately 20 cytosines. After C-tailing, reaction mixtures were run through a Performa spin column (Edge Biosystems), according to the manufacturer's instructions, to remove excess nucleotides and to desalt reaction mixtures. The eluate was digested using the appropriate methylation-sensitive restriction enzyme (MeSR). For Dam, the MeSR used was MboI, while for VchM, the MeSR used was BsrFI (New England BioLabs). After digestion, samples were heat inactivated when appropriate and run through a Performa spin column to desalt reactions. The eluate was then ligated to the tIL1 adaptor (final concentration of 1 µM) using the Quick Ligase kit (New England BioLabs), in a ligation mixture volume of 60 µl, according to the manufacturer's instructions. The tIL1 adaptor was generated by annealing the oligonucleotides ABD013 and ABD013D for Dam and ABD013 and ABD013B for VchM. Samples were run through a Performa spin column to desalt reaction mixtures. Then, 6 µl of the eluate was used as the template in PCRs to amplify the samples, using OLJ 131 as the forward primer and either OLJ 573 (Dam) or BC33G (VchM) as the reverse primer. These forward and reverse primers contain the sequences specific for capture and sequencing on the Illumina® HiSeq2000 platform (Illumina). Also, the reverse primers used provide a unique barcode index sequence that can be used to multiplex samples onto a single lane in the Illumina® flow cell. After PCR, the DNA concentrations of samples were determined on a Nanodrop 2000 spectrophotometer (Nanodrop) and submitted for sequencing via single-end 50-bp reads on the Illumina® HiSeq2000.

After sequencing and de-multiplexing, reads were further filtered to identify sequences that represent true Dam and VchM sites. For Dam data, reads were filtered to obtain sequences that started with GATC (SEQ ID NO:93), while for the VchM data, reads were filtered to obtain sequences that started with either CCGGC (SEQ ID N0:94) or CCGGT (SEQ ID NO:95). The reads were then trimmed to a length of 21 bp and mapped to the O1 El Tor N16961 genome containing the sequence for the K139 prophage inserted into chromosome I (this prophage sequence is absent from N16961 but present in the E7946 strain used in this study (Reidl J, et al. *Mol. Microbiol.* 1995, 18:685-701)), using the program Bowtie, and no mismatches were allowed during mapping (Langmead B, et al. *Genome Biol.*, 2009, 10:R25.). Finally, the total numbers of forward and reverse reads mapping to methylation sites were determined.

MeSR Digestion and qPCR for Characterization of Undermethylated Sites

Assays were performed essentially as previously described (Oakes C C, et al. *Epigenetics*, 2006, 1:146-152). Briefly, between 10 and 100 ng of gDNA was digested using a MeSR in a final reaction mixture volume of 20 pl. For Dam, the MeSR used was MboI, while for VchM, the MeSR used was MspI. After digestion, reaction mixtures were heat inactivated when appropriate. Then, 2 µl of this digestion (1 to 10 ng) was used as the template for quantitative PCR (qPCR) using primers that span a methylation site of interest. An uncut control reaction mixture (no-enzyme control) was run for every sample. The abundance of DNA in all samples was determined relative to a standard curve generated using dilutions of purified gDNA. Reaction mixtures were run on an Mv3005P qPCR instrument (Stratagene) using the dye incorporation method (SYBR green) and analyzed using MxPro qPCR software (Stratagene).

Other Methods

Bacterial strains and culture conditions for this study are described in Dalia et al., 2013. Generation of mutant strains, analysis of transcript abundance, and statistical analyses were performed as described in Dalia et al. 2013.

Example 8

In this Example, an exemplary embodiment of a homopolymer-mediated nucleic acid amplification method of the invention was used in combination with Tn-seq to monitored changes in the composition of a mixed population of *Borrelia burgdorferi* (*B. burgdorferi*) transposon mutants with insertions into the same gene to identify where *B. burgdorferi* encounters barriers to mouse infection. More specifically, homopolymer-mediated nucleic acid amplification was used as a method to facilitate amplification of the genomic DNA flanking transposons.

*Borrelia burgdorferi* is an invasive spirochete that can cause acute and chronic infections in the skin, heart, joints and central nervous system of infected mammalian hosts. Little is understood about where the bacteria encounter the strongest barriers to infection and how different components of the host immune system influence the population as the infection progresses. Both wild-type mice and mice lacking the Toll-like receptor adapter molecule MyD88 were infected with a pool of infectious *B. burgdorferi* transposon mutants with insertions in the same gene. At multiple time points post-infection, bacteria were isolated from the mice and the compositions of the *B. burgdorferi* populations at the injection site and in distal tissues determined. A population bottleneck was identified at the site of infection that significantly altered the composition of the population (Troy, E. B., et al. *Infection and Immunity,* 2013, 81(7):2347, incorporated by reference herein in its entirety). The magnitude of this bottleneck was reduced in MyD88$^{-/-}$ mice, indicating a role for innate immunity in limiting early establishment of *B. burgdorferi* infection. There is not a significant bottleneck during the colonization of distal tissues, suggesting that founder effects are limited and there is not a strict limitation on the number of organisms able to initiate populations at distal sites. These findings further the understanding of the interactions between *B. burgdorferi* and its murine host in the establishment of infection and dissemination of the organism.

Figure 12:
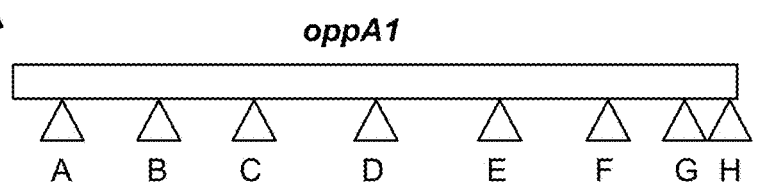
FIGS. 12A-12C provide graphs of data demonstrating the reproducibility of the Tn-seq technique.
Figure 12:
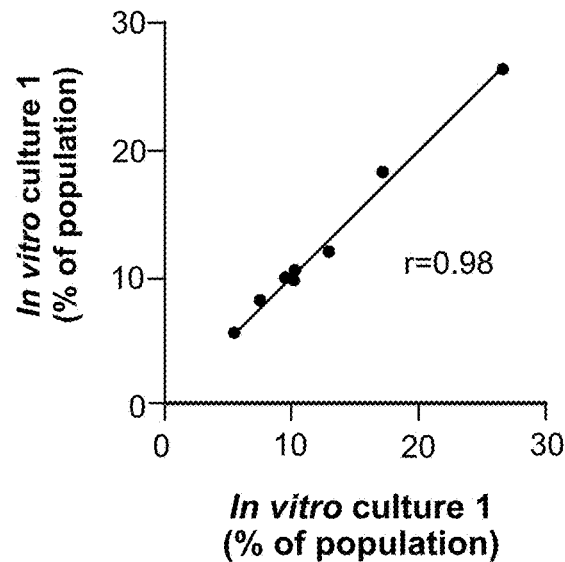
Figure 12:
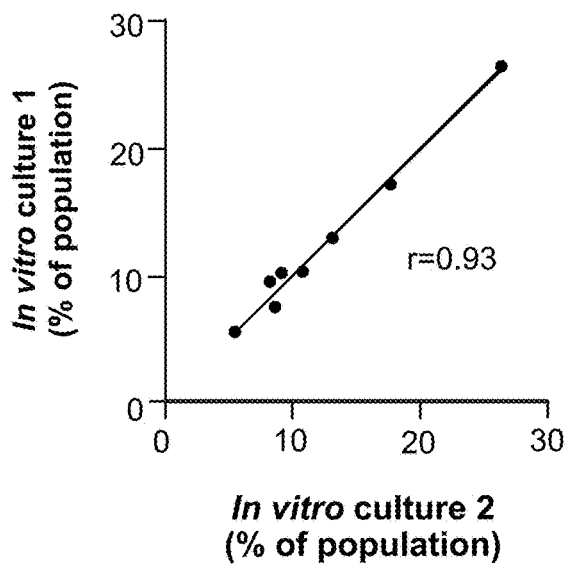

High-throughput Sequencing to Study *Borrelia burgdorferi* During Mouse Infection The basis of Tn-seq is to use massively parallel sequencing to determine the frequency of individual transposon mutants within a population (van Opijnen T, et al. *Nat. Methods,* 2009, 6:767-772). Lin et al. have created a library of defined transposon mutants of *B. burgdorferi* (Lin T, et al. *PLoS One,* 2012, 7:e47532). Mice were infected with a mixed population of transposon mutants from this library and Tn-seq was used to monitor changes in the composition of the population as the infection progressed. To minimize changes in population composition due to differences in infectivity, a set of eight transposon mutants with insertions in different sites of a single gene, oppA1, which encodes oligopeptide permease 1 (OppA1) was used. OppA1 is a periplasmic binding substrate for the oligopeptide permease OppA (Wang X G, et al. *J. Bacteriol.,* 2004, 186:51-60; Lin B, et al. *Biochim. Biophys. Acta,* 2001, 1499:222-231). The gene is located on the chromosome upstream of two genes encoding alternate substrate binding proteins, oppA2 and oppA3. Expression of the three genes occurs through independent transcription (Wang X G, et al. *J. Bacteriol.,* 2002, 184:6198-6206.). It has previously been shown that strains of *B. burgdorferi* lacking oppA1, oppA2, and/or oppA3 have no growth defects in vitro and no attenuation of infectivity in mice, likely due to functional redundancy between the OppA proteins (Lin T, et al. 2012, Lin T, et al. 2001). The DNA sequences of the genomic DNA flanking the transposon in each of the oppA1 insertions mutants could be easily differentiated from each other. The eight strains are referred to as mutants A through H (FIG. 12A.

To validate Tn-seq for use in *B. burgdorferi,* biological and technical replicates were performed using mixed in vitro cultures of the eight oppA1 mutants. When tested individually in vitro, no growth defects were observed in any of the mutants. For the Tn-seq, individual cultures of each mutant were mixed at known concentrations. Biological replicates were performed by dividing the mixture into two and growing independent cultures for 4 days. Libraries for sequencing were generated from each of the cultures. Technical replicates were performed by preparing two sequencing libraries from a single genomic DNA isolation. The frequencies obtained for each mutant from the sequencing data agreed with the frequency of each mutant in the original mixed culture. Reproducibility between the technical replicate (FIG. 12B) and biological replicates (FIG. 12C) was high. This confirmed the accuracy and reproducibility of Tn-seq for determining the relative frequency of individual *B. burgdorferi* mutants within a mixed population.

For mouse studies, the oppA1 insertion mutants were mixed in equal amounts. The 50% infectious dose (ID50) of *B. burgdorferi* has been reported to be between 83 and 8,000 organisms (Kawabata H, et al. *Infect. Immun.,* 2004, 72:7147-7154; Pitzer J E, et al. *Infect. Immun.,* 2011, 79:1815-1825; Sultan S Z, et al. *Infect. Immun.,* 2011, 79:3273-3283; Tilly K, et al. *Infect. Immun.,* 2006, 74:3554-3564, each of which is incorporated by reference herein). To ensure that each strain was present at a sufficient dose to establish infection, mice were inoculated with $1\times10^4$ bacteria of each insertion, for a total dose of $8\times10^4$. A portion of the inoculum was diluted and passaged in vitro to confirm that any changes in the composition of the population following mouse infection were not due to a general growth defect. At 3 days, 2 weeks, and 6 weeks post-infection, groups of infected mice were sacrificed and tissues commonly associated with Lyme disease, the tibiotarsal joints, knees, hearts, and skin at the inoculation site, were excised and cultured in BSK-II medium. At 3 days post-infection, *B. burgdorferi* had not disseminated and was detected only at the inoculation site of the mice, with the exception of one knee sample. By 2 weeks post-infection, the bacteria had disseminated throughout the infected mice and could be detected in multiple tissues. At 6 weeks post-infection, bacteria could still be detected in all tested organs. Organ culture expanded the population of the bacteria used to create the sequencing library, thus increasing the limit of detection for identifying minor members of the population. Furthermore, this growth step reduced the amount of eukaryotic DNA in the sample, which could decrease the efficiency of the library preparation. However, as a result, direct measurement of total bacterial loads in the tissues could not be performed. Sequencing libraries were prepared from the organ cultures when the bacteria reached late exponential phase. *B. burgdorferi* populations from the original inoculum mix, the passaged cultures, and the organ cultures were subjected to Tn-seq. Similar to the in vitro culture results, reproducibility was high in technical replicates from the organ cultures.

Methods

Construction and Sequencing of Libraries

Genomic libraries for sequencing were constructed as described by Klein et al. (*BMC Genomics,* 2012, 13:578). Genomic DNA was obtained from the frozen pellets using a DNeasy blood and tissue kit (Qiagen, Valencia, Calif.) per the manufacturer's instructions. An aliquot of the DNA was placed in a 2-ml microcentrifuge tube and sheared by sonication for 2 min (duty cycle, 10 s on and 5 s off; intensity, 100%) using a high-intensity cup horn that was cooled by a circulating bath (4° C.) and attached to a Branson 450 Sonifier. To facilitate amplification of the genomic DNA flanking the transposon, cytosine tails (C tails) were added to 1 µg sheared DNA using terminal deoxynucleotidyl transferase (TdT) (Promega, Madison, Wis.). The TdT reaction mixture contained 475 µM dCTP and 25 µM ddCTP (Affymetrix/USB Products, Santa Clara, Calif.) to limit the length of the C tail. The reaction mixture was incubated for 1 h at 37° C. followed by 20 min at 75° C. The DNA was then purified using a Performa gel filtration cartridge (Edge Biosystems). Transposon-containing fragments were amplified in a PCR mixture containing 5 µl DNA from the TdT reaction as the template and primers specific to the ColE1 site on the 5' end of the transposon (pMargent1, 5' CGGCAAGTTCATCC TTAGGAG ACCGGGG 3') (SEQ ID NO:96) and the C tail (olj376, 5' GTGACTG-GAGTTCAGACGTGT GCTCTTC-CGATCTGGGGGGGGGGGGGGGGG 3') (SEQ ID NO:97). Primer olj376 was added at three times in excess of pMargent1. The reactions were carried out using Easy-A DNA polymerase (Agilent Technologies, Santa Clara, Calif.) with an initial incubation of 2 min at 95° C. followed by 24 cycles of 30 s at 95° C., 30 s at 60° C., and 2 min at 72° C. followed by a 2-min extension at 72° C. To prepare the DNA for sequencing and amplify the exact transposon-genomic DNA junction, a nested PCR was performed using 1 µl of the original PCR as a template and a primer specific to the transposon end (pMargent2, 5' AATGATACGGCGACCA CCGAGATCT ACACTCTTTCCGGGGACTTATCAGCC AACCTGTTA 3') (SEQ ID NO:98) and an indexing primer (5' CAAGCAGAAGACGGCA TACGAGATNNNNNNGT-GAC TGGAGTTCAGACGTGTGCTCTTCCGATCT 3') (SEQ ID NO:99), containing the specific sequences required for sequencing on an Illumina® platform and where NNNNNN represents a six-base-pair barcode sequence allowing samples to be multiplexed in a single sequencing lane. Within an experiment, a unique indexing primer was used for each individual *B. burgdorferi* culture. Reactions were carried out using Easy-A DNA polymerase with an initial incubation of 2 min at 95° C. followed by 15 cycles of 30 s at 95° C., 30 s at 60° C., and 2 min at 72° C. followed by a 2-min extension at 72° C. PCR products were purified using a QIAquick PCR purification kit (Qiagen, Valencia, Calif.). A majority of the PCR products were between 200 bp and 600 bp. The libraries made from each culture were then pooled at equal concentrations. The pooled libraries were sequenced on an Illumina® Genome Analyzer II as 50-bp single-end reads using the custom sequencing primer pMargent3 (5' ACACTCTTTCCGGGGACT TATCAGC-CAACCT GTTA 3') (SEQ ID NO:100) and the standard Illumina® index primer.

Data Analysis

Image analysis, base calling, and base call quality were generated automatically during the sequencing run with Illumina® Real Time Analysis (RTA) 1.13.48.0 software. Sequenced reads were split according to barcode sequence with the Illumina® Casava 1.8.2 pipeline to generate a fastq file for each sample. The number of sequence reads obtained from the culture of each tissue ranged from $3.5 \times 10^6$ to $6.3 \times 10^6$, with an average of $4.8 \times 10^6$ reads. Subsequent data analysis was done using the Galaxy platform (Giardine B, et al. *Genome Res.*, 2005, 15:1451-1455; Goecks J, et al. *Genome Biol.*, 2010, 11:R86; Blankenberg D, et al. *Curr. Protoc. Mol. Biol.*, 2010, 19:19). The C tail was removed from the sequence reads, and reads shorter than 30 by were discarded. The remaining reads were filtered for quality. Reads for which 90% of the cycles did not have a quality of greater than 15 were discarded. The remaining reads were aligned to the *B. burgdorferi* B31 genome using Bowtie with its default settings. A custom script was then used to compile the resulting SAM alignment file into a list of individual insertion sites with the number of reads aligned to each site.

Other Methods

Bacterial strains and growth medium are as described in Troy, E. B., et al. 2013. Creation of oppA1 insertion mutants, animal studies and statistical analyses are also as described in Troy, E. B., et al. 2013.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and "consisting essentially of shall be closed or semi-closed transitional phrases, respectively, as set forth in the United States Patent Office Manual of Patent Examining Procedures, Section 2111.03.

What is claimed is:

1. A method, comprising
   (a) adding a first homopolymer of at least 12 nucleotides to the 3' end of each nucleic acid strand of a blunt-ended double-stranded nucleic acid containing a target nucleic acid by combining in a single reaction vessel the blunt-ended double-stranded nucleic acid, terminal deoxynucleotidyl transferase (TdT), deoxynucleotide triphosphate (dNTP), and a chain terminator, wherein the ratio of dNTP to chain terminator is at least 11 to 1, thereby producing a partially double-stranded nucleic acid having a homopolymer of at least 12 nucleotides at each 3' end; and
   (b) adding a second homopolymer of at least 4 nucleotides to the 5' end of each strand of the partially double-stranded nucleic acid, wherein the second homopolymer is attached at its 5' end to a first oligonucleotide and is shorter than and complementary to the first homopolymer.

2. The method of claim 1, wherein the second homopolymer of at least 4 nucleotides is added to the 5' end of each nucleic acid strand of the partially double-stranded nucleic acid by combining in a single reaction vessel the partially double-stranded nucleic acid, ligase, and the second homopolymer attached to the first oligonucleotide under conditions that permit ligation.

3. The method of claim 1, further comprising amplifying the target nucleic acid by polymerase chain reaction using a first primer and a second primer,
   wherein the first primer comprises, from 5' to 3', (a) a second oligonucleotide that is the same as the first oligonucleotide and (b) a third homopolymer that is the same as the second homopolymer, and wherein the second primer comprises, from 5' to 3', (c) a third oligonucleotide that is different from the first and second oligonucleotides, and (d) a fourth homopolymer that is complementary to the first homopolymer, wherein the fourth homopolymer is longer than the second homopolymer.

4. The method of claim 3, wherein the fourth homopolymer contains at least 12 nucleotides.

5. The method of claim 1, wherein the first homopolymer contains deoxycytosine nucleotides or deoxyguanosine nucleotides.

6. The method of claim 1, wherein the second homopolymer contains deoxycytosine nucleotides or deoxyguanosine nucleotides.

7. The method of claim 3, wherein the third homopolymer and the fourth homopolymer each contains deoxycytosine nucleotides or deoxyguanosine nucleotides.

8. The method of claim 1, wherein the first homopolymer is about 15 to about 30 nucleotides in length.

9. The method of claim 1, wherein the first oligonucleotide contains a restriction endonuclease recognition site, a recombination site, or a promoter for in vitro transcription.

10. The method of claim 1, wherein the chain terminator is a dideoxynucleotide (ddNTP).

11. The method of claim 10, wherein the dideoxynucleotide is ddCTP, ddGTP or ddATP.

12. The method of claim 10, wherein the ratio of dNTP to ddNTP is about 11 to 1 to about 29 to 1.

13. A method, comprising:
(a) adding a first homopolymer of at least 12 nucleotides to the 3' end of each nucleic acid strand of a blunt-ended double-stranded nucleic acid containing, from 5' to 3', a known target region contiguous with an unknown target region, by combining in a single reaction vessel the blunt-ended double-stranded nucleic acid, terminal deoxynucleotidyl transferase (TdT), deoxynucleotide triphosphate (dNTP), and a chain terminator, wherein the ratio of dNTP to chain terminator is at least 11 to 1, thereby producing a first partially double-stranded nucleic acid having a homopolymer of at least 12 nucleotides at each 3' end; and
(b) amplifying the known and unknown target regions by polymerase chain reaction using a first primer and a second primer, wherein the first primer contains, from 5' to 3', a first oligonucleotide and a second oligonucleotide that is the same as at least a portion of the known target region; and the second primer contains, from 5' to 3', a second oligonucleotide different from the first oligonucleotide, and a second homopolymer complementary to the first homopolymer.

* * * * *

SEQUENCE LISTING

```
<160> NUMBER OF SEQ ID NOS: 100

<210> SEQ ID NO 1
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 1
gatcggaaga gctcgtatgc cgtcttctgc ttg                                33

<210> SEQ ID NO 2
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 2
aatgatacgg cgaccaccga gatctacact ctttccctac acgacgctct tccgatct    58

<210> SEQ ID NO 3
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 3
caagcagaag acggcatacg agctcttccg atct                              34

<210> SEQ ID NO 4
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 4
acactctttc cctacacgac gctcttccga tct                               33

<210> SEQ ID NO 5
<211> LENGTH: 20
<212> TYPE: DNA
<213> ORGANISM: Artificial Sequence
<220> FEATURE:
```

<223> OTHER INFORMATION: Synthetic polynucleotide

<400> SEQUENCE: 5
gatcggaaga gcacacgtct                                           20

<210> SEQ ID NO 6
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 6
acactctttc cctacacgac gctcttccga tct                            33

<210> SEQ ID NO 7
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 7
aatgatacgg cgaccaccga gatctacact ctttccctac acgacgctct tccgatct  58

<210> SEQ ID NO 8
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 8
gtgactggag ttcagacgtg tgctcttccg atct                           34

<210> SEQ ID NO 9
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 9
acactctttc cctacacgac gctcttccga tct                            33

<210> SEQ ID NO 10
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 10
gatcggaaga gcacacgtct gaactccagt cac                            33

<210> SEQ ID NO 11
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 11
gtgactggag ttcagacgtg tgctcttccg atct                           34

<210> SEQ ID NO 12
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 12
caagcagaag acggcatacg agatcgtgat gtgactggag ttc                        43

<210> SEQ ID NO 13
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 13
caagcagaag acggcatacg agatacatcg gtgactggag ttc                        43

<210> SEQ ID NO 14
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 14
caagcagaag acggcatacg agatgcctaa gtgactggag ttc                        43

<210> SEQ ID NO 15
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 15
caagcagaag acggcatacg agattggtca gtgactggag ttc                        43

<210> SEQ ID NO 16
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 16
caagcagaag acggcatacg agatcactgt gtgactggag ttc                        43

<210> SEQ ID NO 17
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 17
caagcagaag acggcatacg agatattggc gtgactggag ttc                        43

<210> SEQ ID NO 18
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 18
caagcagaag acggcatacg agatgatctg gtgactggag ttc            43

<210> SEQ ID NO 19
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 19
caagcagaag acggcatacg agattcaagt gtgactggag ttc            43

<210> SEQ ID NO 20
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 20
caagcagaag acggcatacg agatctgatc gtgactggag ttc            43

<210> SEQ ID NO 21
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 21
caagcagaag acggcatacg agataagcta gtgactggag ttc            43

<210> SEQ ID NO 22
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 22
caagcagaag acggcatacg agatgtagcc gtgactggag ttc            43

<210> SEQ ID NO 23
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 23
caagcagaag acggcatacg agattacaag gtgactggag ttc            43

<210> SEQ ID NO 24
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 24
gatcggaaga gcggttcagc aggaatgccg ag            32

<210> SEQ ID NO 25
<211> LENGTH: 33

```
<212> TYPE: DNA
<213> ORGANISM: Artificial Sequence
<220> FEATURE:
<223> OTHER INFORMATION: Synthetic polynucleotide

<400> SEQUENCE: 25
acactctttc cctacacgac gctcttccga tct                           33

<210> SEQ ID NO 26
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 26
aatgatacgg cgaccaccga gatctacact ctttccctac acgacgctct tccgatct    58

<210> SEQ ID NO 27
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 27
gatcgtcgga ctgtagaact ctgaac                                   26

<210> SEQ ID NO 28
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 28
acaggttcag agttctacag tccgac                                   26

<210> SEQ ID NO 29
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(23)
<223> OTHER INFORMATION: n is a, c, g, or t

<400> SEQUENCE: 29
caagcagaag acggcatacg ann                                      23

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 30
tcgtatgccg tcttctgctt g                                        21

<210> SEQ ID NO 31
<211> LENGTH: 21
<212> TYPE: DNA
<213> ORGANISM: Artificial Sequence
<220> FEATURE:
```

<223> OTHER INFORMATION: Synthetic polynucleotide

<400> SEQUENCE: 31
caagcagaag acggcatacg a                                      21

<210> SEQ ID NO 32
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 32
aatgatacgg cgaccaccga caggttcaga gttctacagt ccga             44

<210> SEQ ID NO 33
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 33
cgacaggttc agagttctac agtccgacga tc                          32

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
tcggactgta gaactctgaa c                                      21

<210> SEQ ID NO 35
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 35
acaggttcag agttctacag tccgacatg                              29

<210> SEQ ID NO 36
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(23)
<223> OTHER INFORMATION: n is a, c, g, or t

<400> SEQUENCE: 36
caagcagaag acggcatacg ann                                    23

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37
tcgtatgccg tcttctgctt g                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 38
caagcagaag acggcatacg a                                              21

<210> SEQ ID NO 39
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 39
aatgatacgg cgaccaccga caggttcaga gttctacagt ccga                     44

<210> SEQ ID NO 40
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 40
ccgacaggtt cagagttcta cagtccgaca tg                                  32

<210> SEQ ID NO 41
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 41
caagcagaag acggcatacg a                                              21

<210> SEQ ID NO 42
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 42
guucagaguu cuacaguccg acgauc                                         26

<210> SEQ ID NO 43
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (23)..(23)
<223> OTHER INFORMATION: n is inverted dT or ddT

<400> SEQUENCE: 43
ucguaugccg ucuucugcuu gun                                            23

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44
caagcagaag acggcatacg a                                          21

<210> SEQ ID NO 45
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 45
aatgatacgg cgaccaccga caggttcaga gttctacagt ccga                 44

<210> SEQ ID NO 46
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 46
cgacaggttc agagttctac agtccgacga tc                              32

<210> SEQ ID NO 47
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 47
aatgatacgg cgaccaccga gatctacact ctttccctac acgacgctcg ggggggg    56

<210> SEQ ID NO 48
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 48
acactctttc cctacacgac gctcgggggg g                               31

<210> SEQ ID NO 49
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 49
caagcagaag acggcatacg agataaaaaa gtgactggag ttcagacgtg tgctcttccg    60 atctggggggg gggggggggg                                               80

<210> SEQ ID NO 50
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 50
caagcagaag acggcatacg agatacacac gtgactggag ttcagacgtg tgctcttccg    60
atctgggggg gggggggggg                                                80

<210> SEQ ID NO 51
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 51
caagcagaag acggcatacg agatagagag gtgactggag ttcagacgtg tgctcttccg    60 atctggggggg gggggggggg                                               80

<210> SEQ ID NO 52
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 52
caagcagaag acggcatacg agatatatat gtgactggag ttcagacgtg tgctcttccg    60 atctggggggg gggggggggg                                               80

<210> SEQ ID NO 53
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 53
caagcagaag acggcatacg agatcacaca gtgactggag ttcagacgtg tgctcttccg    60 atctggggggg gggggggggg                                               80

<210> SEQ ID NO 54
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 54
ccaaaatccg ttccttttc atagttccta tatagttata cgc                       43

<210> SEQ ID NO 55
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 55
gtgactggag ttcagacgtg tgctcttccg atctggggggg gggggggggg              50

<210> SEQ ID NO 56
<211> LENGTH: 62
<212> TYPE: DNA

```
<213> ORGANISM: Artificial Sequence
<220> FEATURE:
<223> OTHER INFORMATION: Synthetic polynucleotide

<400> SEQUENCE: 56
aatgatacgg cgaccaccga gatctacact ctttgaccgg ggacttatca gccaacctgt    60
ta                                                                  62

<210> SEQ ID NO 57
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 57
acactctttg accggggact tatcagccaa cctgtta                             37

<210> SEQ ID NO 58
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 58
caagcagaag acggcatacg agatcgtgat gtgactggag ttcagacgtg tgctcttccg    60
atct                                                                64

<210> SEQ ID NO 59
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 59
caagcagaag acggcatacg agatacatcg gtgactggag ttcagacgtg tgctcttccg    60
atct                                                                64

<210> SEQ ID NO 60
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 60
caagcagaag acggcatacg agatgcctaa gtgactggag ttcagacgtg tgctcttccg    60
atct                                                                64

<210> SEQ ID NO 61
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 61
caagcagaag acggcatacg agattggtca gtgactggag ttcagacgtg tgctcttccg    60
atct                                                                64
```

```
<210> SEQ ID NO 62
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 62
caagcagaag acggcatacg agatcactgt gtgactggag ttcagacgtg tgctcttccg    60
atct                                                                64

<210> SEQ ID NO 63
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 63
caagcagaag acggcatacg agatattggc gtgactggag ttcagacgtg tgctcttccg    60
atct                                                                64

<210> SEQ ID NO 64
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 64
caagcagaag acggcatacg agatgatctg gtgactggag ttcagacgtg tgctcttccg    60
atct                                                                64

<210> SEQ ID NO 65
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 65
caagcagaag acggcatacg agattcaagt gtgactggag ttcagacgtg tgctcttccg    60
atct                                                                64

<210> SEQ ID NO 66
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 66
caagcagaag acggcatacg agatctgatc gtgactggag ttcagacgtg tgctcttccg    60
atct                                                                64

<210> SEQ ID NO 67
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 67
```

```
caagcagaag acggcatacg agataagcta gtgactggag ttcagacgtg tgctcttccg    60
atct                                                                64

<210> SEQ ID NO 68
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 68
caagcagaag acggcatacg agatgtagcc gtgactggag ttcagacgtg tgctcttccg    60
atct                                                                64

<210> SEQ ID NO 69
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 69
caagcagaag acggcatacg agattacaag gtgactggag ttcagacgtg tgctcttccg    60
atct                                                                64

<210> SEQ ID NO 70
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 70
caagcagaag acggcatacg agattgttga ctgtgactgg agttcagacg tgtgctcttc    60
cgatct                                                              66

<210> SEQ ID NO 71
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 71
caagcagaag acggcatacg agatacggaa ctgtgactgg agttcagacg tgtgctcttc    60
cgatct                                                              66

<210> SEQ ID NO 72
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 72
caagcagaag acggcatacg agattctgac atgtgactgg agttcagacg tgtgctcttc    60
cgatct                                                              66

<210> SEQ ID NO 73
<211> LENGTH: 66
<212> TYPE: DNA
<213> ORGANISM: Artificial Sequence
```

<220> FEATURE:
<223> OTHER INFORMATION: Synthetic polynucleotide

<400> SEQUENCE: 73
caagcagaag acggcatacg agatcgggac gggtgactgg agttcagacg tgtgctcttc      60
cgatct      66

<210> SEQ ID NO 74
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 74
caagcagaag acggcatacg agatgtgcgg acgtgactgg agttcagacg tgtgctcttc      60
cgatct      66

<210> SEQ ID NO 75
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 75
caagcagaag acggcatacg agatcgtttc acgtgactgg agttcagacg tgtgctcttc      60
cgatct      66

<210> SEQ ID NO 76
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 76
caagcagaag acggcatacg agataaggcc acgtgactgg agttcagacg tgtgctcttc      60
cgatct      66

<210> SEQ ID NO 77
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 77
caagcagaag acggcatacg agataccgaa acgtgactgg agttcagacg tgtgctcttc      60
cgatct      66

<210> SEQ ID NO 78
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 78
caagcagaag acggcatacg agattacgta cggtgactgg agttcagacg tgtgctcttc      60
cgatct      66

<210> SEQ ID NO 79
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 79
caagcagaag acggcatacg agatatccac tcgtgactgg agttcagacg tgtgctcttc      60
cgatct                                                                66

<210> SEQ ID NO 80
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 80
caagcagaag acggcatacg agatatatca gtgtgactgg agttcagacg tgtgctcttc      60
cgatct                                                                66

<210> SEQ ID NO 81
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 81
caagcagaag acggcatacg agataaagga atgtgactgg agttcagacg tgtgctcttc      60
cgatct                                                                66

<210> SEQ ID NO 82
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 82
aatgatacgg cgaccaccga gatctacact ctttccctac acgacgctcg gggggg         56

<210> SEQ ID NO 83
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 83
aatgatacgg cgaccaccga gatctacact ctttccctac acgacgctcg ggtttttt       59

<210> SEQ ID NO 84
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(30)
<223> OTHER INFORMATION: n is a, c, g, or t, reverse complement of the
      barcode

```
<400> SEQUENCE: 84
caagcagaag acggcatacg agatnnnnnn gtgactggag ttcagacgtg tgctcttccg    60 atctggggg gggggggggg                                                80

<210> SEQ ID NO 85
<211> LENGTH: 85
<212> TYPE: DNA
<213> ORGANISM: Artificial Sequence
<220> FEATURE:
<223> OTHER INFORMATION: Synthetic polynucleotide

<400> SEQUENCE: 85
caagcagaag acggcatacg agatcgtgat gtgactggag ttcagacgtg tgctcttccg    60
atcttttttt tttttttttt ttttt                                         85

<210> SEQ ID NO 86
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 86
acactctttc cctacacgac gctcgggggg g                                  31

<210> SEQ ID NO 87
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 87
gtgactggag ttcagacgtg tgctcttccg atctggggg gggggggggg                50

<210> SEQ ID NO 88
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 88
cctgacggat ggccttttg cgtttctacc                                     30

<210> SEQ ID NO 89
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 89
aatgatacgg cgaccaccga gatctacact ctttgaccgg ggacttatca tccaacctgt    60
ta                                                                  62

<210> SEQ ID NO 90
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (25)..(30)
<223> OTHER INFORMATION: n is a, c, g, or t, reverse complement of the
      index

<400> SEQUENCE: 90
caagcagaag acggcatacg agatnnnnnn gtgactggag ttcagacgtg tgctcttccg    60
atct                                                                 64

<210> SEQ ID NO 91
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 91
acactctttg accggggact tatcatccaa cctgtta                             37

<210> SEQ ID NO 92
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 92
cccccccccc cccccccccc cccccc                                         26

<210> SEQ ID NO 93
<211> LENGTH: 4
<212> TYPE: DNA
<213> ORGANISM: Artificial Sequence
<220> FEATURE:
<223> OTHER INFORMATION: Synthetic polynucleotide

<400> SEQUENCE: 93 gatc                                                                  4

<210> SEQ ID NO 94
<211> LENGTH: 5
<212> TYPE: DNA
<213> ORGANISM: Artificial Sequence
<220> FEATURE:
<223> OTHER INFORMATION: Synthetic polynucleotide

<400> SEQUENCE: 94 ccggc                                                                 5

<210> SEQ ID NO 95
<211> LENGTH: 5
<212> TYPE: DNA
<213> ORGANISM: Artificial Sequence
<220> FEATURE:
<223> OTHER INFORMATION: Synthetic polynucleotide

<400> SEQUENCE: 95 ccggt                                                                 5

<210> SEQ ID NO 96
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 96
```

```
cggcaagttc atccttagga gaccgggg                                       28

<210> SEQ ID NO 97
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 97
gtgactggag ttcagacgtg tgctcttccg atctggggggg gggggggggg              50

<210> SEQ ID NO 98
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 98
aatgatacgg cgaccaccga gatctacact ctttccgggg acttatcagc caacctgtta    60

<210> SEQ ID NO 99
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(30)
<223> OTHER INFORMATION: n is a, c, g, or t, six-base-pair barcode
      sequence

<400> SEQUENCE: 99
caagcagaag acggcatacg agatnnnnnn gtgactggag ttcagacgtg tgctcttccg    60
atct                                                                 64

<210> SEQ ID NO 100
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 100
acactctttc cggggactta tcagccaacc tgtta                               35
```